United States Patent
Liston et al.

(10) Patent No.: US 10,568,720 B2
(45) Date of Patent: Feb. 25, 2020

(54) DENTAL IMPLANTS WITH MARKERS FOR DETERMINING THREE-DIMENSIONAL POSITIONING

(71) Applicants: Todd C. Liston, Ogden, UT (US);
Mark H. Blaisdell, Bountiful, UT (US)

(72) Inventors: Todd C. Liston, Ogden, UT (US);
Mark H. Blaisdell, Bountiful, UT (US)

(73) Assignee: Estetic Implant Solutions, LLC,
Bountiful, UT (US)

( * ) Notice: Subject to any disclaimer, the term of this patent is extended or adjusted under 35 U.S.C. 154(b) by 58 days.

(21) Appl. No.: 15/952,064

(22) Filed: Apr. 12, 2018

(65) Prior Publication Data

US 2018/0228578 A1    Aug. 16, 2018

(51) Int. Cl.
*A61C 8/00* (2006.01)
*A61C 1/08* (2006.01)
(Continued)

(52) U.S. Cl.
CPC ............ *A61C 8/0093* (2013.01); *A61C 1/084* (2013.01); *A61C 5/77* (2017.02); *A61C 8/0001* (2013.01); *A61C 8/008* (2013.01); *A61C 13/20* (2013.01); *A61C 13/34* (2013.01); *A61B 2090/0808* (2016.02); *A61B 2090/0811* (2016.02); *A61B 2090/3937* (2016.02); *A61B 2090/3966* (2016.02); *A61C 5/70* (2017.02); *A61C 9/0053* (2013.01); *A61C 13/0001* (2013.01); *A61C 13/0004* (2013.01)

(58) Field of Classification Search
CPC .............. A61C 8/00–008; A61C 13/34; A61C 13/0004; A61C 9/0053; A61C 5/70

USPC .................................. 433/172–176, 213–214
See application file for complete search history.

(56) References Cited

U.S. PATENT DOCUMENTS

| 512,840 A | 1/1894 | Phelps |
| 1,335,372 A | 3/1920 | Fredericks |

(Continued)

FOREIGN PATENT DOCUMENTS

| WO | 2010/0077130 | 7/2010 |
| WO | 2010/141342 | 12/2010 |
| WO | 2011/157762 | 12/2011 |

OTHER PUBLICATIONS

U.S. Appl. No. 16/030,055, filed Jul. 9, 2018, Liston.
(Continued)

*Primary Examiner* — Yogesh P Patel
(74) *Attorney, Agent, or Firm* — Workman Nydegger

(57) ABSTRACT

Dental implants including radiopaque markers provided therein or thereon. The implant may also include customizable length characteristics. For example, a kit may include implants with different diameters (e.g., 3 diameters), where all of the implants are of a single (e.g., long) length. The appropriate diameter implant may be selected from the kit by the practitioner, and the long length implant may be cut (e.g., with a dental drill) to the appropriate length needed. The implants include radiopaque markers on or within the implant. For example, three series of markers may be provided on different "faces" of the implant, so that the three series of markers serve as reference points when scanning, allowing triangulation of the exact position of the implant in relation to the surrounding hard and soft oral tissues.

3 Claims, 41 Drawing Sheets

(51) Int. Cl.
*A61C 13/34* (2006.01)
*A61C 5/77* (2017.01)
*A61C 13/20* (2006.01)
*A61C 9/00* (2006.01)
*A61C 5/70* (2017.01)
*A61C 13/00* (2006.01)
*A61C 13/107* (2006.01)
*A61B 90/00* (2016.01)

(56) References Cited

U.S. PATENT DOCUMENTS

| | | | |
|---|---|---|---|
| 2,475,599 | A | 7/1949 | Erdle |
| 3,286,350 | A | 11/1966 | Cooper |
| 3,628,248 | A | 12/1971 | Kroder |
| 3,937,773 | A | 2/1976 | Huffman |
| 4,001,938 | A | 1/1977 | Cooper |
| 4,056,585 | A | 11/1977 | Waltke |
| 4,744,753 | A | 5/1988 | Ross |
| 4,975,059 | A | 12/1990 | Sendax |
| 4,986,753 | A | 1/1991 | Sellers |
| 5,071,345 | A | 12/1991 | Rosen |
| 5,180,303 | A | 1/1993 | Hornburg et al. |
| 5,306,145 | A | 4/1994 | Michael |
| 5,320,529 | A | 6/1994 | Pompa |
| 5,324,186 | A | 6/1994 | Bakanowski |
| 5,338,196 | A | 8/1994 | Beaty et al. |
| 5,431,567 | A | 7/1995 | Daftary |
| 5,469,908 | A | 11/1995 | Chmel et al. |
| 5,492,471 | A | 2/1996 | Singer |
| 5,651,675 | A | 7/1997 | Singer |
| 5,658,147 | A | 8/1997 | Phimmasone |
| 5,674,069 | A | 10/1997 | Osorio |
| 5,695,337 | A | 12/1997 | Tyszblat Sodoun |
| 5,735,692 | A | 4/1998 | Berger |
| 5,738,518 | A | 4/1998 | Nowak |
| 5,813,858 | A | 9/1998 | Singer |
| 5,839,898 | A | 11/1998 | Fernandes |
| 5,846,079 | A | 12/1998 | Knode |
| 5,871,358 | A | 2/1999 | Ingber et al. |
| RE36,126 | E | 3/1999 | Beaty et al. |
| 5,899,695 | A | 5/1999 | Lazzara |
| 5,911,580 | A | 6/1999 | Sharp et al. |
| RE36,689 | E | 5/2000 | Beaty et al. |
| 6,120,292 | A | 9/2000 | Buser |
| 6,155,828 | A | 12/2000 | Lazzara |
| 6,217,326 | B1 | 4/2001 | Hahn |
| 6,244,867 | B1 | 6/2001 | Aravena et al. |
| 6,283,753 | B1 | 9/2001 | Willoughby |
| 6,290,499 | B1 | 9/2001 | Lazzara et al. |
| 6,299,448 | B1 | 10/2001 | Zdrahala et al. |
| 6,300,390 | B1 | 10/2001 | Angeletakis |
| 6,361,721 | B1 | 3/2002 | Stern |
| 6,386,876 | B1 | 5/2002 | Lee |
| 6,431,867 | B1 | 8/2002 | Gittelson |
| 6,537,069 | B1 | 3/2003 | Simmons |
| 6,626,671 | B2 | 9/2003 | Klardie et al. |
| RE38,630 | E | 10/2004 | Lazzara et al. |
| 7,018,207 | B2 | 3/2006 | Prestipino |
| 7,156,660 | B2 | 1/2007 | Huffman |
| 7,179,089 | B2 | 2/2007 | Sims et al. |
| 7,287,983 | B2 | 10/2007 | Ilan |
| 7,347,689 | B2 | 3/2008 | Huffman |
| 7,429,175 | B2 | 9/2008 | Gittelson |
| 7,563,397 | B2 | 7/2009 | Schulman et al. |
| 7,632,095 | B2 | 12/2009 | Ostman et al. |
| D611,148 | S | 3/2010 | White, III |
| 7,762,814 | B2 | 7/2010 | van der Zel |
| 7,798,812 | B2 | 9/2010 | Last-Pollak |
| 7,816,423 | B2 | 10/2010 | Karim et al. |
| 7,922,488 | B2 | 4/2011 | Falk et al. |
| 7,922,490 | B2 | 4/2011 | Wen |
| 8,048,345 | B2 | 11/2011 | Feith |
| 8,105,081 | B2 | 1/2012 | Bavar |
| 8,382,477 | B2 | 2/2013 | Philibin |
| 8,425,231 | B1 | 4/2013 | Hochman et al. |
| 8,628,327 | B1 | 1/2014 | Blaisdell et al. |
| 8,831,322 | B2 | 9/2014 | Abboud |
| 9,452,032 | B2 | 9/2016 | Hochman et al. |
| 9,572,640 | B2 | 2/2017 | Blaisdell |
| 9,763,753 | B2 | 9/2017 | Wang |
| 9,820,831 | B2 | 11/2017 | Cho |
| 9,895,209 | B2 | 2/2018 | Blaisdell |
| 10,016,260 | B2 | 7/2018 | Blaisdell |
| 10,136,974 | B2 | 11/2018 | Vergoullis et al. |
| 2001/0005575 | A1 | 6/2001 | Kanomi |
| 2002/0064758 | A1 | 5/2002 | Lee |
| 2003/0170593 | A1 | 9/2003 | Dorfman |
| 2005/0040551 | A1 | 2/2005 | Biegler et al. |
| 2005/0048440 | A1 | 3/2005 | Feng |
| 2005/0084821 | A1 | 4/2005 | Sims et al. |
| 2005/0115460 | A1 | 6/2005 | Petticrew |
| 2006/0046229 | A1 | 3/2006 | Teich |
| 2006/0105296 | A1 | 5/2006 | Linder et al. |
| 2006/0121416 | A1 | 6/2006 | Engman |
| 2006/0263749 | A1 | 11/2006 | Koide |
| 2006/0286508 | A1 | 12/2006 | Bassett |
| 2007/0092853 | A1 | 4/2007 | Liu et al. |
| 2007/0111165 | A1 | 5/2007 | Wallick |
| 2007/0281278 | A1 | 12/2007 | Jorneus |
| 2008/0081317 | A1 | 4/2008 | White |
| 2008/0220390 | A1* | 9/2008 | Klein .................. A61C 1/084 |
| | | | 433/76 |
| 2008/0293013 | A1 | 11/2008 | Lussi |
| 2008/0293016 | A1 | 11/2008 | Lussi |
| 2008/0293017 | A1 | 11/2008 | Lussi |
| 2009/0081618 | A1 | 3/2009 | LaMar |
| 2009/0208906 | A1 | 8/2009 | Callan |
| 2010/0092921 | A1 | 4/2010 | Huffman |
| 2010/0266985 | A1 | 10/2010 | Yau et al. |
| 2010/0279254 | A1 | 11/2010 | White |
| 2011/0008754 | A1 | 1/2011 | Bassett et al. |
| 2011/0081627 | A1 | 4/2011 | Sun et al. |
| 2011/0111368 | A1 | 5/2011 | Arnold et al. |
| 2011/0200968 | A1 | 8/2011 | Laizure, Jr. |
| 2011/0229859 | A1 | 9/2011 | White |
| 2011/0024426 | A1 | 10/2011 | Amber et al. |
| 2012/0022648 | A1 | 1/2012 | Vult Von Steyern |
| 2012/0052465 | A1 | 3/2012 | Von Both et al. |
| 2012/0164593 | A1 | 6/2012 | Bavar |
| 2013/0101964 | A1 | 4/2013 | Fudim |
| 2013/0177872 | A1 | 7/2013 | Blaisdell |
| 2013/0288202 | A1 | 10/2013 | Hochman et al. |
| 2014/0004481 | A1* | 1/2014 | Spahn .................. A61C 8/0012 |
| | | | 433/173 |
| 2017/0007372 | A1 | 1/2017 | Blaisdell |
| 2017/0112598 | A1* | 4/2017 | Suttin .................. A61C 8/0001 |
| 2017/0128176 | A1 | 5/2017 | Vergoullis |
| 2017/0172714 | A1 | 6/2017 | Blaisdell |
| 2017/0239020 | A1* | 8/2017 | McDonald ........... A61C 8/0033 |
| 2018/0161134 | A1 | 6/2018 | Liston |

OTHER PUBLICATIONS

"Contour Healer, The Superior Choice for Restorative Healing", http://contourhealer.com/about-us, Based on information and believe—Available at least as early as Dec. 13, 2012.

Custom Temporary Components—https://www.inclusivedental.com/ToothReplacementSolutions/PartiallyEdentulous/InclusiveToothReplacementSolution/CustomTemporaryComponents.aspx (Accessed Apr. 11, 2012).

International Search Report and Written Opinion cited in PCT Application No. PCT/US2013/020992 dated Apr. 25, 2013.

PreFormance Post Cement-retained provisional option (Based on information and belief, available at least as early as Jan. 15, 2012).

U.S. Appl. No. 13/347,127, Mar. 25, 2013, Non-Final Office Action.

U.S. Appl. No. 13/633,387, Sep. 10, 2013, Notice of Allowance.

U.S. Appl. No. 13/347,127, Sep. 24, 2013, Final Office Action.

U.S. Appl. No. 13/347,127, Apr. 3, 2014, Non-Final Office Action.

U.S. Appl. No. 13/347,127, Aug. 19, 2014, Final Office Action.

U.S. Appl. No. 14/152,369, Sep. 12, 2016, Office Action.

(56) References Cited

OTHER PUBLICATIONS

U.S. Appl. No. 14/152,369, Oct. 13, 2016, Notice of Allowance.
U.S. Appl. No. 14/485,351, Mar. 2, 2017, Office Action.
U.S. Appl. No. 14/327,869, Mar. 6, 2017, Office Action.
U.S. Appl. No. 14/485,351, Oct. 19, 2017, Final Office Action.
U.S. Appl. No. 14/327,869, Oct. 30, 2017, Notice of Allowance.
U.S. Appl. No. 14/485,351, Feb. 23, 2018, Office Action.
U.S. Appl. No. 14/485,351, May 16, 2018, Notice of Allowance.
"The BellaTek® Encode® Impression System—Optimization by Design®: Product Brochure", BioMet 3i, 2013, pp. 1-8, accessed via <www.biomet3i.com/.../BellaTek%20Encode%20Brochure_ART1059_eu.pdf> on Jul. 9, 2019.
"OsseoGuard® Non-Resorbables: Product Brochure", Zimmer Biomet Dental, 2018, pp. 1-12 accessed via <https://www.zimmerbiometdental.com/en-US/wps/wcm/connect/dental/629fb5b5-7fc3-42b3-8237-ad96294cadee/ZBINST0033_REV_A_OsseoGuard_PTFE_Brochure_final_SECURED.pdf?MOD=AJPERES&CACHEID=ROOTWORKSPACE.Z18_1O041O02L8PAF0A9JPRUH520H7629fb5b5-7fc3-42b3-8237-ad96294cadee> on Jul. 9, 2019.
U.S. Appl. No. 15/280,804, Oct. 18, 2018, Office Action.
VP Innovato Holdings, Cervico Mold, [accessed online Nov. 27, 2018] URL: http://innovatoholdings.com/cervico-mold/.
BIOMET 3i Brochure "The BellaTek Encode Impression System".
VP Innovato Holdings, Cervico Guide, [accessed online Feb. 4, 2019] URL: http://innovatoholdings.com/cervico-guide/.
Nobel Biocare [accessed Feb. 4, 2019] URL: http://www.nobelbiocare.com/international/en/home.html.
U.S. Appl. No. 15/453,365, Sep. 3, 2019, Office Action.
U.S. Appl. No. 15/893,320, Sep. 3, 2019, Notice of Allowance.
U.S. Appl. No. 15/270,804, Sep. 26, 2019, Notice of Allowance.

* cited by examiner

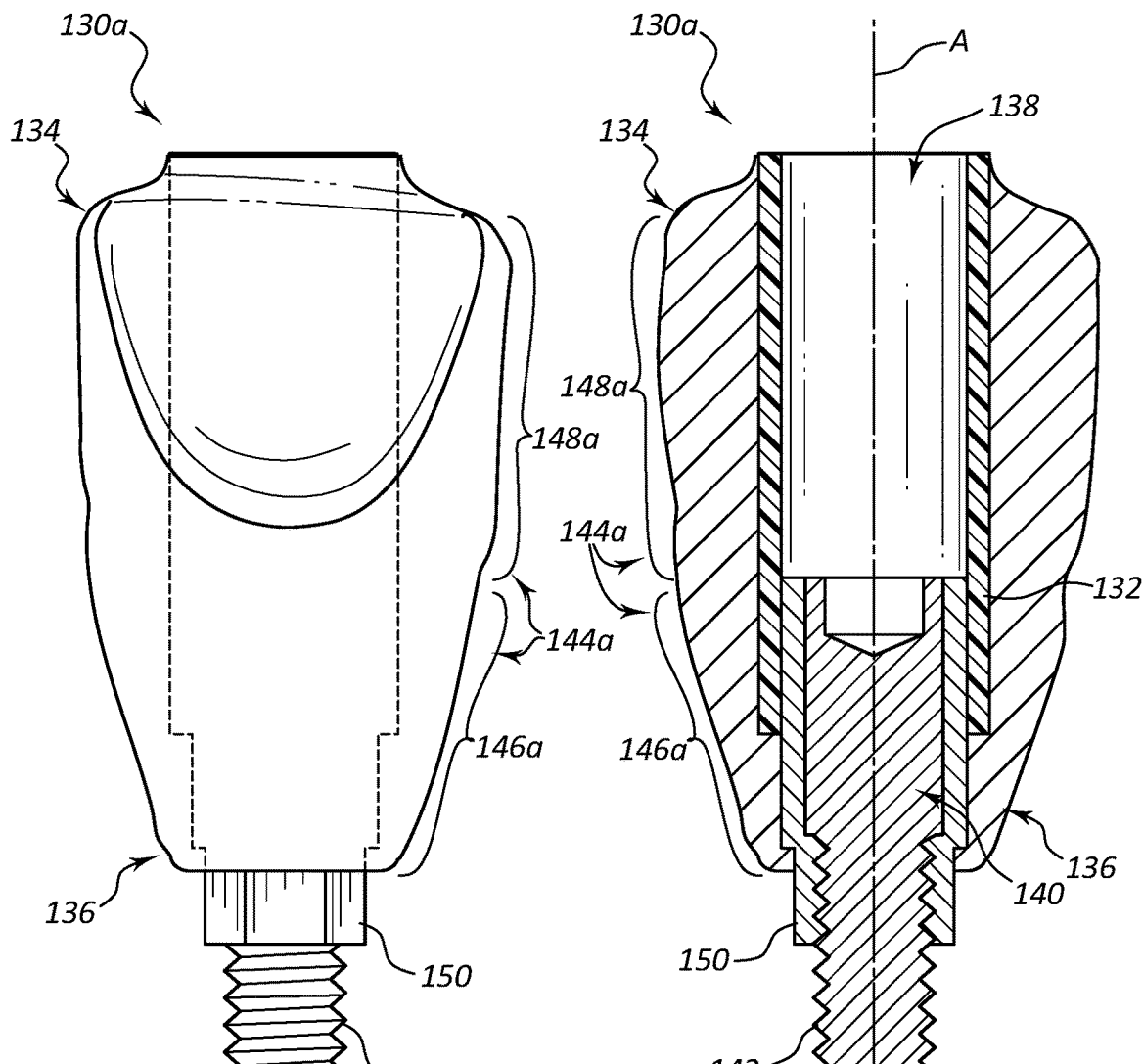
FIG. 2C
FIG. 2E
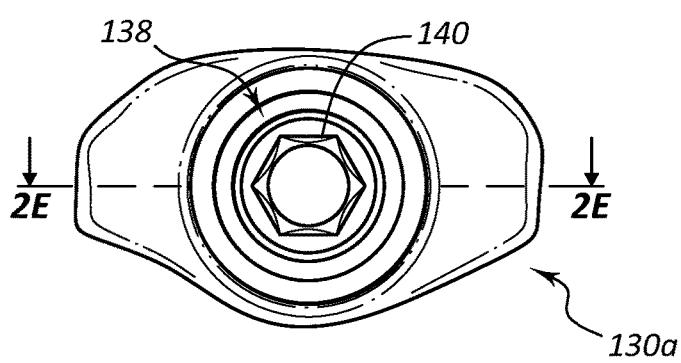
FIG. 2D

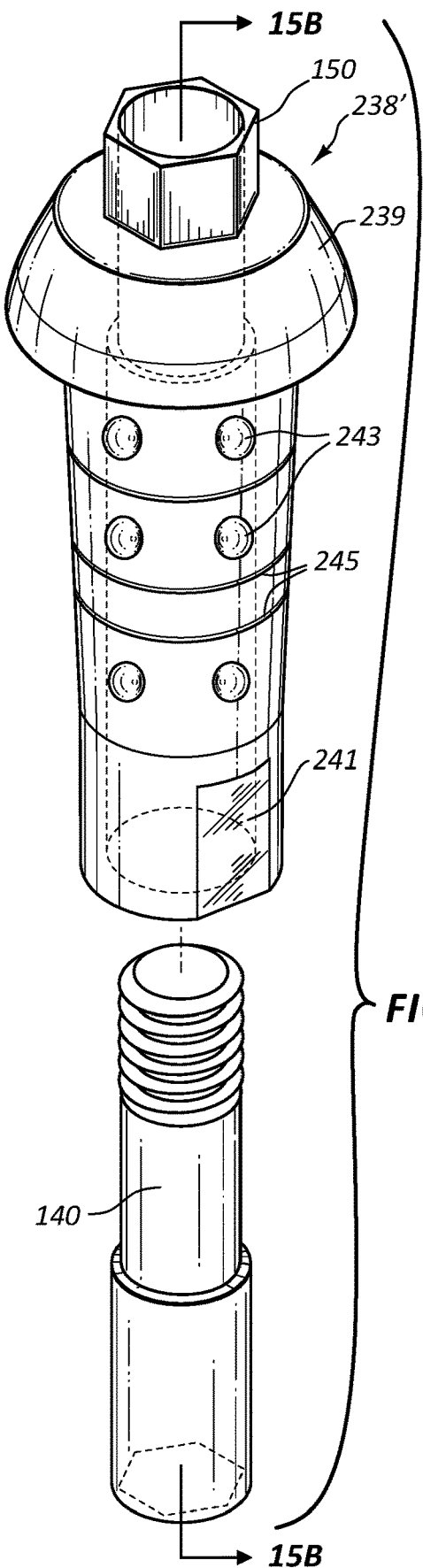
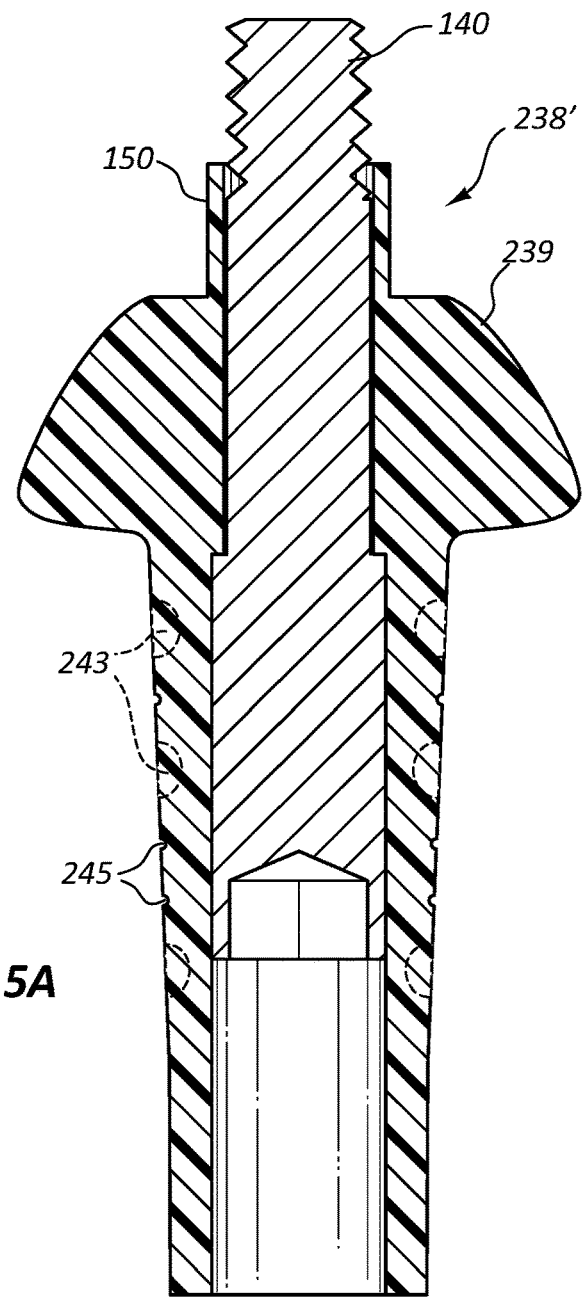
FIG. 15A
FIG. 15B

DENTAL IMPLANTS WITH MARKERS FOR DETERMINING THREE-DIMENSIONAL POSITIONING

CROSS-REFERENCE TO RELATED APPLICATIONS

The present application incorporates by reference U.S. patent application Ser. No. 15/270,804 filed Sep. 20, 2016, which is a continuation-in-part of U.S. patent application Ser. No. 14/327,869 filed Jul. 10, 2014, now U.S. Pat. No. 9,895,209, which is a continuation-in-part of U.S. patent application Ser. No. 14/152,369, filed Jan. 10, 2014, now U.S. Pat. No. 9,572,640, which is a continuation-in-part of U.S. patent application Ser. No. 13/633,387 filed Oct. 2, 2012, now U.S. Pat. No. 8,628,327. U.S. patent application Ser. No. 14/327,869 is also a continuation in part of International Application No. PCT/US2013/020992, filed Jan. 10, 2013, which claims priority to U.S. patent application Ser. No. 13/347,127, filed Jan. 10, 2012, now abandoned. U.S. patent application Ser. No. 15/270,804 filed Sep. 20, 2016 is also a continuation-in-part of U.S. patent application Ser. No. 14/485,351, filed Sep. 12, 2014. The disclosure of each of the above patents and applications is herein incorporated by reference in its entirety.

BACKGROUND OF THE INVENTION

1. The Field of the Invention

This invention relates to dental implants, as well as methods and systems associated with such dental implants. Dental implants have been well established in the field of dentistry as a suitable tool for supporting placement of a prosthetic tooth that replaces missing and/or lost teeth. Since the advent of the dental implant, continued research and innovation in implant placement and prosthetic restoration has taken place. That said, there currently exists a lack of knowledge in establishing the exact position of a dental implant in 3 dimensions (i.e., axial, coronal, and sagittal axes) in the subgingival environment.

2. Background and Relevant Art

In modern dentistry, when one or more teeth are removed it is desirable to eventually replace the tooth or teeth with a prosthesis (e.g., a crown, bridge, etc.), although this is typically accomplished weeks later. Once the tooth is removed or missing, a dental implant is placed into the bone tissue of the jaw to provide a secure foundation upon which a prosthesis can be supported. Typically, the site is allowed to heal for a period of time prior to installation of the permanent prosthesis. Currently, a device known as a healing cap, abutment, or cuff is coupled into the dental implant while the site is allowed to heal, to cap or cover the inside of the dental implant and to preserve the ability to re-access the dental implant once the site has sufficiently healed, when it is desired to install a prosthesis. Once the site has healed (e.g., typically 1.5 to 6 months after implant placement), the healing cap, abutment, or cuff is removed, and a custom prosthesis (e.g., a crown) may be installed, supported by the dental implant anchored within the jaw bone.

Because of the inexact information available to the practitioner as to the exact position of the implant installed in the subgingival environment, it can be difficult for a dental practitioner to efficiently produce a temporary or permanent prosthesis under the typical circumstances. For example, it is often necessary for the practitioner and the laboratory to interact with one another in an iterative manner, in order to fabricate the desired prosthesis for installation.

BRIEF SUMMARY

Identifying the exact spatial position and orientation of the implant as installed in the jaw bone of a patient through imaging, including the relationship between the surrounding soft and hard oral tissues, would allow for more efficient fabrication of temporary and permanent prosthetics and attachments by limiting the amount of time and materials needed by the practitioner and laboratory. Such information would also minimize the multiplication of procedures to the patient. For example, at present, a patient typically is required to visit the practitioner multiple times as various iterations of the prosthetic are developed and fitted to the implant installed in the patient's jaw, and to interface the prosthetic with the surrounding hard and soft tissues of the patient. Because of limitations in the field of three-dimensional imaging, as well problems specific to its implementation with an installed dental implant, it has not yet been possible to provide sufficient three-dimensional image scanned data to identify the exact spatial position of the implant in the jaw bone, and to accurately model interaction between the implant, surrounding oral tissues, and a prosthesis to be installed, and to fabricate such a prosthesis to narrow tolerances that would allow such a manufactured prosthesis to provide good results.

In an aspect, the present invention relates to dental implants and methods of use that provide for customizing length of the dental implant, and/or markers positioned on or within the implant which in conjunction with imaging techniques, allow for precise determination of the particular position and orientation of the implant in the jaw bone of the patient, and the exact spatial relationship between such implant and the surrounding hard and soft tissues of the patient. For example, current implants do not provide any radiopaque markings on or within the implant, which would greatly aid the practitioner in determining the spatial relationship between the implant (or particular portions thereof) relative to surrounding hard and soft tissues in the oral cavity. Furthermore, imaging techniques are becoming available that provide a higher degree of resolution for determining such spatial relationships, if such markers were provided on the implant. Such imaging techniques may include, but are not particularly limited to CT imaging, MRI imaging, x-ray imaging, and ultrasound. Ultrasound imaging may be particularly desirable as it does not expose the patient to any appreciable dose of electromagnetic radiation.

One embodiment of a dental implant as described herein may include an implant body including a threaded distal end configured for implant into a jaw bone of a patient, and a proximal attachment end configured for attachment to an abutment and/or a prosthesis. The abutment or prosthesis may be, e.g., any of the anatomical healing caps or cuffs as disclosed herein, and in others of Applicants' patents and patent applications. The threaded distal end and the proximal attachment end may be formed from a biocompatible material (e.g., typically titanium). The implant body may further include a plurality of radiopaque markers positioned on or within the implant body (e.g., on an exterior of the implant (e.g., between the exterior threads, on the exterior threads), or inside the implant body (e.g., in the hollow interior). Such radiopaque markers may be formed from a different material, having a radiopacity that is greater than that of the biocompatible material from which the threaded distal end and proximal attachment end are formed (e.g., gold, tantalum, tungsten, molybdenum, platinum, palladium, or other metals or allows having relatively high radiopacity).

The markers may be positioned at predisposed, equally spaced intervals, as one progresses vertically up the longitudinal axis of the implant. For example, the markers may be positioned 2 mm apart from one another, or the like (e.g., 1-3 mm spacing). The markers may further be provided on different "faces" of the implant. For example, the markers may be provided on 3 different such faces, so that imaging software can "triangulate" the exact position of the implant in 3-dimensions during imaging. Because the exterior of the implant, at least in the threaded distal portion, is circular in cross-section, such faces may be defined by a given angular separation between such markings. For example, the markings may be located 90° apart, or 120° apart, or any value in between. Various other angular separations may also be possible. Where the markers are positioned on the interior, similar considerations may apply, particularly where the interior may also be bounded by a circular cross-section.

In an embodiment, the markings may be provided as three (or another number) series of markings, each series including markings that are vertically aligned with one another (e.g., where each marking is a horizontal line or other horizontal feature), one marking over the adjacent marking, each spaced apart (e.g., 2 mm) from one another.

The radiopaque markers on or within the implant serve as reference points when building the scanned virtual model or image from the scan data.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2C is a side elevation view of the anatomical healing cap of FIG. 2B.

FIG. 2D is a top view of the anatomical healing cap of FIG. 2B.

FIG. 2E is a cross-sectional view through the anatomical healing cap of FIG. 2B.

FIGS. 15A-15B illustrate perspective and cross-sectional views, respectively, of the temporary abutment core and an associated screw for retaining the core in the distal end of the elongate handle during manufacture of the anatomical healing cap.

DETAILED DESCRIPTION OF THE PREFERRED EMBODIMENTS

I. Introduction

Figure 1A:
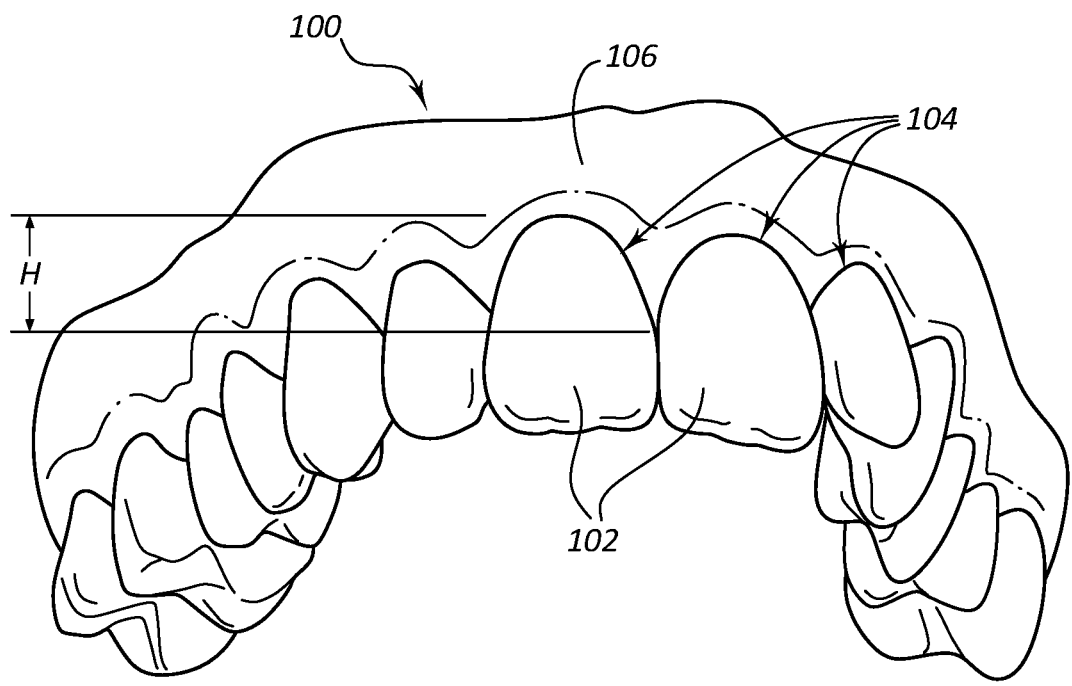
FIG. 1A is a perspective view of an exemplary upper dental arch.

One problem with conventional healing caps and related methods of oral surgery is that those features of the gingiva that provide much of the characteristic natural aesthetic appearance of natural teeth and adjacent gum tissue are almost always lost once a tooth is pulled and replaced with a prosthesis. In particular, the gingival tissue surrounding the crown of a natural tooth where it emerges (i.e., its emergence profile) is lost during such procedures.

The gingival cuff refers to the generally scalloped pattern of the gingival tissue that is most prominently seen along the buccal surface of the teeth. The height of contour of the gingival cuff refers to the difference between the most occlusal extension of the gingiva (i.e., between teeth) as compared to its location at the center of a tooth. Generally, the height of contour of the gingival cuff is greatest at a location between two adjacent teeth. In other words, the location of the gingival cuff extends occlusally to its greatest extent at this location between the teeth. At a location corresponding to a buccal center face of a tooth, the location of the gingival cuff exhibits its lowest occlusal extension.

When a natural tooth is pulled and eventually replaced with a custom crown or other prosthesis, much of the dynamic range of the previous height of contour is lost because the gingival tissue between adjacent teeth recedes, and is lost.

Gingival tissue disposed between adjacent teeth is often referred to as the interdental papilla. This tissue resides between the void resulting from the pulled tooth and the adjacent remaining tooth. As a result of the loss of the tooth, the interdental papilla may atrophy and fill the void over time. As a result, much of the interdental papilla tissue, particularly the initial and desirable aesthetic characteristics of this tissue, also tends to be lost upon removal of the natural tooth.

At the extreme gingival edge of the gingival cuff there is gingival tissue that overlies the underlying jaw bone. This gingival tissue typically exhibits a prominence in the buccal direction (i.e., it sticks out or protrudes bucally) and is often referred to as buccal prominence. While the gingival tissue over this bony tissue is not necessarily lost, the prominence by which the tissue sticks out bucally is typically lost when a natural tooth is pulled.

In one aspect, the present disclosure is directed to devices, kits, and methods allowing small-scale manufacture of customizable sculptable anatomical healing caps, allowing the practitioner to chair-side manufacture the needed anatomical healing caps for use with any given patient. Because the healing caps anatomically match the given tooth position where they are placed, they provide custom filing of at least the emergence portion of the void resulting from removal of a selected tooth (or where a tooth should be in the case of a congenitally missing tooth). Because of the anatomical features of the healing cap, use of the healing cap advantageously allows the practitioner to better preserve the desirable aesthetic features of the gingival tissue surrounding and associated with natural teeth.

FIGS. 1A-1F illustrate an upper dental arch, as well as typical steps employed in removal of a tooth, installation of an implant, and placement of a state of the art healing cuff or cap. For example, FIG. 1A shows a person's upper dental arch 100 including central incisors 102. Also apparent in FIG. 1A is the gingival cuff 104 where the natural teeth emerge from the gingival tissue, and the typical height of contour where the highest contour $H_2$ is between two adjacent teeth, while the lowest contour or point along the gingival cuff is $H_1$, at the center of the buccal face of the teeth. The difference H between $H_2$ and $H_1$ represents the height of contour associated with the natural teeth and gingival cuff prior to removal of the natural tooth.

Figure 1B:
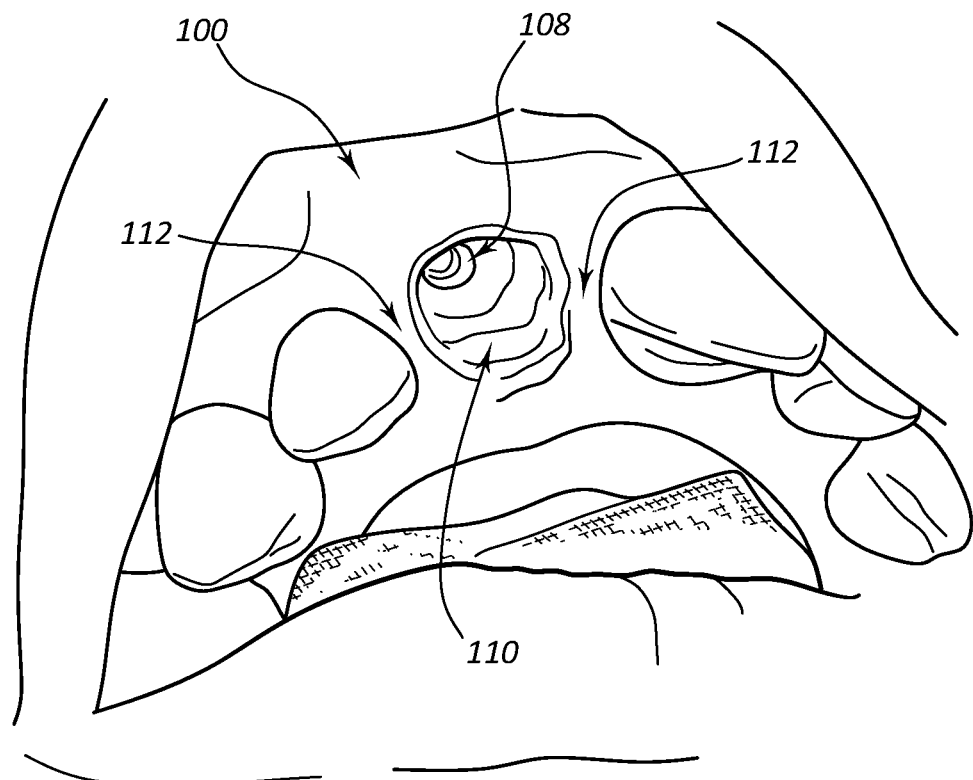
FIG. 1B is a perspective view of the dental arch of FIG. 1A in which a central incisor has been removed, leaving a void.

In addition to the gingival cuff, a buccal prominence 106 is associated with the gingival edge of gingival cuff 104, disposed gingivally relative to the crown of each respective tooth (e.g., labeled buccal prominence 106 corresponds to tooth 102). FIG. 1B shows the dental arch 100 after central incisor 102 has been removed, leaving a void 108 once occupied by the root of tooth 102. The top or most gingival portion of void 108 is the emergence portion 110 of void 108, whose contours are defined by the shape of the emergence portion of the tooth 102, just below the crown portion of the tooth. Also apparent in FIG. 1B is the interdental papilla 112.

Figure 1C:
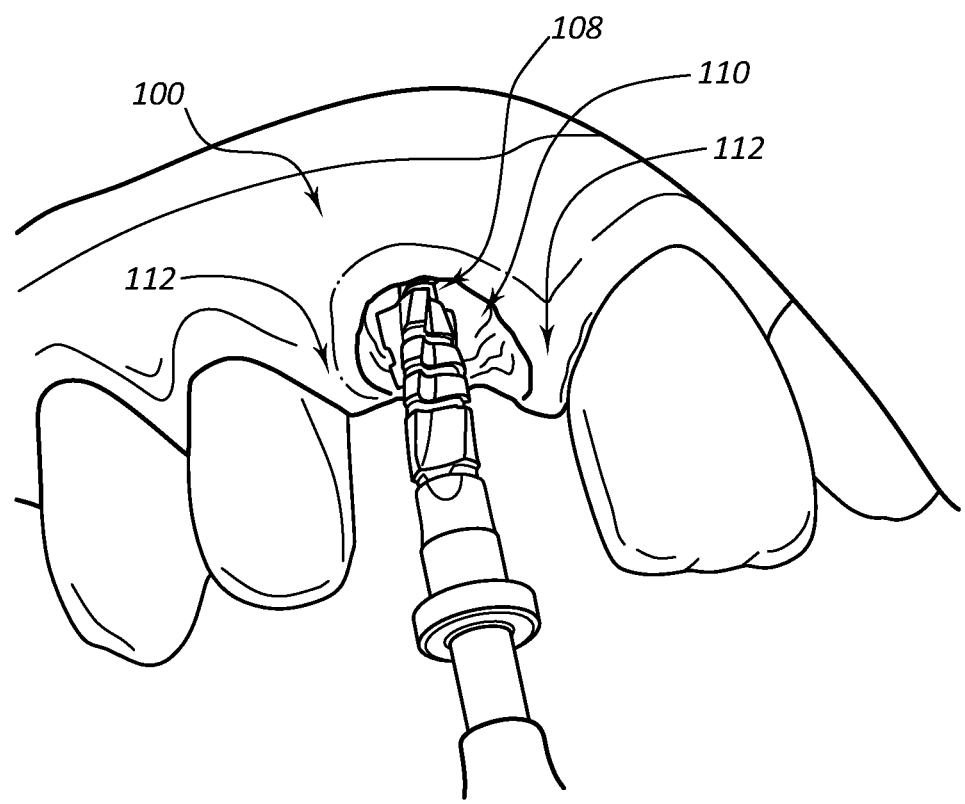
FIG. 1C is a perspective view of the dental arch of FIG. 1B in which a dental implant surgical drill is used to prepare an anchor hole in the underlying bone for anchoring a dental implant.
Figure 1D:
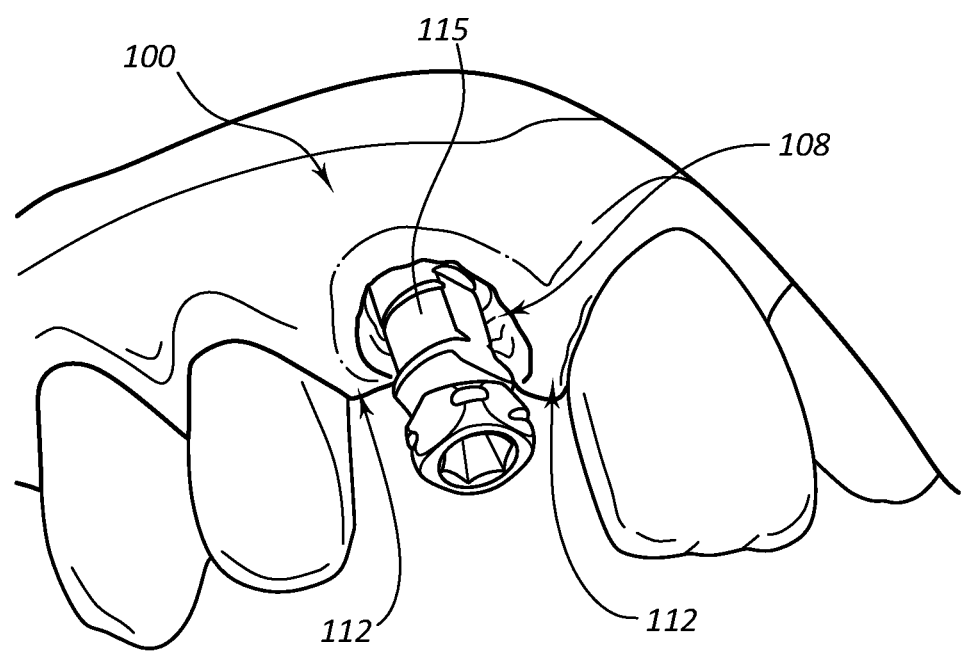
FIG. 1D is a perspective view of the arch of FIG. 1C as an implant is being inserted (e.g., with the aid of a transfer coping).
Figure 1E:
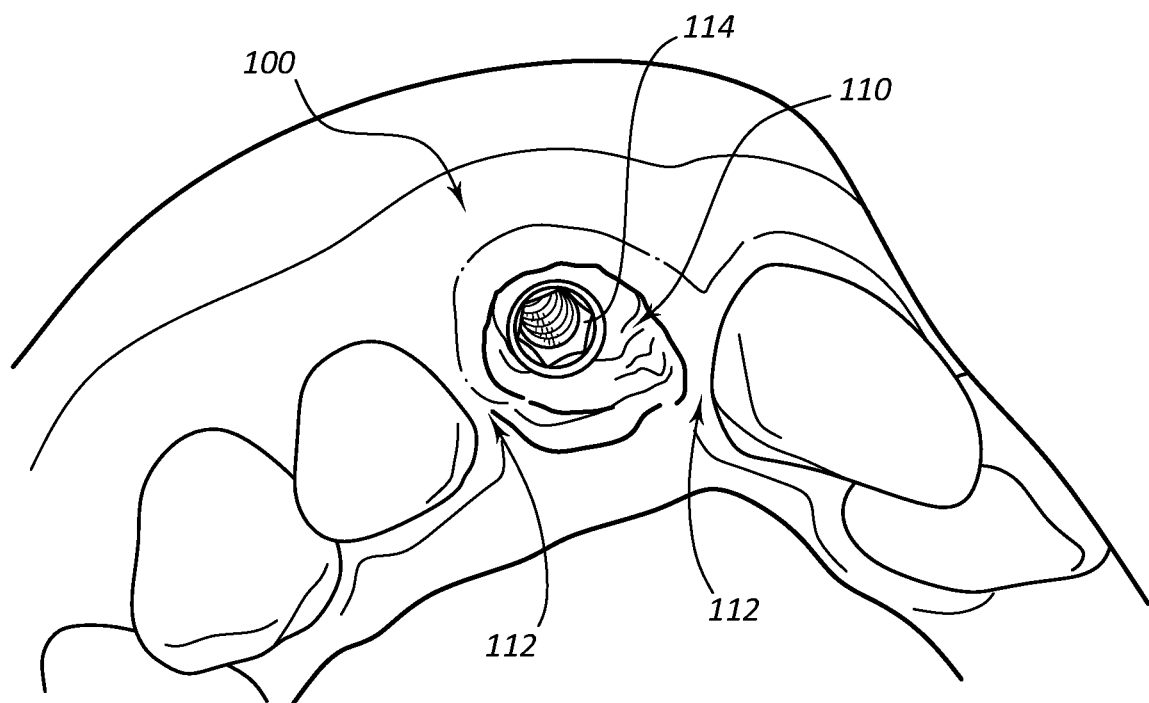
FIG. 1E is a perspective view of the arch and into the void showing the implant anchored into the bottom of the void.
Figure 1F:
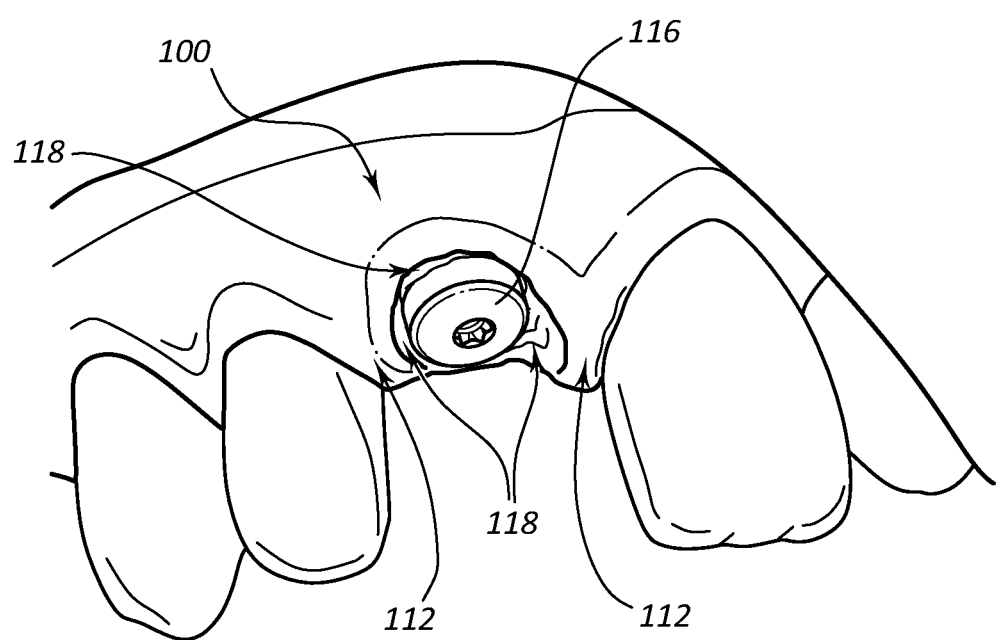
FIG. 1F is a perspective view of the arch showing a state of the art healing cuff coupled into the implant.

As shown in FIG. 1C, the void 108 is prepared to receive a dental implant 114 by drilling into the bone tissue of the underlying jaw bone at the bottom of void 108, after which a dental implant 114 may be inserted therein, as shown in FIG. 1D-1E. FIG. 1D shows a transfer coping 115 or similar structure being used to aid in seating the implant 114 into void 108. FIG. 1E illustrates a view down into void 108 once dental implant 114 has been fully seated within the prepared underlying bony tissue (and transfer coping 115 has been uncoupled from implant 114). Much of the lower portion of void 108 may be filled by dental implant 114, while the emergence portion 110 remains unfilled. FIG. 1F shows installation of a state of the art healing cap or cuff 116, which couples into dental implant 114. Healing cap or cuff 116 is typically provided in various sizes, each of which is cylindrical (e.g., each of a different diameter and/or height). A healing cap or cuff is selected from the available sizes and coupled into dental implant 114. Healing cap or cuff 116 may remain in place for several weeks (e.g., 1.5 to 6 months) while the site heals. As shown in FIG. 1F, because the healing cap or cuff 116 is not anatomically shaped to fill the emergence portion 110 of void 108, gaps 118 remain between healing cap or cuff 116 and the gingival walls defining emergence portion 110. Placement of the healing cap or cuff 116 may be the end of what is termed the first stage procedure. It will be understood that while described in terms of various stages, healing caps or cuffs 116 may be placed in various other oral surgery procedures (e.g., second stage, immediate placement, subsequent placement, etc.). Similarly, the inventor's anatomical healing cap devices, systems and methods may be employed in various oral surgery procedures (e.g., during a first or second stage procedure, in an immediate placement procedure, in a delayed placement procedure, or in any other appropriate oral surgery procedure). The greatest benefit may be obtained where the anatomical healing cap devices are placed immediately or soon after placement of the implant, so that the gingival tissue is immediately supported, and loss of desired gingival tissue features is minimized.

By way of example, in a subsequent second stage procedure, after a healing period of at least several weeks, the person may return to the practitioner's office, the healing cap or cuff 116 may be removed, and a permanent prosthesis may be installed by coupling into implant 114. During the healing period, the gingival tissue surrounding healing cap or cuff 116 progressively adapts to the shape provided by healing cap or cuff 116, collapsing into, growing into, or otherwise filling gaps 118. In addition, the height of contour of the gingival cuff tends to be compressed (i.e., reduced) as the tissue between adjacent teeth recedes, the interdental papilla fall or otherwise fill gaps 118, and the buccal prominence 106 recedes so as to be less prominent bucally. As a result, the emergence profile and other desirable gingival features are compromised. At this stage, even if one were to install a crown or other prosthesis that were a perfect match to the natural tooth, including the subgingival emergence portion, it is often too late to recapture the prior characteristics of the surrounding gingival tissue, which have been lost. Furthermore, when installing such a prosthesis at this later stage, the gingival tissue that has grown into gaps 118 is often cut away or compressed in order to make space for the prosthesis. Such activity can lead to subsequent necrosis of the gingival tissue.

Customizable sculptable anatomical healing caps specifically configured to preserve or restore or create (in the case of missing teeth) as much of this gingival tissue, its emergence profile, and other features as possible are disclosed in the inventors' earlier U.S. patent application Ser. No. 13/347,127 filed Jan. 10, 2012 and entitled CUSTOMIZABLE SCULPTABLE ANATOMICAL HEALING CAPS, SYSTEMS, AND RELATED METHODS, herein incorporated by reference in its entirety. The present application discloses casting jigs, and related kits and methods for use in manufacture of the anatomical healing caps. The casting jigs, kits, and methods advantageously allow a practitioner to manufacture such anatomical healing caps himself or herself. Manufacture may be easily achieved chair-side, on a small scale, or both. Of course, such casting jigs could also be employed in a large-scale manufacture process.

III. Exemplary Customizable Sculptable Anatomical Healing Caps

FIGS. 2A-2E illustrate various views of an exemplary sculptable anatomical healing cap 130a configured to fill the emergence portion of a void resulting from removal of an upper central incisor. Sculptable anatomical healing cap 130*a* includes an elongate body 132 extending between a proximal end 134 and a distal dental implant insertion end 136. Body 132 may be advantageously hollow, including a hollow channel 138 with open ends and extending generally along longitudinal axis A so as to allow insertion of coupling screw member 140 into hollow channel 138, by which external threads 142 can be coupled into corresponding internal threads of a dental implant 114.

Sculptable healing cap 130*a* advantageously includes an enlarged cuff body 144*a* extending laterally outward from hollow elongate body 132. In one embodiment, body 132 and body 144*a* are integral. In other words, they may be one and the same, such that no separate body 132 is present. This is particularly so where the cuff body 144*a* is formed by casting a curable or otherwise settable dental material within a casting jig. Of course, a separate body 132 may be provided in such a casting jig manufactured embodiment, by casting the cuff body about body 132 (e.g., body 132 may initially comprise a straw or temporary abutment inserted into the well of the casting jig, about which the cuff body 144*a* is formed. Enlarged cuff body 144*a* is disposed between proximal end 134 and distal end 136, and advantageously is shaped, as manufactured, to provide a substantially custom fit so as to fill emergence portion 110 of void 108. In the illustrated configuration, cuff body 144*a* includes a subgingival or lower portion 146*a* and an exposed or upper portion 148*a*. Subgingival portion 146*a* becomes inserted within emergence portion 110 of void 108 during use, while exposed portion 148*a* resides gingivally above void 108.

Both portions 146*a* and 148*a* may be shaped to mimic the shape of the natural tooth which may have immediately prior resided within void 108. In particular, subgingival portion 146*a* is shaped to mimic that portion of the natural tooth which resides immediately below the gingival surface, so that this portion 146*a* mimics the emergence portion including the emergence profile of the natural tooth. In order to mimic the natural tooth contours just below the gingival surface, the subgingival portion 146*a* includes an asymmetrical cross-section and an irregular surface which mimic the emergence portion and emergence profile of the natural tooth. This allows portion 146*a* to provide substantial custom filling of emergence portion 110 of void 108 resulting from removal of an upper central incisor 102.

Portion 148*a* may also be shaped to mimic the shape and contour of the natural tooth, although portion 148*a* resides above void 108. The emergence profile is defined by the interface between the subgingival portion 146*a* and exposed portion 148*a*. In some embodiments, exposed portion 148*a* may be omitted, although it may be preferable to include an exposed portion so as to provide a surface that extends somewhat above the gingival tissue around the emergence profile, to better preserve the natural features of the emergence profile gingiva. For example, this provides support structure against which the gingival tissue can be supported and prevented from collapsing, even where the particular person's emergence profile may differ somewhat from the as manufactured subgingival portion 146*a* that approximates a custom fit. In one embodiment, the exposed portion 148*a* does not extend occlusally to the same extent that a normal natural tooth would. For example, occlusal features, including cusp features of the natural tooth may simply be omitted (e.g., the occlusal or top surface of the exposed portion 148*a* may simply be a generally flat surface, with a hole therein where hollow channel 138 intersects the generally flat surface.

In one embodiment, hollow channel 138 of body 132 may be bounded by a cylindrical or other shaped wall, which may or may not extend proximally above exposed portion 148*a*.

At least subgingival portion 146*a* of cuff body 144*a* comprises a sculptable material so that a practitioner can easily remove select areas of portion 146*a*, can add to (i.e., build up) portion 146*a* with a dental material that will adhere (e.g., a curable dental material), or both so that portion 146*a* can be chair-side fully customized to provide an exact, custom fit that fills emergence portion 110 of void 108. Sculptability is advantageous because while the shape and size of the emergence portion 110 of void 108 is more or less the same for different persons for a particular given tooth position (e.g., generally all persons will have very similar emergence portions for their upper central incisors), individual people do vary somewhat from individual to individual, and the ability to easily remove material, add material, or both relative to portion 146*a* allows the practitioner to fully customize portion 146*a* for a given emergence portion 110 of void 108.

Of course, in some embodiments, more than a single size cuff body may be provided for any given tooth position. For example, children may exhibit differently sized emergence portions as compared to adults for a given tooth position. Similarly, some individuals may have particularly large or small teeth, so that their emergence portions may vary somewhat from the normal or average size. As such, in one embodiment, different sizes (e.g., normal adult size, a "large" adult size, a "small" adult size, and/or a child size) may be provided, such that the practitioner may choose the most appropriate size, which may then be fully customized by sculpting. Such differences in sizing can be provided within the casting jigs of the present disclosure. Because the cuff body is sculptable, a practitioner may simply add to or remove material as needed to achieve the desired size.

In one embodiment, subgingival portion 146*a* may intentionally be sized to be slightly larger than the typical average emergence profile, so that the practitioner may shave or otherwise remove portions therefrom (e.g., with a dental burr, scalpel or other suitable tool) immediately prior to placement. This may be advantageous as it may be easier and less time consuming to typically require removal of material rather than supplementation, where material must be added to fully customize the subgingival portion 146*a*. In some embodiments, it may be expected that little or no modification (either removal or adding to) may be required. As such, the size and shape provided is already substantially configured to fill the person's emergence portion 110 of void 108 (with substantially no gaps), providing the same emergence profile as was provided by the natural tooth to thereby support the gingival tissue.

In one embodiment, the subgingival portion 146*a*, and preferably the entire cuff body 144*a* is therefore not formed of metal, but comprises a material that may be easily and conveniently shaved or cut away, as well as added to. Such suitable materials include any of various plastic materials, dental composite materials, or other materials that can be readily customizable through use of a dental burr, scalpel, or other suitable tool. When manufactured with use of the present inventive dental jigs, cuff body 144*a* may be formed from a curable or otherwise settable dental material (e.g., dental composite, etc.) that may be dispensed into the well of the casting jig so as to form the desired cuff body 144*a*. In one embodiment a radiopaque filler may be incorporated into the plastic or composite so that the subgingival structures of the healing cap can be viewed by x-ray or other imaging technique. Such materials also advantageously will readily bond to curable or other suitable adhering dental materials applied thereto where it is desired to add size or adjust contour to the as mass-manufactured cuff body. In one embodiment, the entire elongate body and enlarged cuff body may comprise a single piece of material (e.g., plastic or composite material).

In one embodiment, the exterior surface of cuff body 144a, particularly subgingival portion 146a, may be treated for stimulation of bone or other tissue growth. For example, the material of body 144a or portion 146a may be particularly selected so as to stimulate growth (e.g., a calcium containing material such as hydroxyapatite or similar bone growth promoting material), or the surface may be mechanically (e.g., roughened, smoothed, specific texture patterned), chemically, or otherwise treated to stimulate desired growth. While stimulation of bone growth may be desired, in another embodiment, material selection or treatment may be specifically configured to promote soft tissue growth.

In one embodiment, the distal dental implant insertion end 136 of sculptable anatomical healing cap 130a may include a locking member 150 with a non-circular perimeter configured for insertion into a correspondingly shaped proximal end of a dental implant 114. In the illustrated configuration, the locking member 150 is hexagonal. Other configurations similarly configured to lock against rotation will be readily apparent to one of skill in the art (e.g., triangular, 4-sided, 5-sided, use of non-circular curved sides (e.g., an oval), combination of straight and curved sides, etc.). This locks the healing cap 130a against rotation once inserted within dental implant 114. Any suitable anti-rotation locking mechanism, including those proprietary to various dental implant manufacturers within the art, may be employed. Indeed, as will be explained below, the casting jigs of the present disclosure may provide for the ability to cast such a proprietary shaped locking mechanism as a part of the as manufactured healing cap through use of a corresponding dental implant during casting.

Figures 2A, 2B:
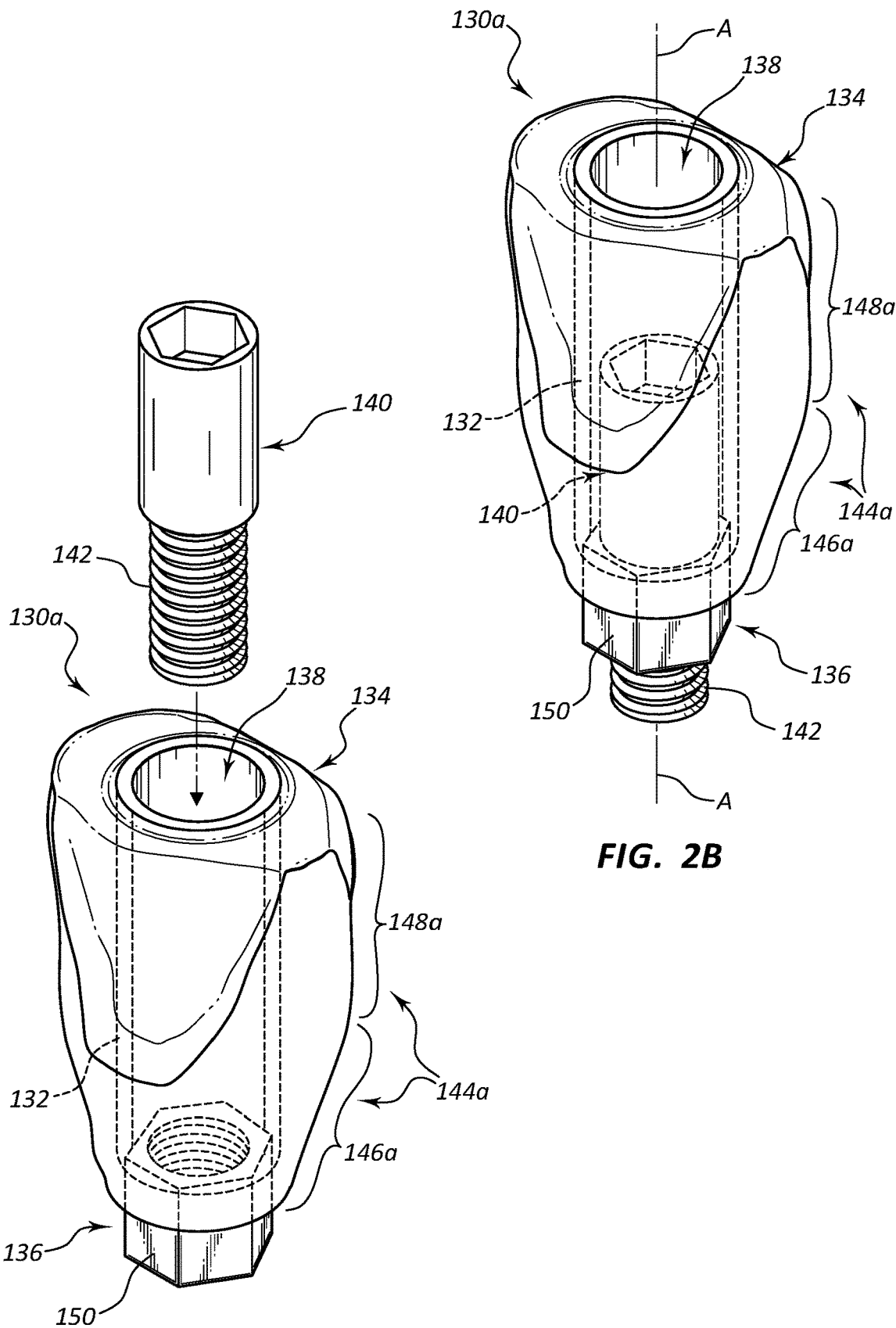
FIG. 2A is an exploded perspective view of an exemplary anatomical healing cap configured for filling the emergence portion of the void formed when an upper central incisor is removed or is missing.
FIG. 2B is an assembled perspective view of the anatomical healing cap of FIG. 2A.
Figure 2F:
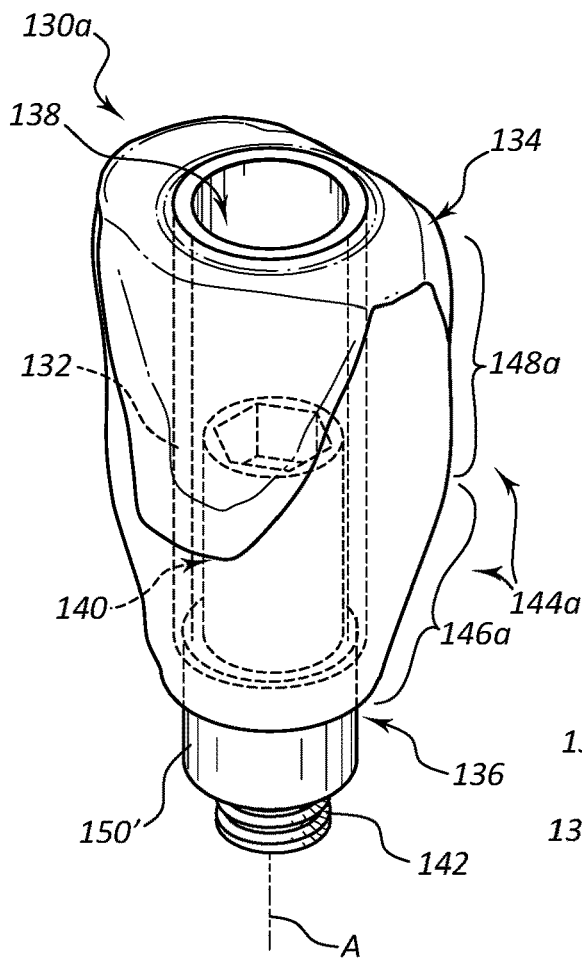
FIG. 2F is a perspective view similar to that of FIG. 2B, but showing an alternative configuration at the distal dental implant end.
Figure 2G:
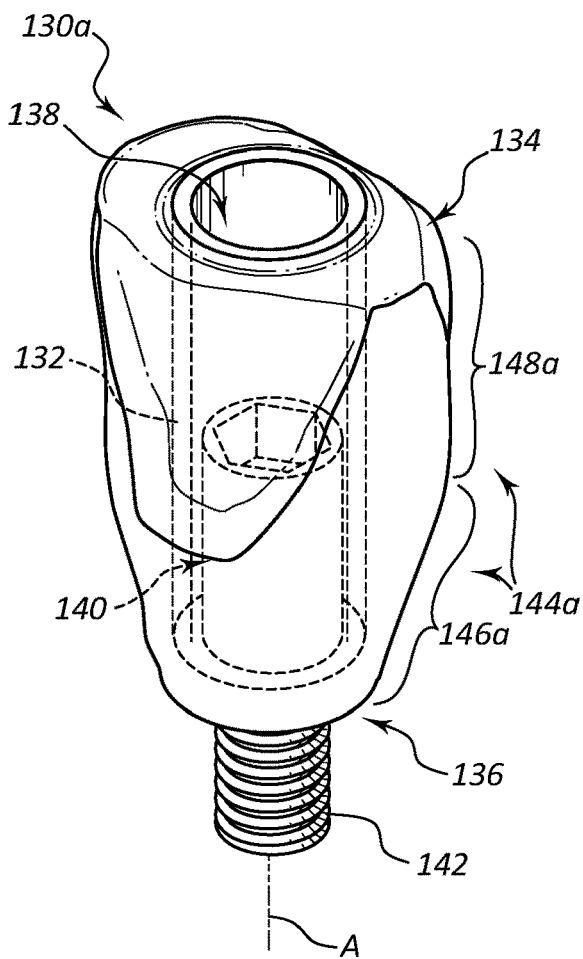
FIG. 2G is a perspective view similar to that of FIG. 2B, but showing another alternative configuration at the distal dental implant end.

In another embodiment, the distal dental implant insertion end 136 may include a circular locking member 150' (see FIG. 2F). In another embodiment, no locking member at all is provided (see FIG. 2G). Any such embodiments may be prepared through use of the inventive casting jigs. In the embodiment of FIG. 2G, external threads 142 are simply coupled into corresponding internal threads of dental implant 114, and the shape of subgingival portion 146a itself can serve to prevent rotation, as this portion is non-circular and engages against the gingival tissue bounding emergence portion 110 of void 108. Other coupling mechanisms between the healing cap and dental implant 114 are possible. For example, the location of internal and external threads may be switched (i.e., internal threads on healing cap, and corresponding external threads on dental implant). Various other suitable coupling mechanisms will be apparent to one of skill in the art in light of the present disclosure.

Figure 2H:
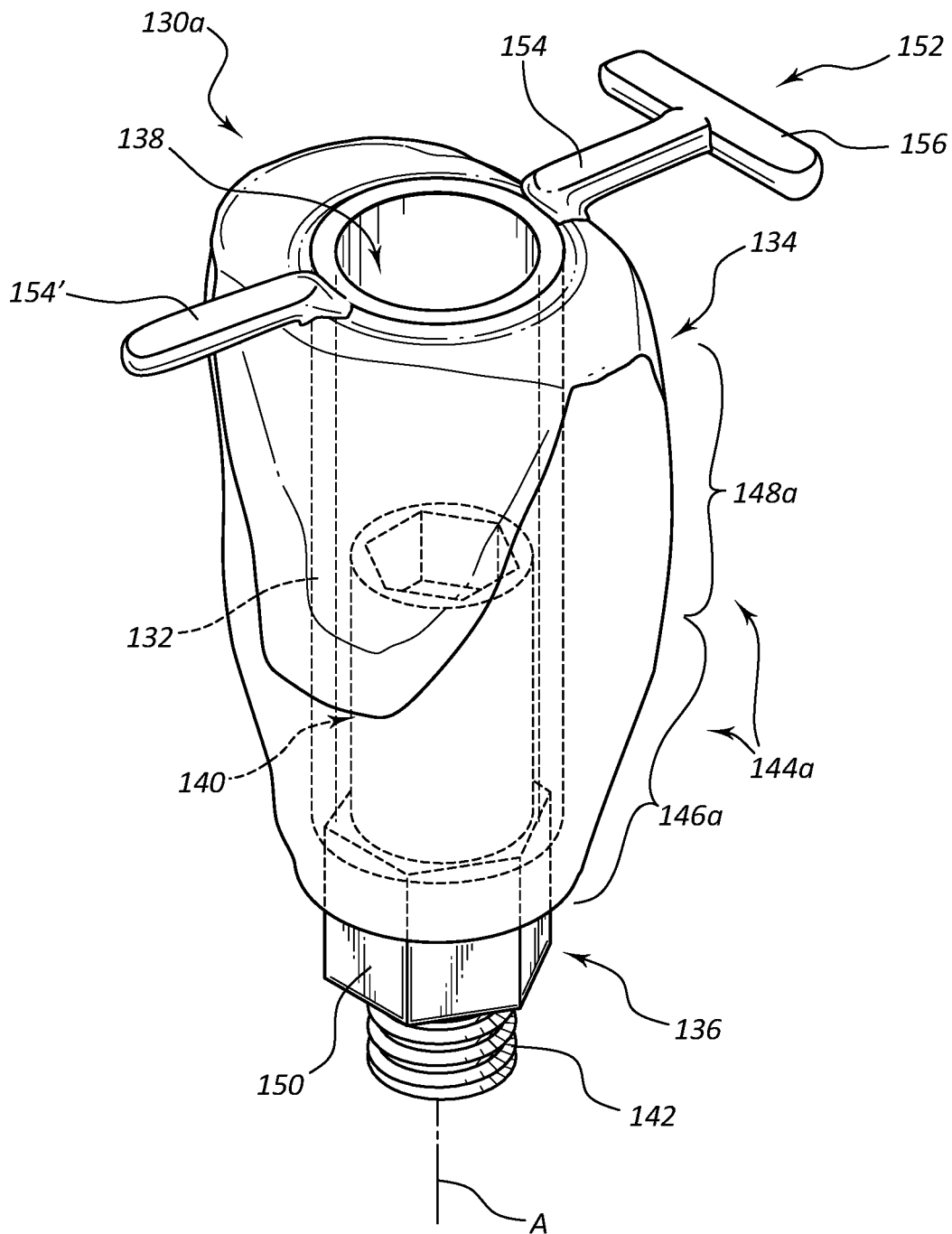
FIG. 2H is a perspective view similar to that of FIG. 2B, but showing an alternative configuration including a removable grippable handle.

In one embodiment, a removable grippable handle may be provided at the proximal end 134 of body 132. As shown in FIG. 2H, a grippable handle 152 may be provided. Handle 152 may include a shaft 154 extending laterally outwards from elongate body 132, cuff body 144a, or both. In one embodiment, shaft 154 may be disposed adjacent the buccal surface of body 132, cuff body 144a, or both, which advantageously orients the handle in the most suitable position during insertion into void 108. As shown, handle 152 may be generally T-shaped, including a cross-bar 156 atop or near end of shaft 154. Another shaft 154' may be provided opposite shaft 154, providing two points disposed laterally outward for easy gripping. Shaft 154, shaft 154' and/or cross-bar 156 provide surfaces that can be easily gripped by dental pliers or another suitable tool available to the practitioner. Shaft 154' and T-shaped handle 152 may be cast in the inventive casting jig by simply providing these extensions at a top surface of the well used in forming the cuff body, as will be shown and described below in conjunction with FIG. 5. Once the healing cap is placed within void 108, handle 152 (including shaft 154') may be removed (e.g., cut away).

While the illustrated configuration is shown with cuff body 144a generally aligned with axis A of channel 138, in another embodiment, the axis A of channel 138 may be offset relative to an axis of cuff body 144a. Similarly, cuff body 144a may not be "on center" relative to axis A of threaded portion 142. This may be beneficial where the natural tooth (and thus void 108) is mis-aligned relative to what would be "normal". Such configurations allow the practitioner to account for such situations.

It will be understood that anatomical healing caps may also be provided for other tooth positions, such as upper lateral incisors, upper cuspids, upper bicuspids, upper molars, lower incisors, lower cuspids, lower bicuspids, and lower molars. It will be apparent that a single configuration may sometimes be suitable for two or more different tooth positions (e.g., a single bicuspid configuration may be used for both first and second bicuspids, a single molar configuration may be used for both first and second molars, a single lower incisor configuration may be used for all lower incisors, etc.). Additional details of the anatomical healing caps are disclosed in U.S. patent application Ser. No. 13/347,127 filed Jan. 10, 2012 and entitled CUSTOMIZABLE SCULPTABLE ANATOMICAL HEALING CAPS, SYSTEMS, AND RELATED METHODS, already incorporated by reference in its entirety.

Figures 3A, 3B:
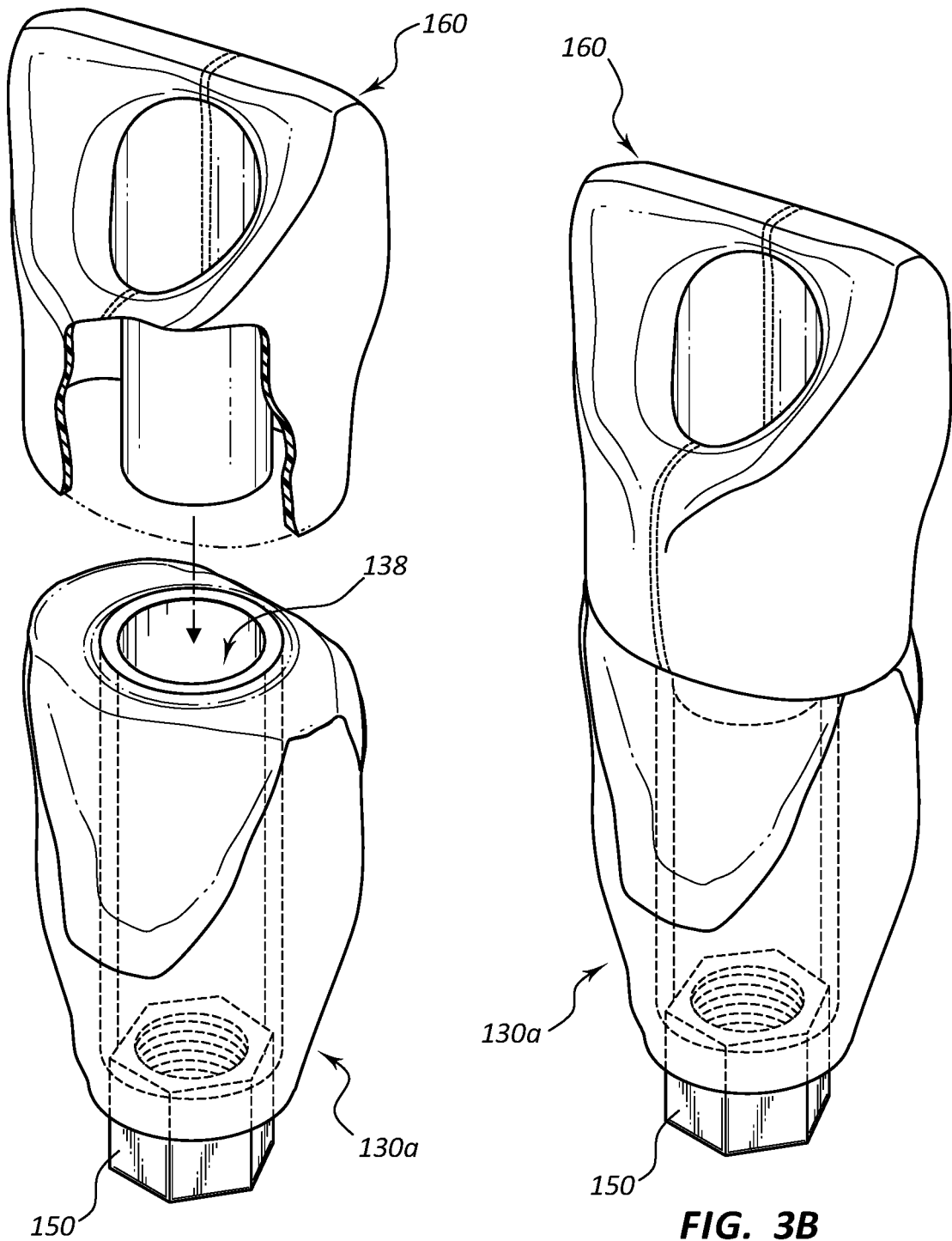
FIG. 3A is an exploded perspective view showing a related system including an anatomical healing cap and an associated temporary crown form.
FIG. 3B is a perspective view showing the system of FIG. 3A with the temporary crown form coupled over the anatomical healing cap.

FIGS. 3A-3B illustrate healing cap 130a of FIG. 2B in combination with a temporary crown form 160 that may be used with the healing cap in chair-side manufacture and placement of a temporary provisional crown or other prosthesis.

FIGS. 1A-1E discussed above show the same steps to be taken when installing the anatomical healing caps. As shown in FIGS. 1A-1E, the tooth is removed, the void 108 is prepared to receive dental implant 114, and dental implant 114 is anchored into the underlying bony tissue of the jaw bone. Rather than installing the cylindrical state of the art healing cap or cuff shown in FIG. 1F, the appropriate sculptable anatomical healing cap is selected (e.g., healing cap 130a configured for filling the emergence portion 110 of void 108 of an upper central incisor).

Figure 4A:
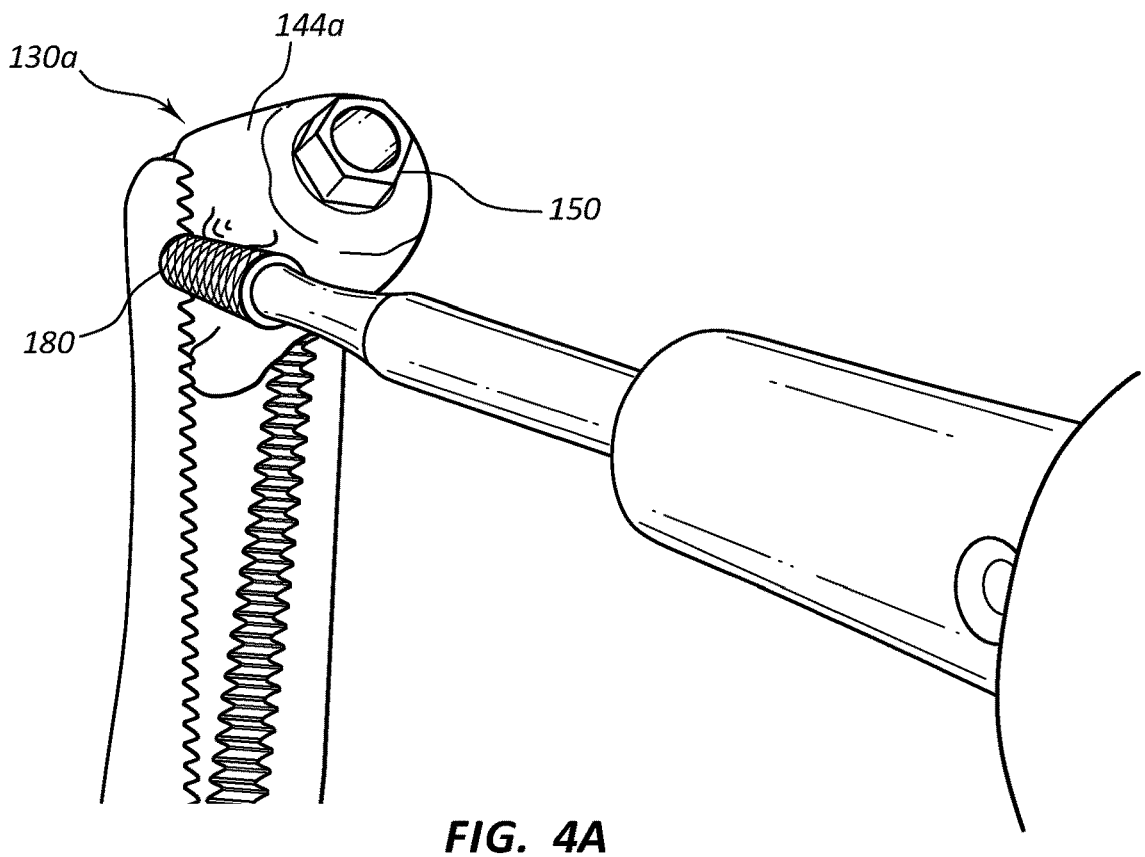
FIG. 4A is a perspective view showing a portion of the cuff body of the healing cap being customized by removal with a dental burr.
Figure 4B:
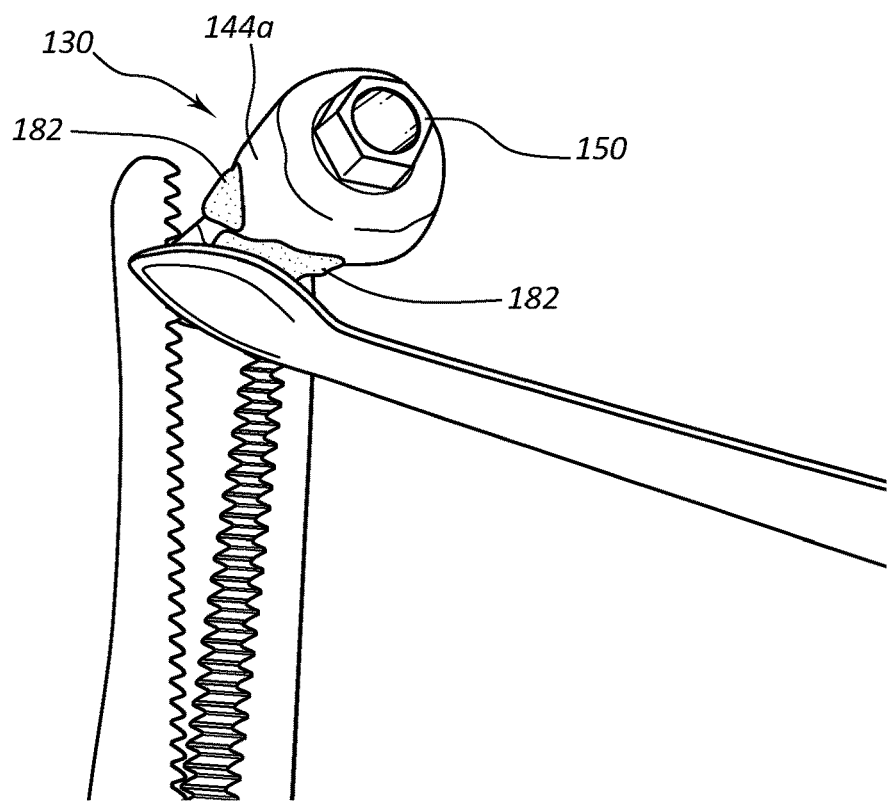
FIG. 4B is a perspective view showing the cuff body being customized by building up with application of a dental material.

The as manufactured shape and contours, which are a very close fit to the actual emergence portion 110 and emergence profile of the void 110 and tooth 102, may be custom modified as shown in FIG. 4A by removing select portions of cuff body 144a (particularly subgingival portion 146a) with a dental burr 180 or other suitable tool. As shown in FIG. 4B, if necessary, the practitioner may build up portions of cuff body 144a (particularly subgingival portion 146a) by applying and curing a dental material (e.g., light-curable, chemically-curable, heat curable, or other adhering dental material) 182. This is possible because at least the subgingival portion 146a of cuff body 144a is formed of a curable or otherwise settable material that is easily removed with the aid of a dental burr 180 or similar tool. Similarly, the material of body 144a strongly bonds to curable material 182, should such additions be desired. For example, one may employ the same curable or otherwise settable dental material employed in casting the cuff body 144a in the casting jig to add material, if desired. By removing material, adding material, or both, the practitioner is advantageously able to relatively quickly customize at least the subgingival portion 146a of the cuff body 144a so that it provides a perfect or near perfect fit, filling the emergence portion 110 of void 108, with substantially no gaps.

Figure 4C:
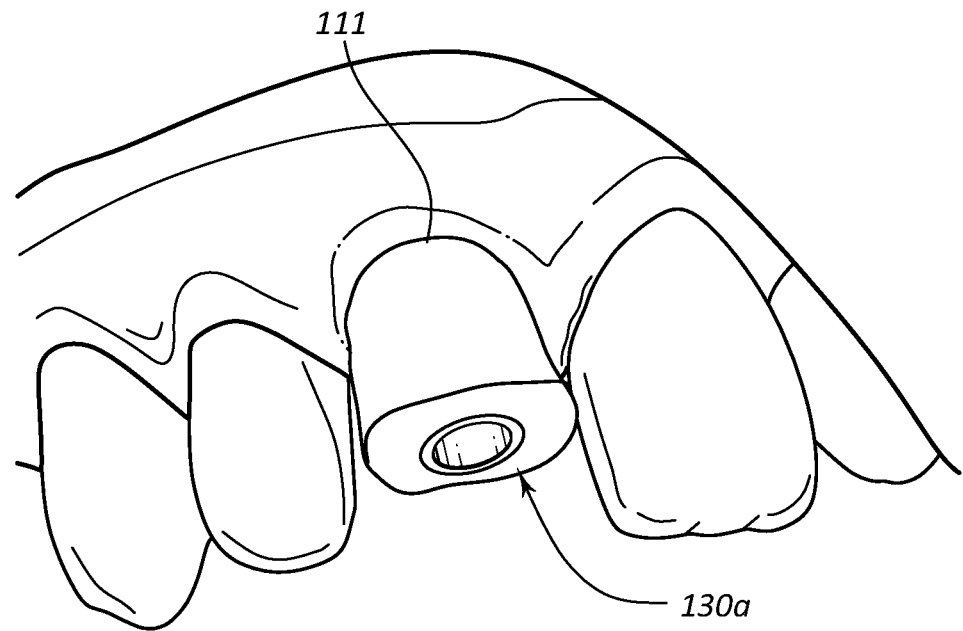
FIG. 4C is a perspective view of the arch of FIG. 1E in which an anatomical healing cap has been coupled into the implant, leaving no gap between the cuff body of the healing cap and the gingival tissue surrounding the emergence portion of the void.

As shown in FIG. 4C, the healing cap 130a is placed within void 108 so that subgingival portion 146a fills the emergence portion 110 with substantially no gaps, and provides an emergence profile between the gingival tissue emergence portion 110 that is substantially identical to that provided by the natural tooth prior to its removal. The exposed portion 148a resides just above the gingival tissue, which is helpful in ensuring that all gingival tissue is fully supported, particularly where there may be some small degree of variability in the contours of this gingival tissue between one patient and another for a given tooth position.

Figure 4D:
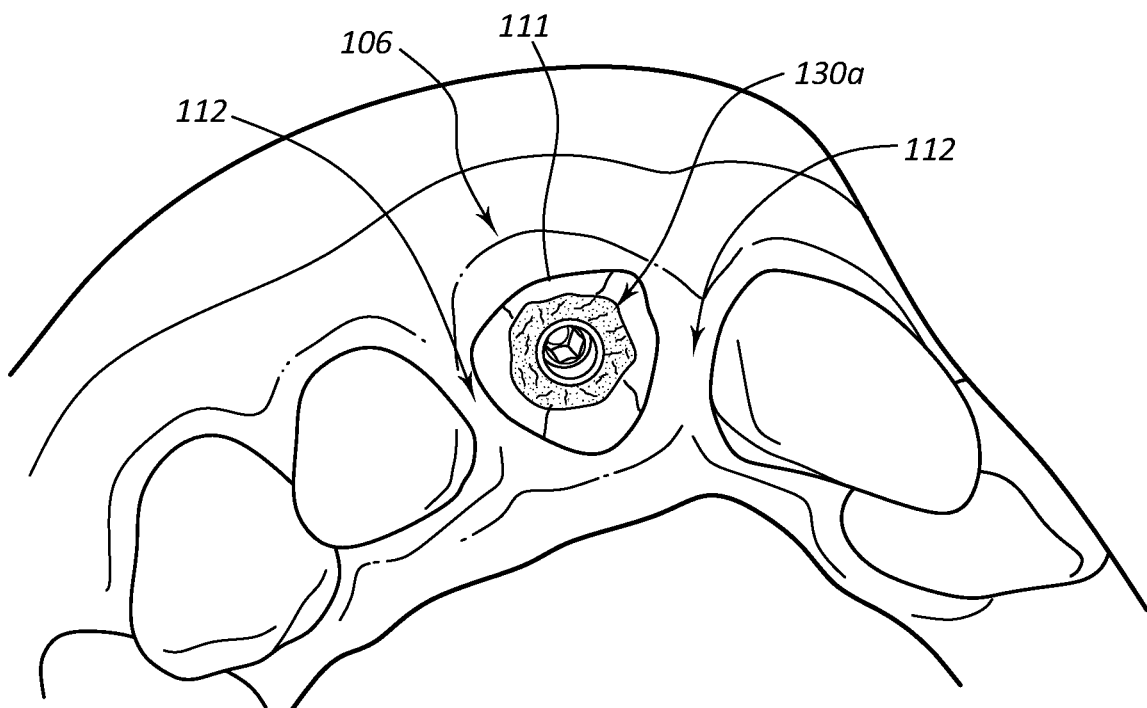
FIG. 4D is another perspective view of the arch of FIG. 4C.

FIG. 4D shows the exposed portion 148a having been completely removed (e.g., it may be easily cut away with a burr or other convenient dental tools if desired). This view perhaps best shows how the emergence profile 111 surrounding the location where the healing cap 130a emerges from the void 108 is perfectly or nearly perfectly matched to the gingival tissue so that substantially no gaps are present (compare with the gaps that are common with state of the art healing caps shown in FIG. 1F). Because subgingival portion 146a is provided with the anatomical shape of the emergence portion 110 of void 108, the various characteristic features of gingival cuff 104 are preserved, including preservation of the full height of contour of gingival cuff 104, the interdental papilla 112, and the buccal prominence 106.

Figure 4E:
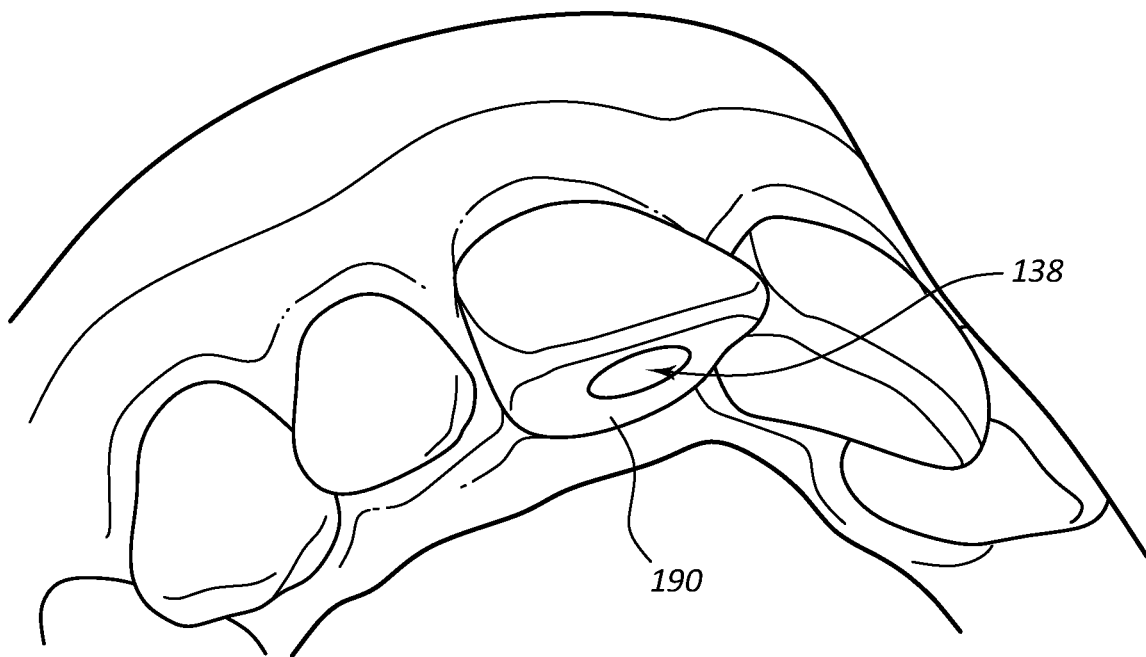
FIG. 4E is another perspective view of the arch of FIG. 4C in which a temporary crown has been formed over the healing cap.

As shown in FIG. 4E, a temporary or provisional crown 190 may be chair-side formed over the sculptable anatomical healing cap 130a, while preserving access to underlying hollow channel 138 of healing cap 130a.

When a permanent crown (typically custom prepared in an off-site dental lab) is ready for installation, the healing cap (and any temporary crown formed thereon) may simply be removed from void 108 by accessing coupling screw member 140 through hollow channel 138. The permanent crown may then be inserted within void 108, taking the place of healing cap 130a. Of course, the permanent crown may be provided with the necessary shape to fill emergence portion 110, so that the gingival tissue surrounding void 108 which has been preserved through the use of sculptable anatomical healing cap 130a can continue to be preserved.

The use of the anatomical sculptable healing cap provides for the preservation of various gingival features that are characteristic of natural teeth, including the gingival cuff, height of contour, the emergence profile, the interdental papilla, and the buccal prominence. These features are typically progressively lost over the weeks and/or months following first stage treatment where insufficient structure is provided for supporting the gingival tissue at the site where the tooth once was. Use of the healing caps, systems, and methods allow these features to be maintained, rather than progressively lost following first stage treatment and before placement of a custom permanent crown.

III. Exemplary Casting Jigs

Figure 5:
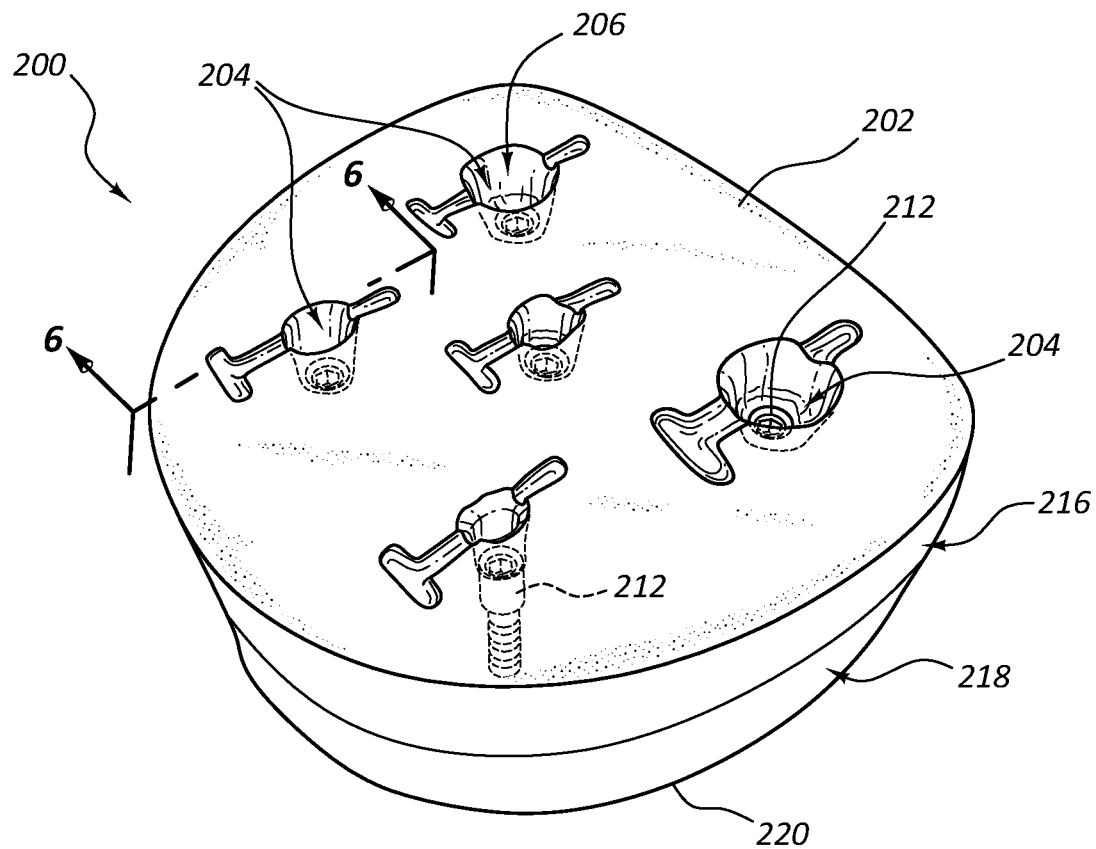
FIG. 5 is a perspective view of an exemplary casting jig for manufacturing anatomical healing caps.
Figure 6:
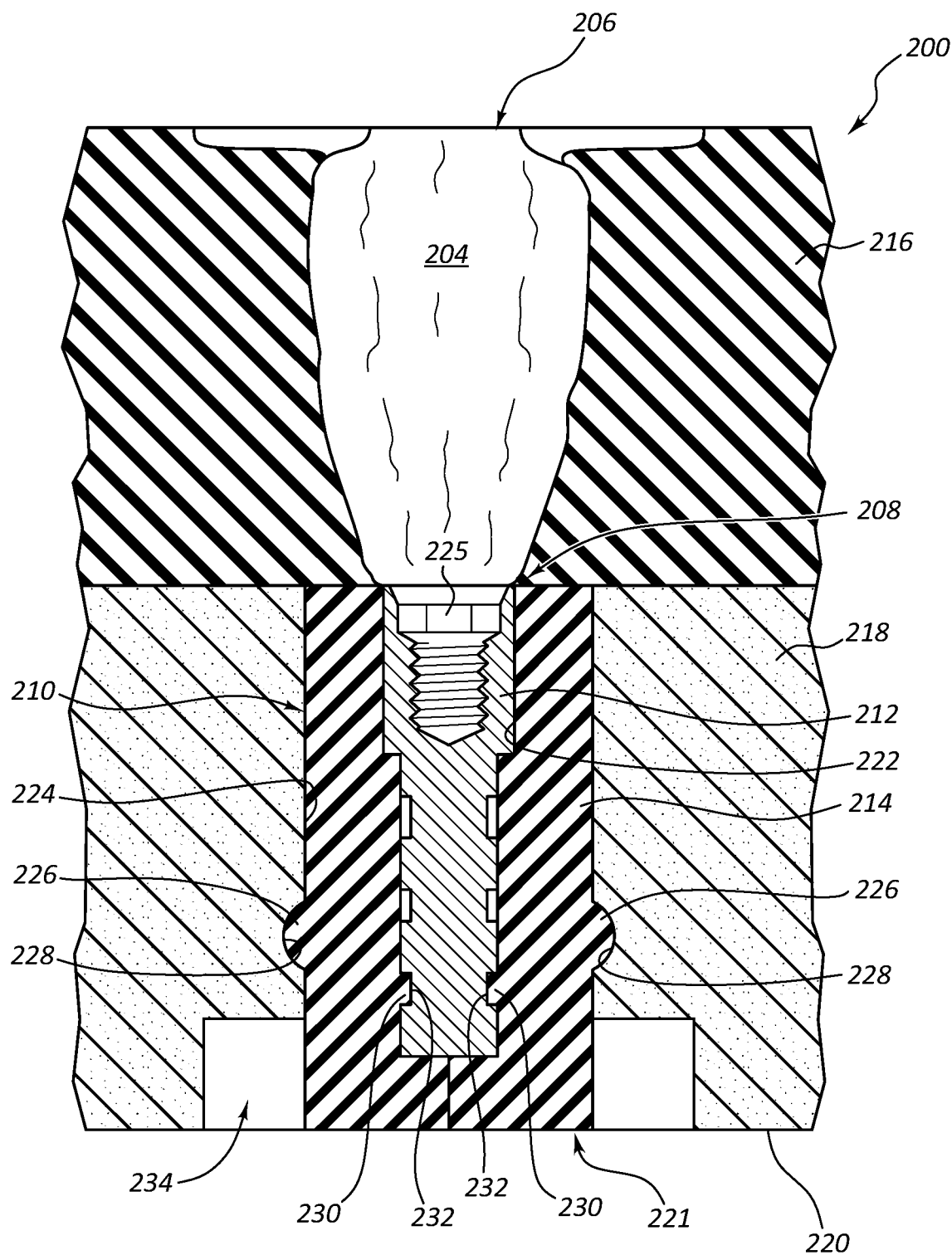
FIG. 6 is a cross-sectional view through the casting jig of FIG. 5.

FIG. 5 shows an exemplary casting jig 200 for use in manufacture of the customizable sculptable anatomical healing caps. Casting jig 200 includes body 202, which includes one or more wells 204 formed therein. Each well 204 is open at a proximal end 206 and may include a socket 210 at a distal end 208 (FIG. 6). Open proximal end 206 allows introduction of a curable or otherwise settable dental material from which an anatomical healing cuff body (e.g., body 144a) is formed. Distal end 208 may include a socket 210, which allows a dental implant or dental implant analog 212 to be releasably received therein. Each well 204 includes a negative shape corresponding to an anatomical healing cuff body of a given tooth position. As described above relative to the anatomical healing caps and cuff bodies, each such corresponding negative shape has an asymmetrical cross-section and an irregular surface so that an anatomical healing cuff body having said shape (and formed by filling said well with a curable or otherwise settable dental material) is configured to provide substantially custom filling of at least an emergence portion of a void where a natural tooth once emerged from a void or where a tooth would have emerged from a void.

Casting jig 200 is shown as including a plurality of wells, each differently configured. For example, one or more wells may be configured to produce healing caps configured for molar placement, one or more may be configured to produce healing caps configured for bicuspid placement, one or more may be configured to produce healing caps configured for cuspid placement, one or more may be configured for upper lateral incisor placement, one or more may be configured for upper central incisor placement. Similarly, wells may be configured to produce healing caps specifically configured for placement in the various lower tooth positions. By way of example, one casting jig may include all the needed wells for producing all of the upper tooth positions, while a separate casting jig may be provided for producing all of the lower tooth positions. In another embodiment, all positions may be provided within a single casting jig. In another embodiment, only a single well may be provided in a casting jig, specific to tooth configuration. Thus, it will be readily apparent that any number and configuration of wells may be provided within the inventive casting jigs.

While FIG. 6 shows an embodiment in which well 204 is vertically aligned over implant or implant analog 212, this is not required. For example, in some embodiments, a longitudinal axis of healing cuff body 144a (and thus well 204) may be off center and/or out of axial alignment relative to the longitudinal axis of implant or implant analog 212. Such off center or out of axial alignment configurations may be desirable where teeth are crowded, or where space for anchor placement is otherwise not optimal (e.g., where the void for implant placement is not axially aligned and centered below the healing cap to be placed). Such configurations provide flexibility in void preparation and implant placement to the practitioner.

As seen in FIG. 6, implant or implant analog 212 may be retained within socket 210 in the desired position and orientation relative to well 204 by an implant housing 214 that serves as a cage, holding implant or implant analog 212 in place. As perhaps best seen in FIG. 6, casting jig 200 may include an upper portion 216 and a lower portion 218. Upper portion 216, which defines at least a portion of well 204, may be formed of any suitable material (e.g., plastic, metal, stone, an elastomeric material, etc.). In one embodiment, upper portion 216 is formed of an elastomeric material (e.g., rubber, silicone, etc.) so as to provide upper portion 216 adjacent well 204 with the ability to "give", facilitating easier removal of a cast healing cap (e.g., cap 130a). In another embodiment, upper portion may comprise a more rigid material (e.g., rigid plastic, stone, metal, etc.). Use of an elastomeric material may facilitate easier removal of cast healing caps from wells 204, and may also prevent or otherwise minimize any tendency of upper portion 216 adjacent wells 204 to chip or crack, which might otherwise tend to occur with some materials (e.g., stone).

Lower portion 218 may be formed of the same or a different material as compared to upper portion 216. In one embodiment, lower portion 218 may comprise a material that is more rigid than upper portion 216. For example, lower portion 218 may comprise stone, metal, or a rigid plastic, while upper portion 216 may comprise an elastomeric material.

Another embodiment may not necessarily include discrete upper and lower portions formed of different materials, but may include an elastomeric material surrounding wells 204 (although the entire upper portion 216 may not be formed of the elastomeric material). In other words, portions of casting jig 200 adjacent to wells 204 (and defining the bounds of wells 204) may comprise an elastomeric material, while other portions of casting jig 200 may be formed of a more rigid material. In one such embodiment, the elastomeric material may be surrounded by the more rigid material.

Implant housing 214 advantageously holds implant or implant analog 212 in a desired position and orientation relative to distal end 208 of well 204. Implant housing 214 may also advantageously allow removal and interchange of one implant or implant analog 212 with another implant or implant analog. For example, there exist scores of dental implant manufacturers, each often including proprietary structural features (e.g., proprietary locking recess shapes). In addition, where a healing cap is to be seated within and coupled to a given implant, the healing cap should preferably have corresponding shaped locking structure to correspond to that of the implant. For this reason, one typically purchases implants and healing caps from the same manufacturer so that they are compatible with one another. Because the present casting jigs allow a practitioner to manufacturer their own anatomical healing caps, it would be advantageous to provide a mechanism by which the anatomical healing caps may be manufactured so as to be compatible with a desired manufacturer implant to be employed. Use of the manufacturer's implant or implant analog in socket 210 of casting jig 200 provides the produced healing cap with the desired corresponding locking structure (e.g., locking structure 150 of FIG. 2A).

Implant housing 214 allows one to remove implant or implant analog 212 through an opening 221 in bottom surface 220 of casting jig 200, after which an implant or implant analog of another manufacturer may be inserted into socket 210, housed within implant housing 214. Thus, the practitioner or other user of casting jig 200 is free to employ whichever implant or implant analog manufacturer he or she desires. Placement of the desired implant or implant analog 212 within socket 210 allows one to cast the produced healing cap so as to include the desired locking structure that corresponds to locking recess 225 of implant or implant analog 212.

Separate, specifically configured implant housings may be provided for each implant. For example, the exterior surface and profile of each implant or implant analog 212 may differ from manufacturer to manufacturer. Thus, a different implant housing may be provided for each manufacturer's implants and implant analogs. Different, specifically configured implant housings 214 may be provided to correspond to each implant or implant analog. For example, an interior profile 222 of a given implant housing 214 may be specifically configured to mate with or otherwise retain the corresponding implant or implant analog 212. The exterior profile 224 of all implant housings 214 may be identical, allowing any of the implant housings to be inserted into socket 210, for use within casting jig 200 for a desired tooth position. Thus, the system allows one to employ any of dozens of various implant or implant analog configurations (e.g., all configured for use with a given tooth position) within the socket adjacent the well configured to produce a healing cap for that given tooth position.

In another embodiment, implant housing 214 may be suitable for use across multiple differently configured implants or implant analogs 212. For example, where implant housing 214 is formed of an elastomeric material, so long as the various implants or implant analogs include roughly similar sizing, the elastomeric deformation ability of the implant housing 214 may allow housing 214 to deform to accept and appropriately "cage" similar, but differently configured implants or implant analogs 212.

The configuration of casting jig 200 thus provides great flexibility in allowing the practitioner to manufacture anatomical healing caps for use with any desired dental implant. All that is required is that the user insert the desired implant or implant analog 212 into socket 210 (with accompanying housing 214), and the formed anatomical healing cap will automatically include the necessary structural features so as to allow its use with that particular implant.

Stated another way, while currently a practitioner is required to purchase healing caps from a manufacturer for perhaps as much as $40 to $80 each, the casting jig allows one to make their own healing caps, reducing the cost of components to be purchased. In addition, the practitioner manufactured anatomical healing caps provide vastly improved results with respect to preservation of the desirable aesthetic gingival features as compared to existing healing caps. All this is possible at substantially reduced cost. For example, a practitioner may make his or her own anatomical healing cap for significantly reduced cost as compared to the large purchase price of an inferior state of the art healing cap.

For example, implants typically include an anti-rotational locking recessed connection 225 (e.g., a hex recess) in the head of dental implant or implant analog 212. No matter the specific configuration of such a proprietary locking recess of a given implant or implant analog, the produced healing cap can be formed so as to include the corresponding mating feature as a result of the locking recess of the implant or implant analog being used to close the distal end of well 204 during casting. In other words, the shape defined by locking recess connection 225 can be cast into the distal end of the manufactured healing cap. By way of example, if a given dental implant or implant analog 212 includes a hex recess (e.g., recessed connection 225), the formed anatomical healing cap will include the corresponding hex locking member 150 (see FIG. 2A) at its distal end, as a result of the curable or otherwise settable material being introduced into the hex recess 225 of the implant as well as the adjacent well 204, disposed thereabove. As will be described below, insertion of an elongate body (e.g., a wrench, a Q-tip, a hollow straw or other suitable tool) can be used to form and preserve a hollow access channel 138 through the practitioner manufactured healing cap to allow subsequent coupling of the produced healing cap to a dental implant with a screw 140.

Figure 7:
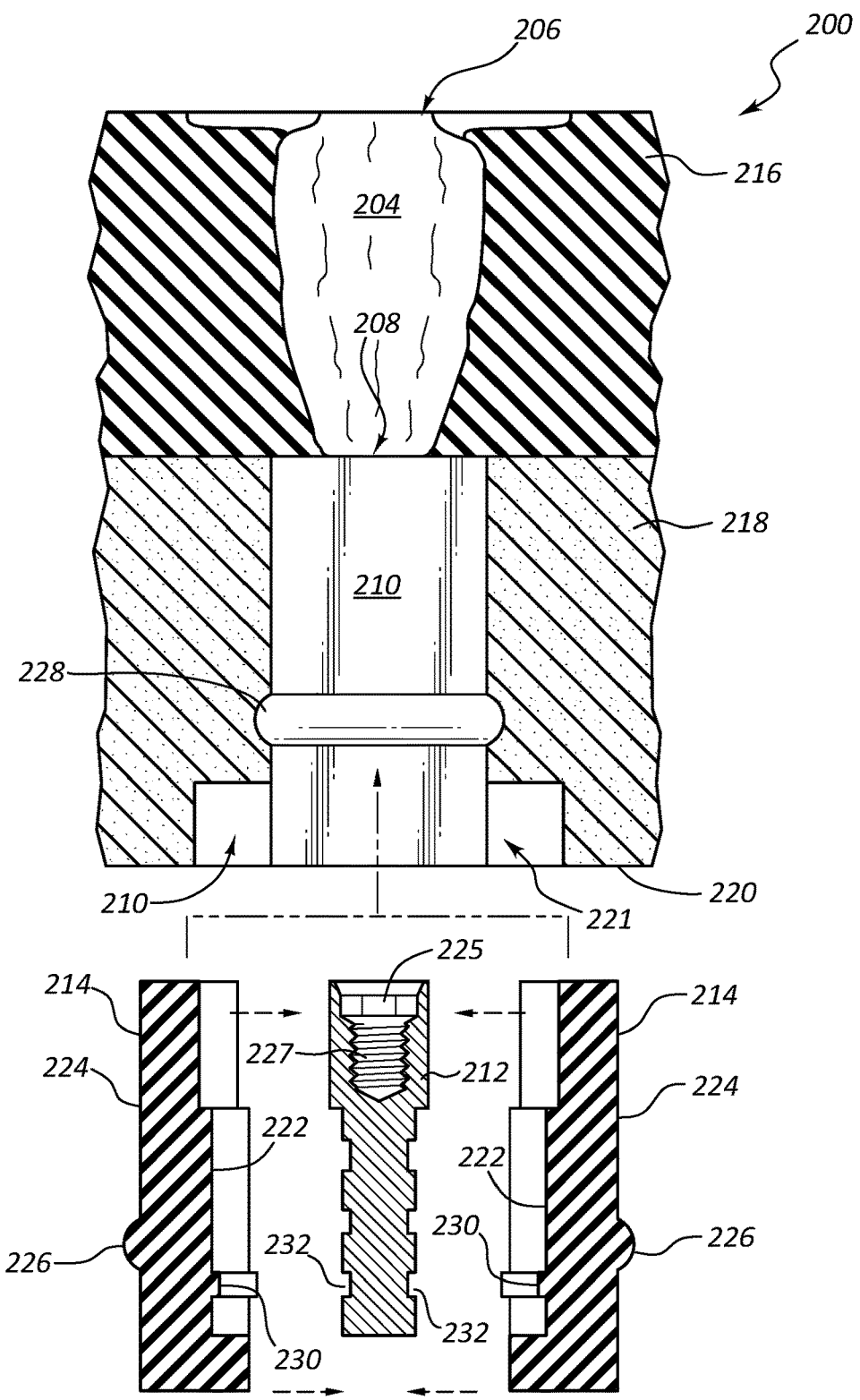
FIG. 7 is a cross-sectional view similar to FIG. 6, but in which the dental implant analog and the implant housing have been removed from the socket below the well of the casting jig.

While shown with implant housing 214, it will be understood that in some embodiments, implant or implant analog 212 may be directly retained by the exterior walls and any retaining features (e.g., a snap fit, etc.) of socket 210. In another embodiment, retention of dental implant or dental implant analog 212 by socket 210 is indirect, (e.g., through implant housing 214), as described above in conjunction with FIGS. 6-7. Other retention mechanisms may alternatively be employed to releasably retain dental implant or implant analog 212 within socket 210, and such mechanisms are within the scope of the present disclosure.

For example, in one embodiment, the socket may include an elastomeric lining, so as to allow one to simply press a desired implant or implant analog 212 through opening 221 in bottom surface 220 up into position relative to well 204. Such a configuration may appear similar to that shown in FIG. 6, but in which implant housing 214 is glued or otherwise fixedly retained within socket 210. The bottom portion of housing 214 shown closed in FIG. 6 (where the two halves of housing 214 come together) might be open, allowing one to insert therein a desired implant or implant analog 212. The elastomeric nature of such a lining or housing may hold the implant or implant analog 212 in place during casting.

Housing 214 may include a projection (e.g., an annular ring) 226 that snap fits within a corresponding annular groove 228 formed within socket 210 in lower portion 218. Other retention mechanisms for retaining housing 214 within socket 210 will be apparent to one of skill in the art. In a similar manner, interior surface 222 of housing 214 may include a projection 230 configured to snap fit within a corresponding annular groove 232 formed within implant or implant analog 212. Where housing 214 comprises an elastomeric material, no specific coupling structure (e.g., projection 230 and corresponding groove 232) may be required, as the elastomeric characteristics of housing 214 may be sufficient to grip and hold the exterior surface of implant or implant analog 212 in place, particularly once the assembly (implant analog 212 and housing 214) is inserted into socket 210. Similarly, such gripping characteristics of implant housing 214 or of adjacent lower portion 218 may be sufficient to hold implant housing 214 and implant or implant analog 212 within socket 210 by friction fit, so that no annular ring 226 or corresponding groove 228 may be present.

Housing 214 may include a handle adjacent bottom surface 220 or other means to facilitate gripping and removal of housing 214 from socket 210. For example, in the illustrated configuration, socket 210 widens adjacent bottom surface 220 at 234, allowing one to grip the exterior sides 224 of housing 214 and pull it out of socket 210. Such an embodiment may advantageously preserve the ability of casting jig 200 to lay flat (e.g., bottom surface 220), without any handles extending beyond bottom surface 220. Another embodiment may include one or more grippable handles on a bottom surface of housing 214, which handles may be recessed within socket 210, so as to preserve the ability of the casting jig to lay flat.

Figure 8:
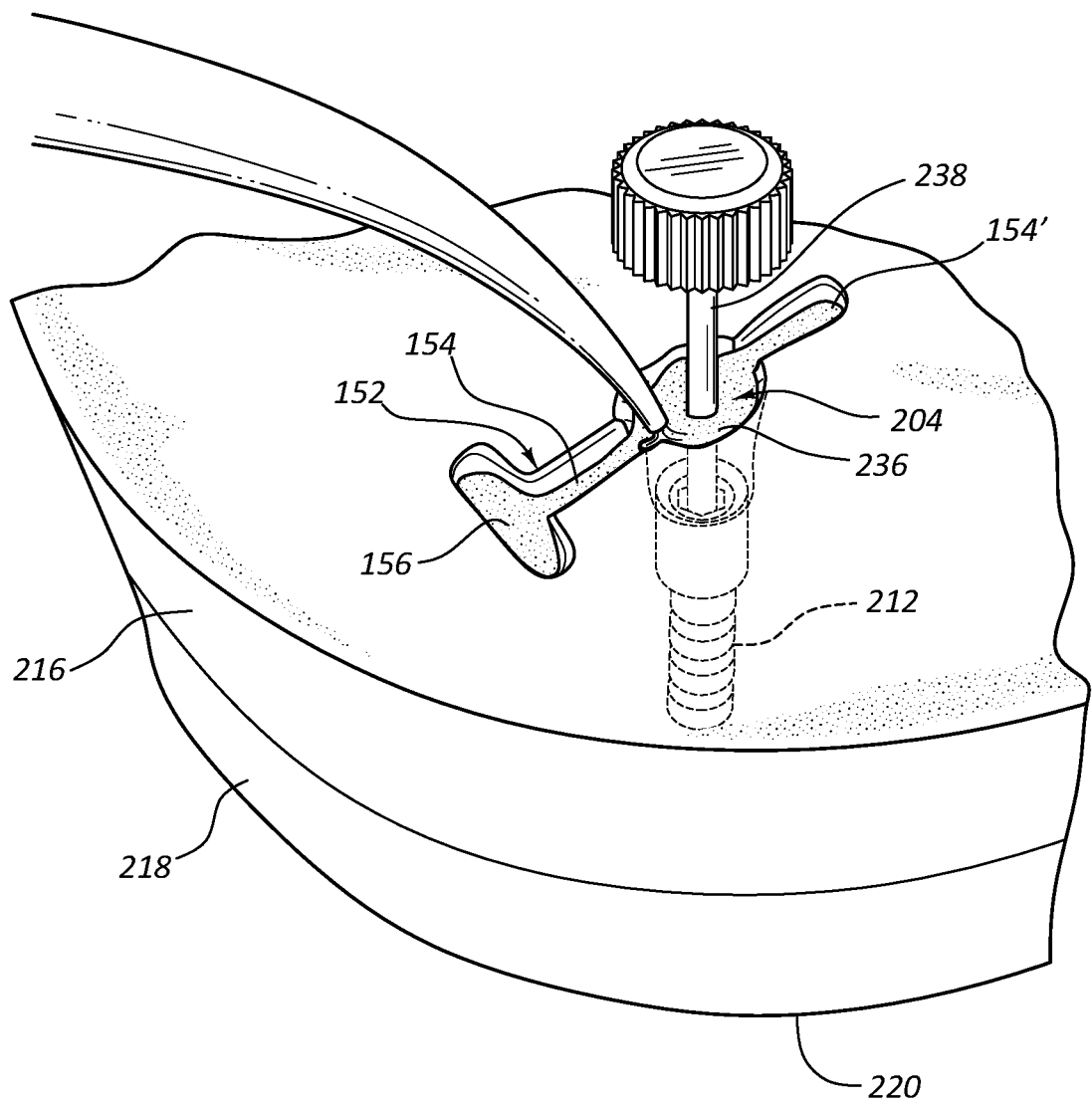
FIG. 8 is a perspective view showing positioning of an elongate body (e.g., a straw, an implant wrench, a temporary abutment, etc.) into the recessed connection of the implant or implant analog and introduction of the curable or otherwise settable material around the elongate body so as to form an anatomical healing cuff body while preserving access through the cuff body to the implant or implant analog.
Figure 9A:
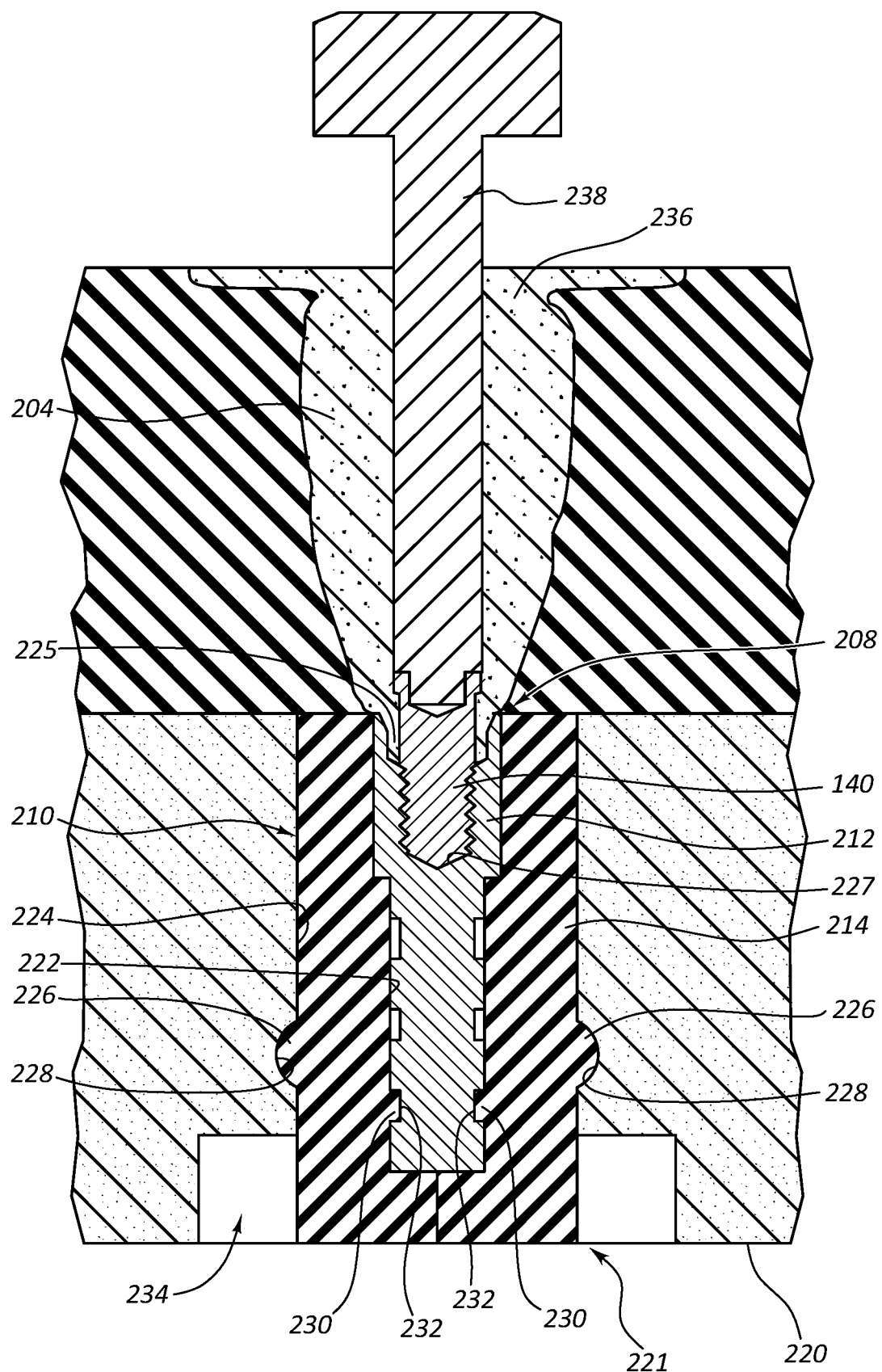
FIG. 9A is a cross-sectional view through the casting jig of FIG. 8 as the anatomical healing cap is being formed.
Figure 9B:
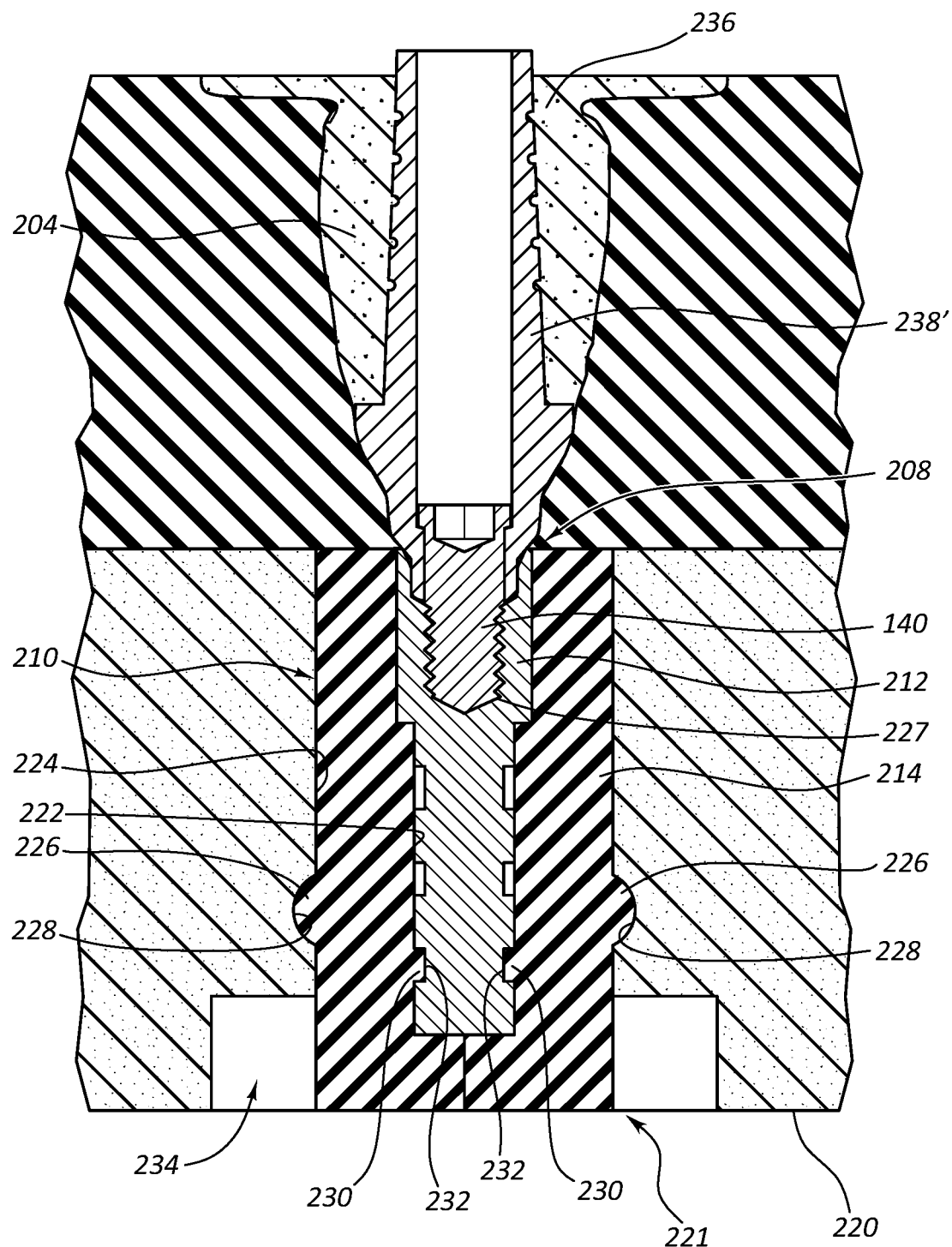
FIG. 9B is a cross-sectional view through the casting jig of FIG. 8 in which a temporary abutment is used as a core around which the anatomical healing cap is being formed.
Figure 10:
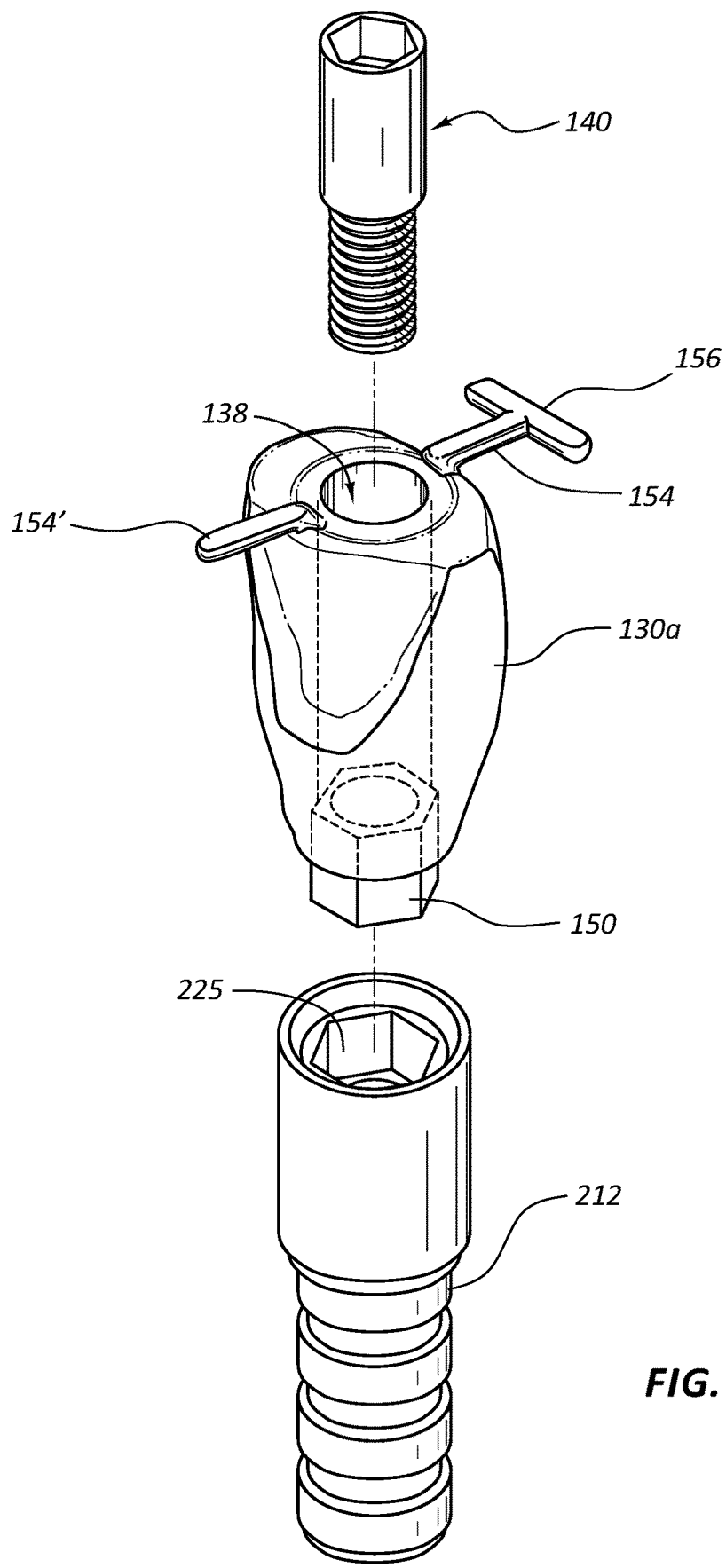
FIG. 10 is an exploded perspective view of the anatomical healing cap manufactured using the casting jig next to the associated implant analog.
Figure 11:
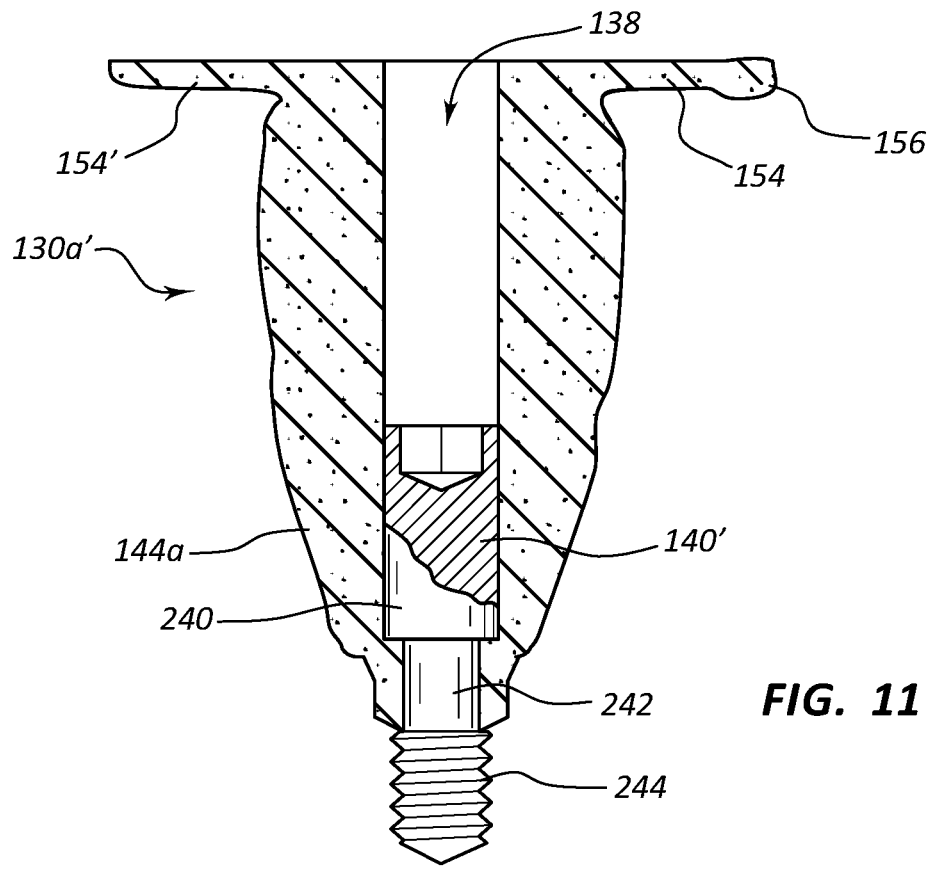
FIG. 11 is a view of an anatomical healing cap formed using the casting jig and a coupling screw as the elongate body.

FIGS. 8-9A illustrate introduction of curable or otherwise settable dental material 236 into well 204. Prior to introduction of flowable dental material 236 into well 204, an elongate body (e.g., wrench 238) may be inserted into screw 140, which prevents flowable dental material 236 from filling threaded portion 227 of implant or implant analog 212. In another embodiment, where no screw is present, the elongate body may be directly inserted into threaded portion 227. For example, elongate body 238 may have a diameter or thickness adjacent its distal end that is sized so as to cover or plug threaded portion 227, while not being so large in diameter or thickness to cover or plug the entirety of recessed connection 225. In either case, as perhaps best seen in FIG. 9A, flowable dental material 236 may be allowed to enter recessed connection 225 so that the produced healing cap includes a hexagonal locking member 150 (or other anti-rotational shape), but in which the central portion of the locking member 150 is hollow, preserving hollow access channel 138 therethrough. FIG. 10 shows a produced healing cap 130a, in exploded view with coupling screw 140 and implant analog 212. Where a screw is present, the screw may actually become integral with the healing cap, so that it cannot be later removed (e.g., similar to as shown in FIG. 11). Once material 236 is cured, backing out of screw 140 with wrench 238 may serve to unseat healing cap 130a from well 204.

While the method is illustrated in FIG. 9A with elongate body 238 comprising an implant wrench, it will be understood that other elongate bodies may be alternatively employed. For example, even a Q-tip, an appropriately dimensioned hollow straw, or solid rod may be inserted to achieve a similar result. Where a wrench or other solid elongate member is employed, it may be important that the cured or set dental material 236 not adhere strongly to wrench 238 to allow its removal. Where a hollow straw is employed, removal of the straw may not be required. Once the wrench or other elongate body 238 has been removed, one may employ a dental burr or similar tool to widen central access channel 138, if desired. In another embodiment, one may place a removable collar about elongate body 238 prior to filling well 204, which collar can be removed with elongate body 238 after curing or setting, similarly resulting in a wider central channel 138.

In one embodiment, the elongate body inserted into well 204 may comprise a temporary abutment 238' purchased from a dental product manufacturer (e.g., the same manufacturer who provided the implant or implant analog). Such a temporary abutment may be configured similar to body 132 shown in FIGS. 2A-2E. Such an embodiment is shown in FIG. 9B. The abutment 238' may already include any needed locking structure (e.g., hex head 150) corresponding to recess 225. Thus, in such a case, the introduced curable or otherwise settable dental material 236 need not enter into recess 225 (which recess may conveniently be entirely blocked by corresponding locking structure already disposed on temporary abutment 238', and seated within recess 225 implant or implant analog 212).

In other words, temporary abutment 238' may be used as a core around which the anatomical healing cuff body 144a is cast within well 204. The abutment 238' may be coupled to implant 212 by screw 140. In another embodiment, no screw may be employed. Where screw 140 is present, the screw may be removed through channel 138. Thus, in this embodiment, screw 140 may not become bonded and integral with cured or set dental material 236 of the anatomical healing cap. Use of a temporary abutment may be particularly suitable when producing anatomical healing caps having relatively large, wide healing cuff bodies (e.g., bicuspids or molars). For smaller teeth, one may find the temporary abutment to large to be readily insertable into well 204 while allowing introduction of curable or otherwise settable dental material 236 therearound. For example, many such commercially available temporary abutments include some lateral extension beyond the simple cylindrical core body 132 shown in FIGS. 2A-2E (e.g., compare FIG. 9B). A straw configured as cylindrical core body 132 could similarly be employed.

Figure 9C:
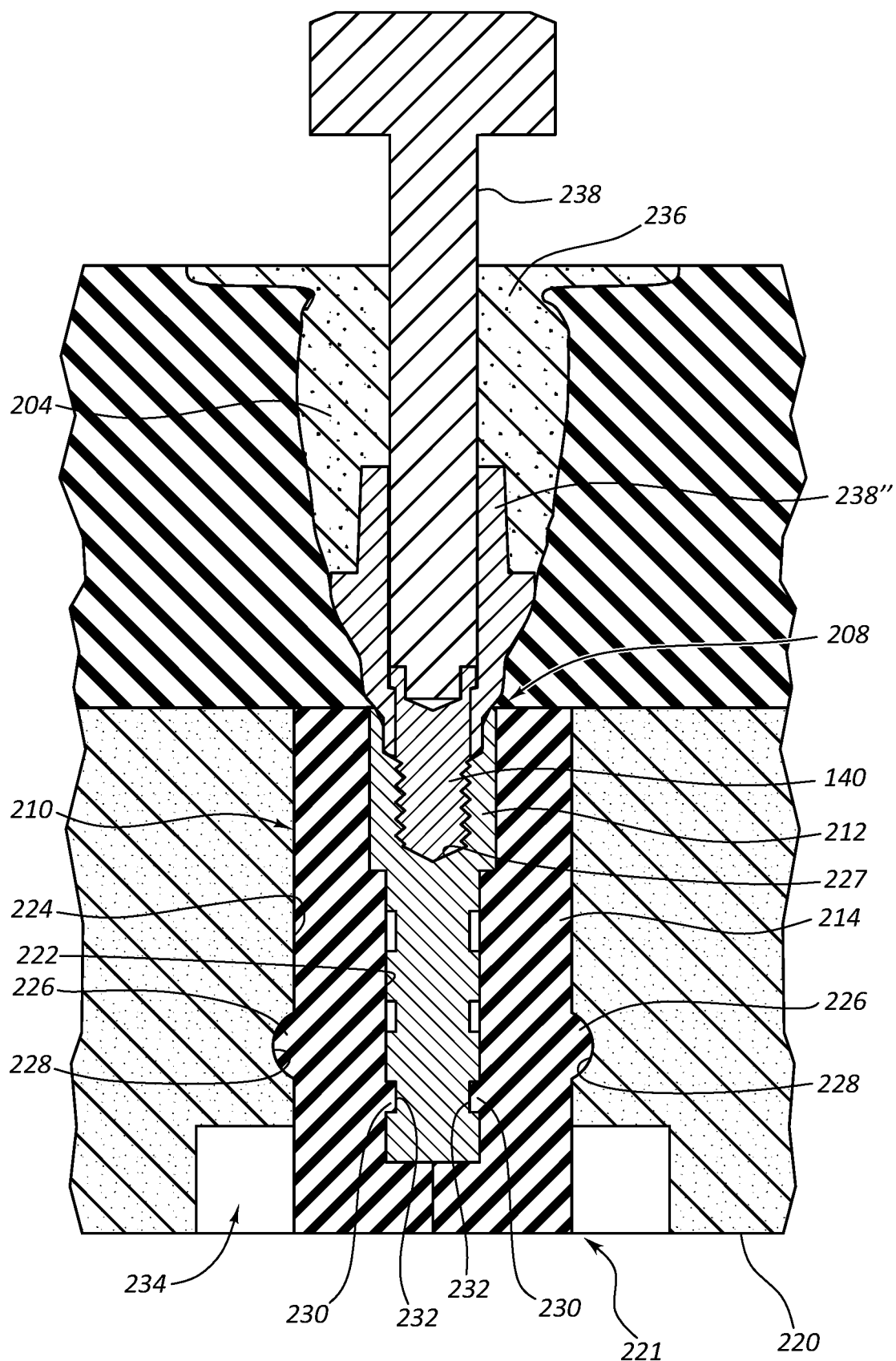
FIG. 9C is a cross-sectional view through the casting jig of FIG. 8 in which a temporary abutment having a lower profile than that of FIG. 9B is used as a core around which the anatomical healing cap is being formed.

FIG. 9C shows another alternative similar to that shown in FIG. 9B, but in which temporary abutment 238" is of a lower profile, so that it does not extend out the top of well 204. In order to preserve an access channel 138, wrench 238 is inserted therein, after which the curable or settable dental material 236 is introduced into well 204. Similar to the embodiment shown in FIG. 9B, removal of screw 140 may be possible following fabrication of the anatomical healing cap.

Examples of such temporary abutments that may be used as a core about which an anatomical healing cuff body is formed are available from various manufacturers, including Glidewell Laboratories, located in Newport Beach, Calif. Such temporary abutments employed as a core may be formed of any of various materials (e.g., including, but not limited to plastics, such as polyether ether ketone (PEEK), metal, ceramic (e.g., alumina, zirconia), etc.). Such temporary abutments may be formed by any suitable technique (e.g., casting, molding, machining, etc.)

In some embodiments (e.g., as shown in FIG. 9A), a screw may engage threaded portion 227 of implant or implant analog 212. An implant wrench may be inserted in conjunction with such a screw to preserve an access channel 138. Such a screw may be retained within the produced healing cap, providing a healing cap with a screw already incorporated therein. In one embodiment, the head of any such screw may extend through the length of any locking member (e.g., 150) to reinforce this otherwise relatively thin neck region of the produced healing cap. For example, one may simply back a typical coupling screw out a couple of turns or use a screw that is sufficiently long so as to extend through the narrow neck associated with locking member 150, into body 144a. Such an embodiment including a longer screw is shown in FIG. 11. An example of such a screw 140' may include an enlarged head 240, an undercut central portion 242 of decreased diameter relative to the enlarged head, and a distal threaded end 244, in which the threaded end defines a diameter that is intermediate the diameter of the enlarged head and the central portion. Such screw configurations (or backing out of a standard coupling screw, which is relatively shorter) reinforces the more fragile portion of healing cap 130a to prevent a break from occurring adjacent locking member 150.

Any suitable curable or otherwise settable dental material may be employed. Examples of such composite materials include, but are not limited to, glass ionomer cements, zinc polycarboxylate cements, and acrylic based curable compositions, for example, ACCESS CROWN, available from Centrix, located in Shelton, Conn. In one embodiment, the curable or otherwise settable dental material may comprise a radiopaque filler, e.g., a zirconia filled dental composite material. In addition to zirconia fillers, fillers including compounds of lanthanum, strontium, barium, zinc (e.g., zinc oxide), or combinations thereof may also be provided in order to provide radiopacity.

In one embodiment, radiographic and/or position markers may be incorporated into the anatomical healing cap 130a. For example, such markers could be inserted into a well of a casting jig, which marker may become incorporated into the resulting anatomical healing cuff body that is cast. In another embodiment, such markers may be included within a temporary abutment employed as a core about which the anatomical healing cap is formed. The markers would thus become a part of the healing cap. Such markers may be used to determine orientation, position, or other spatial information through a digital scanning or imaging process (e.g., CT scan, ultrasound, etc.) of the patient. Such markers may comprise any of the described radiopaque materials described above, or other suitable radiopaque materials (e.g., radiopaque metal alloys).

While it has been described that the casting jig may be employed to manufacture anatomical healing caps, and such manufacture may be achieved chair-side, it will be readily understood that a practitioner may choose to manufacture any number of anatomical healing caps prior to needing them, thus, "chair-side" is to be broadly construed, including where one may manufacture the anatomical healing cap prior to requiring its use. For example, a practitioner may choose to manufacture a small inventory of anatomical healing caps, which are kept and used as needed. That said, many curable or otherwise settable dental compositions cure or set up within about 3 minutes or less, such that true chair-side manufacture of a desired anatomical healing cap is certainly possible.

Figure 12:
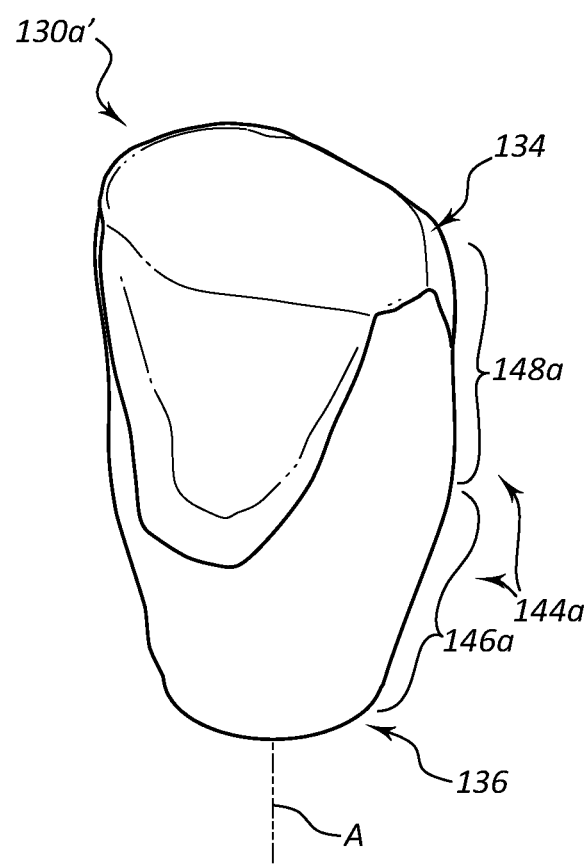
FIG. 12 is a view of a pontic configured similar to the anatomical healing caps formed using the casting jig, but which does not include a central access channel 138 or locking structure 150.

Another embodiment may not necessarily employ a socket at a distal end of the well configured to releasably receive therein a dental implant or dental implant analog. For example, for manufacture of a pontic 130a', no coupling to a dental implant is needed. Thus, one may simply cast a desired pontic having the shape of the anatomical cuff body, and the pontic may be positioned into the prepared void in the patient's jaw bone (without the need for any anchoring implant). The pontic may rather be anchored to adjoining teeth on one or both sides of the pontic. Such pontics would be similar to the described healing caps, but would not require any mechanism for coupling to a dental implant. In addition, because no coupling to an implant is required, no central access channel 138 may be needed. Thus, the pontic may be solid, without any hollow access channel. Such an embodiment is shown in FIG. 12.

9B

Figure 9D:
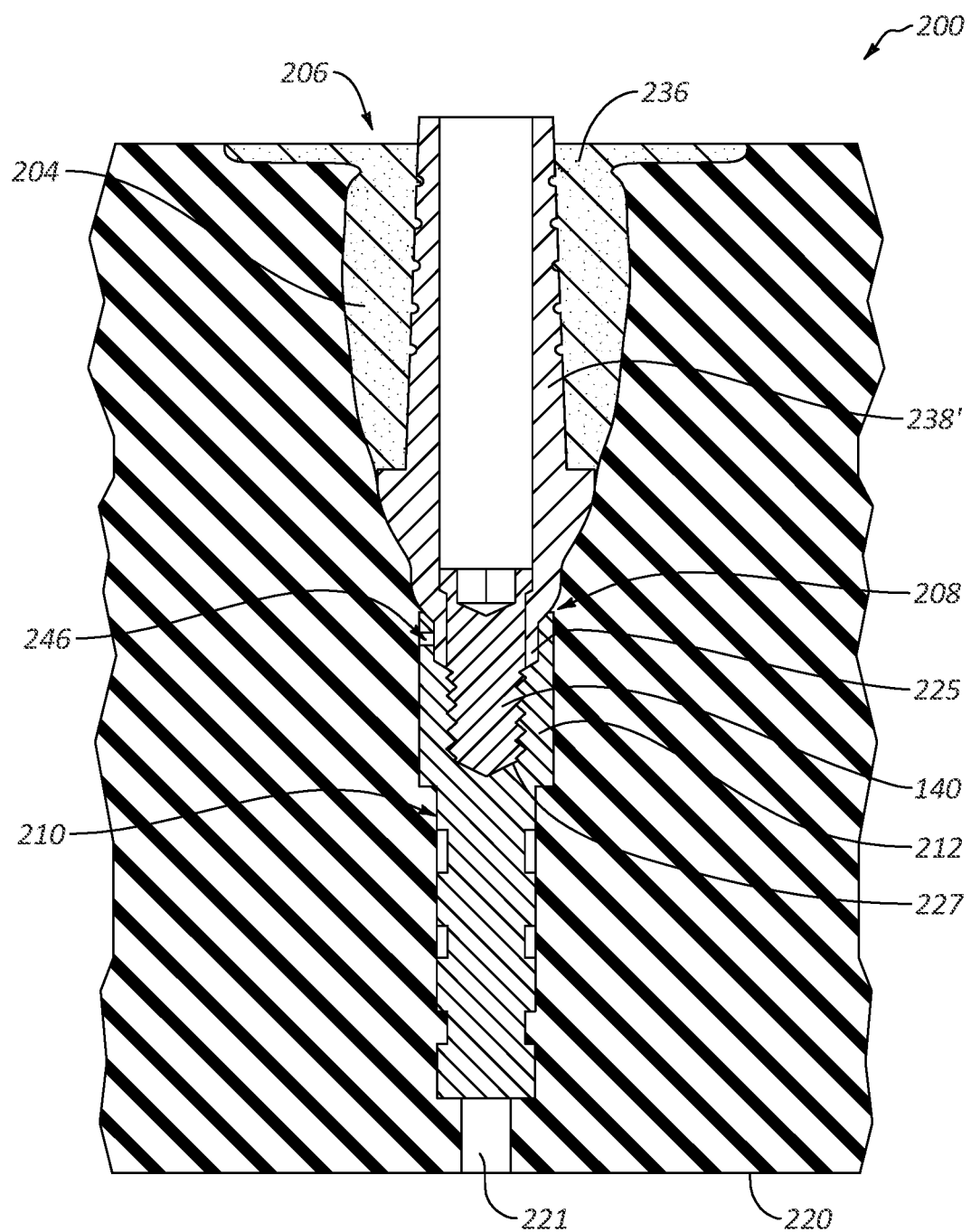
FIG. 9D is a cross-sectional view through the casting jig of FIG. 8, similar to that of FIG. 9B, but illustrating an alternative embodiment.

Another embodiment similar to that shown in FIG. 9B is described in conjunction with FIG. 9D. For example, the entire casting jig 200 (e.g., both upper and lower portions 216 and 218) may be formed of the same material, e.g., comprising a single integral piece of material. Such a casting jig 200 may be formed of an elastomeric material (e.g., silicone or polyvinyl siloxane), or a single piece of plastic. The casting jig could be molded around the implant analog 212 (e.g., by introducing silicone resin into a container around the analog, and allowing the silicone to set). Rather than including an implant housing 214 that serves as a cage (see FIG. 9B) and the implant analog 212 being inserted from the bottom of the casting jig, the analog may be removed or inserted into the casting jig 200 from above, at the top of the casting jig (e.g., through well 204). A hole or opening 221 in bottom surface 220 of casting jig 200, may be provided through which an implement may be inserted to push implant analog 212 upwards, into well 204, where it may be removed, as desired (e.g., when it is desired to remove a formed anatomical healing cap, the assembly of the healing cap and coupled analog may be upwardly pressed out).

As described in conjunction with FIG. 9B, a commercially available temporary or interim abutment 238' may be used as a core about which the anatomical healing cap is formed. Temporary abutment 238' may be inserted from above into analog 212. The typically keyed recess 225 of analog 212 may have been removed (e.g., drilled out), making the analog 212 generic to any given key. The screw 140 may be screwed down tightly into threaded portion 227 of analog 212, securing the two together. Bis-acrylic or any other suitable curable or otherwise settable material may be introduced into drilled out recess 225 at the head of analog 212, to form a keyed recess structure within analog recess 225 that corresponds to the keyed protrusion structure provided by temporary abutment 238'. In this way, a generic analog 212 may be used with any proprietary keyed structure provided with commercially available temporary abutments 238'. Analog 212 may include a transverse through-hole 246 or similar transverse recess that fills with such a settable material, helping to retain the bis-acrylic within analog recess 225 once the settable material sets or cures. The above procedures may be carried out with the analog and temporary abutment 238' located outside of the casting jig.

At this stage, the analog 212 and temporary abutment 238' are placed within casting jig 200 if not already there, with analog 212 in socket 210 of casting jig 200. Both may be introduced through the top of casting jig, via well 204. Where the casting jig is formed of an elastomeric material, the flexibility and elastic nature of the material surrounding socket 210 may allow easy insertion and withdrawal of analog 212, as needed. With analog 212 in socket 210 and temporary abutment 238' screwed into analog 212, bis-acrylic or another suitable settable dental material 236 may be introduced into well 204 to form the desired anatomical healing cap, including the buccal and lingual side handle lateral extensions 152, and 154'. Providing the T-shaped buccal side handle 152, and an oppositely disposed lingual handle extension 154' is quite advantageous, as it provides two points disposed laterally outward, on the buccal and lingual sides for easy gripping and positioning. Integrally formed handle portions 152 and 154' may easily be removed (e.g., cut away) once the healing cap is placed within the void 108, in implant 114. The presence of buccal and lingual handle extensions 152 and 154' is further advantageous as they provide a readily visible indicator of the correct orientation of the healing cap as it is seated within implant 114.

Figures 13A, 13B, 13C:
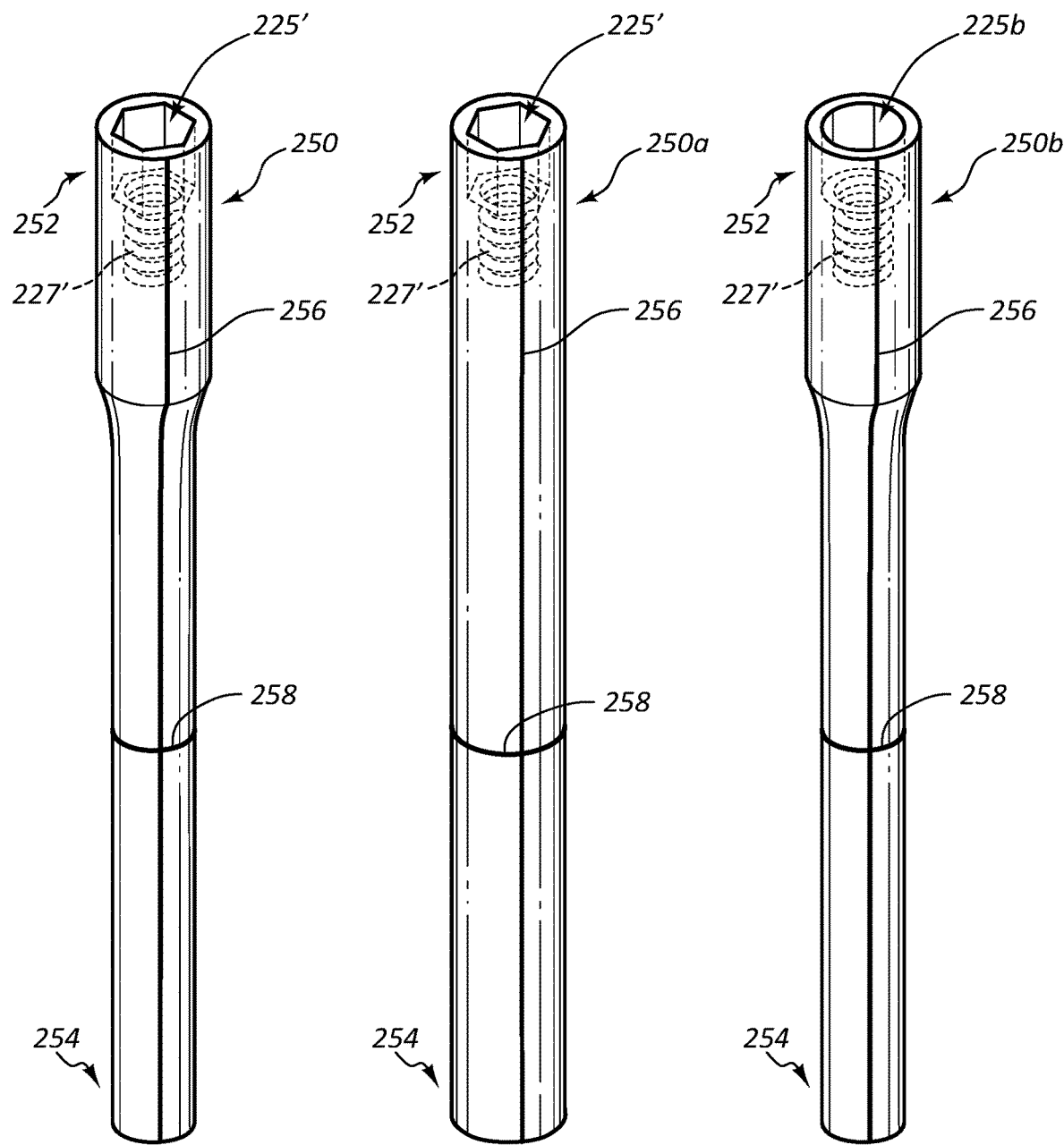
FIG. 13A illustrates an exemplary elongate handle for insertion through the opening in the bottom surface of a casting jig during manufacture of an anatomical healing cap.
FIG. 13B illustrates another exemplary elongate handle, similar to that of FIG. 13A.
FIG. 13C illustrates another exemplary elongate handle, similar to that of FIG. 13A, but with a generic recessed connection, rather than a keyed structure.
Figure 14A:
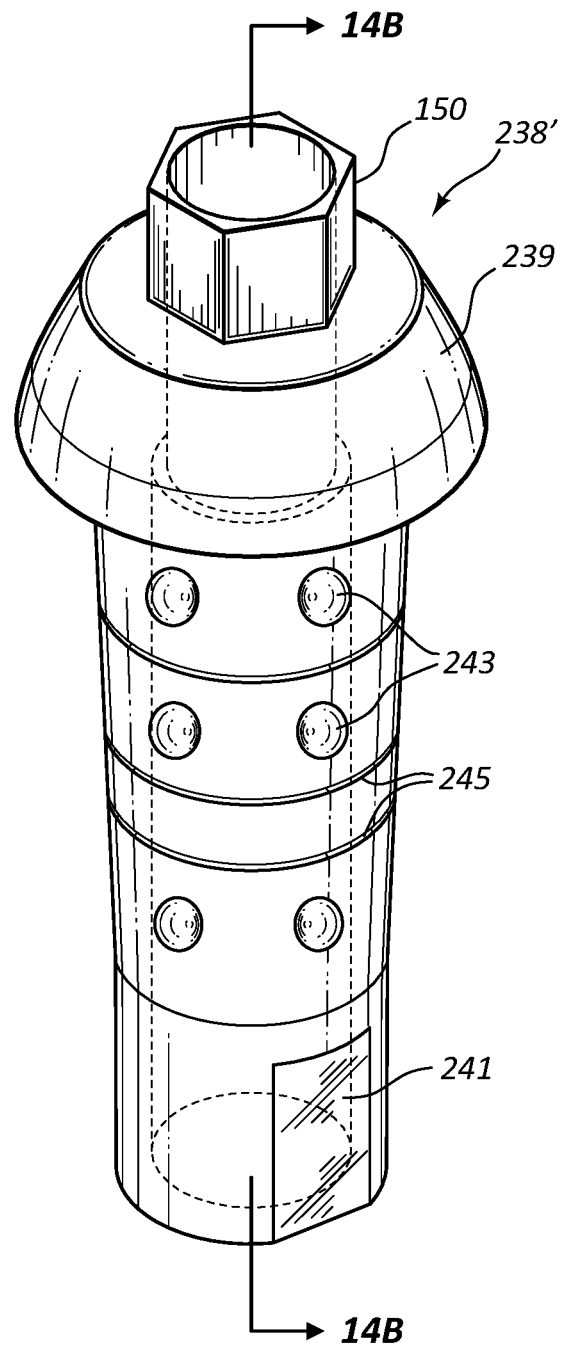
FIGS. 14A-14B illustrate perspective and cross-sectional views, respectively, of an exemplary temporary abutment core.
Figure 14B:
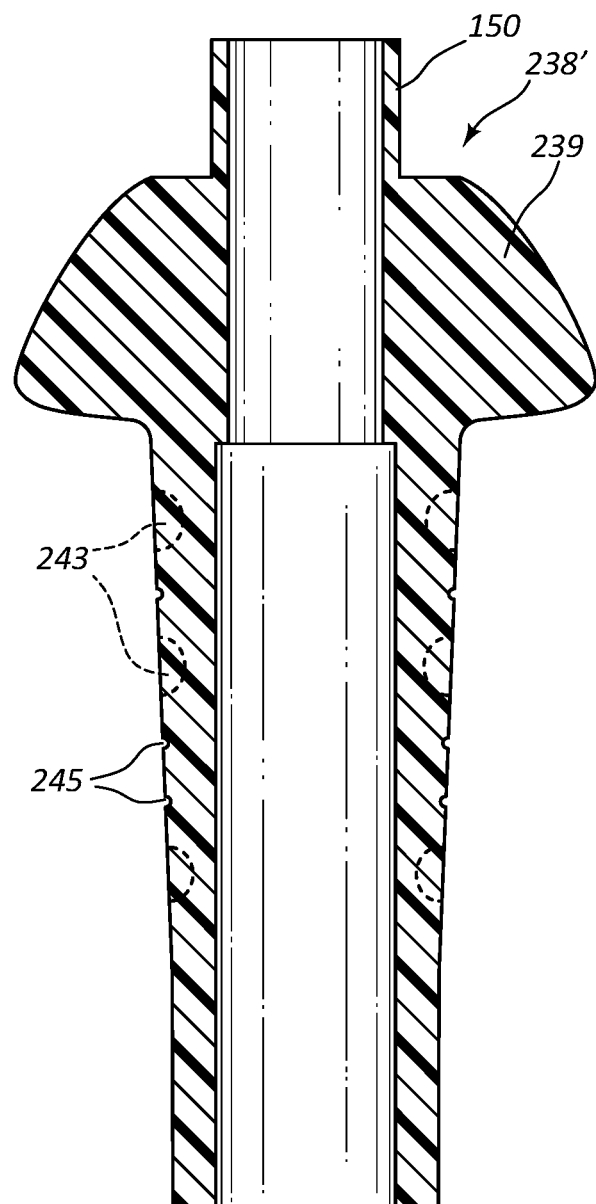

FIGS. 13A-13C illustrate an exemplary elongate handle that may be used with a casting jig system of the present disclosure. For example, a casting jig as described above (e.g., as shown in FIG. 5) may be provided, including a body 202 including one or more wells 204 formed within the body. Each well may be open at a proximal end 206 and may include a negative shape corresponding to an anatomical healing cuff body of a given tooth position. Each respective anatomical healing cuff body negative shape may include an asymmetrical cross-section and an irregular surface so that an anatomical healing cuff body having that shape provides substantially custom filling of at least an emergence portion of a void where a natural tooth once emerged from the void, or where a tooth would have emerged from the void.

A socket 210 may be provided at distal end 208 of each well, and an opening 221 in bottom surface 220 of the casting jig 200, which opening 221 opens into the bottom of socket 210 (e.g., socket 210 may simply be the top of the opening 221—where opening 221 extends from bottom surface 220 to the bottom of well 204). As shown in FIGS. 13A-13C, the system may further comprise an elongate handle 250 that is insertable through opening 221 in bottom surface 220 of casting jig 200. Of course, handle 250 could also be inserted through the top surface of jig 200 (e., through well 204). Elongate handle 250 may include a recessed connection 225' in a distal end 252 thereof, so that handle 250 may hold a temporary abutment used as a core 238' (i.e., a temporary abutment core) within well 204 of casting jig 200 as an anatomical healing cuff body (e.g., 144a) is formed about core 238'.

Figure 16:
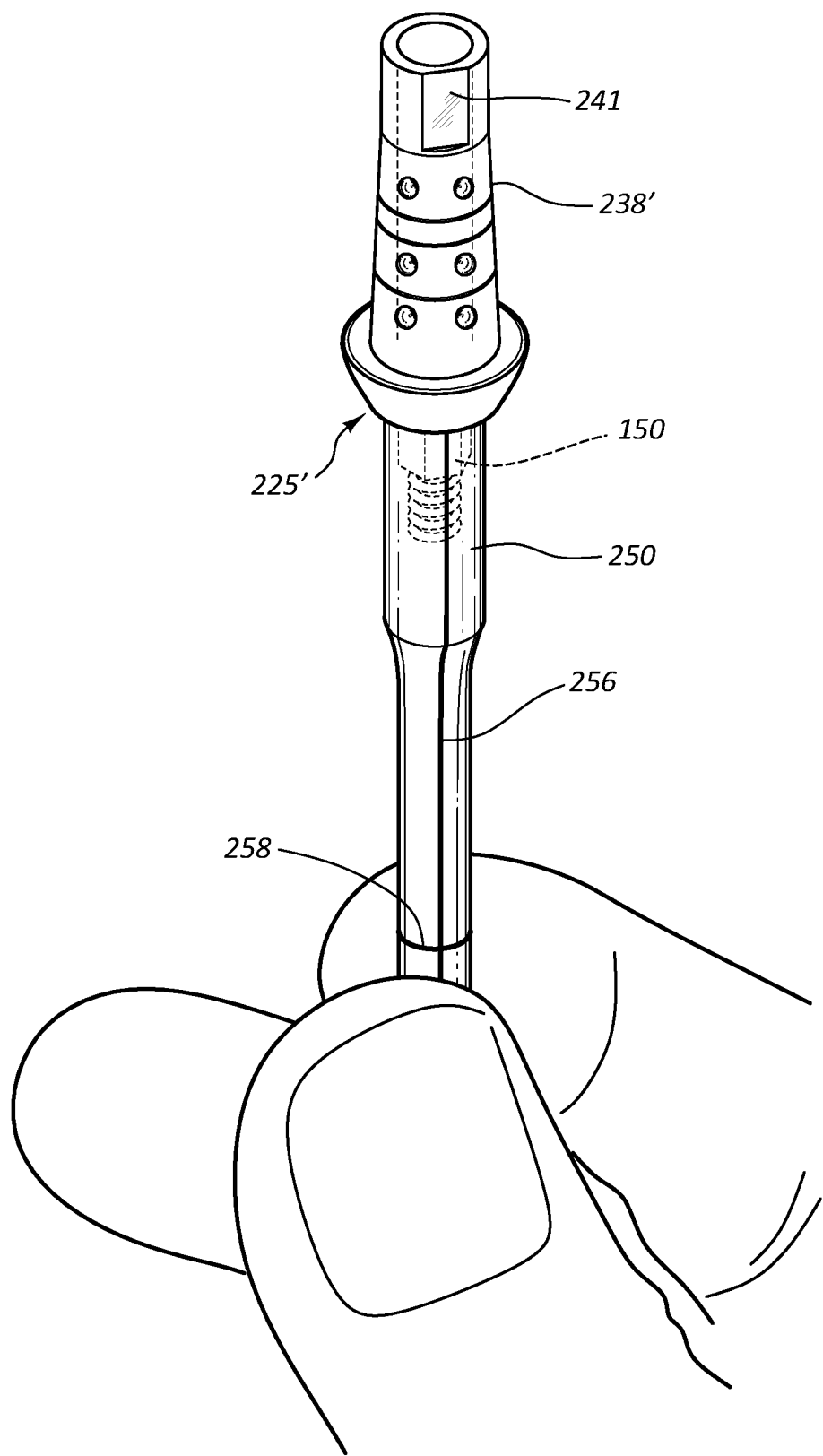
FIG. 16 illustrates a practitioner gripping the proximal end of the elongate handle with a temporary abutment core retained in the distal end thereof.

Handle 250 further includes a proximal grippable end 254 that may be grasped by the practitioner during use, as handle 250 is inserted through bottom opening 221. As seen in FIG. 13A, handle 250 may further include a generally vertical alignment marking 256 that may extend along a length (e.g., at least a portion of the full length) of handle 250. In an embodiment, vertical alignment marking is present at least at distal end 252, adjacent recessed connection 225', as it is used to assess alignment of the abutment core 238' that is retained within connection 225'. For example, as seen in FIG. 16, generally vertical alignment marking 256 is aligned with a corresponding alignment marking (e.g., a mark or flat, planar portion 241 on abutment core 238'), when core 238' is retained in distal end 252 of handle 250. These markings may correspond to the buccal side of the healing cuff body to be formed (i.e., T-shaped handle 152 seen in FIG. 18A may be on this side, aligned with marking 256 and flat 241).

Figure 17A:
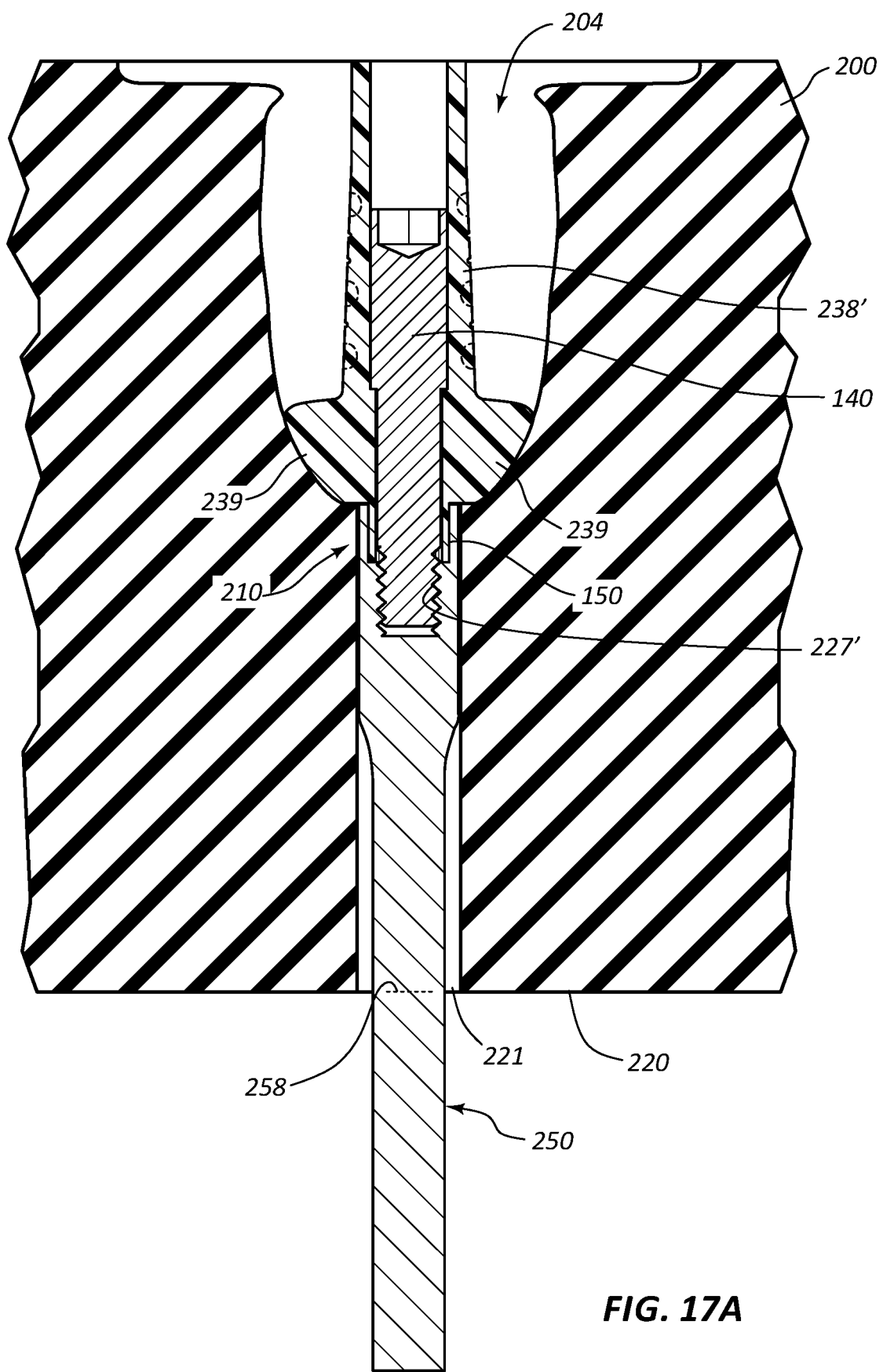
FIG. 17A illustrates the elongate handle and retained abutment core inserted through the opening in the bottom surface of a casting jig, positioning the abutment core in the well of the jig.

Handle 250 may further include a generally horizontal alignment marking 258 extending along a width (e.g., around a perimeter) of the elongate handle 250. Marking 258 may extend around the entire perimeter, or just a portion (e.g., a buccal front portion, as typically viewed by the practitioner) thereof. Marking 256 (which also may extend the entire length, or only a part of the handle) is disposed on the buccal front portion. Marking 258 may advantageously be aligned with bottom surface 220 of casting jig 200 during insertion into the casting jig, signifying to the practitioner that elongate handle 250 is full seated within casting jig 200. This is shown in FIG. 17A. For example, when so flushly aligned, such alignment may signify that the abutment 238' retained within recessed connection 225' is properly aligned vertically within well 204 of casting jig 200, so that when the curable or otherwise settable material 236 is introduced into well 204 (e.g., between the sidewalls of the well defining the negative space and abutment 238'), the structures are properly positioned to produce the anatomical healing cuff body about core 238'. Thus, the practitioner may easily and quickly verify that core 238' is in the proper rotation relative to marking 256, and that core 238' and handle 250 are inserted into jig 200 to the proper degree relative to marking 258.

As seen in FIG. 13A, distal end 252 of handle 250 may include an internal threaded connection 227' disposed proximal relative to recessed connection 225' so that a screw 140 advanced through hollow abutment core 238' seated in recessed connection 225' may be secured to handle 250 by screw 140, as screw 140 is threaded into internal threaded connection 227'. Thus, screw 140 may be used to secure core 238' to handle 250.

FIG. 13A illustrates distal end 252 including both a flared end (e.g., so that distal end 252 is of a greater width or diameter than grippable proximal end 254), and a keyed structure within recess 225'. For example, such a keyed structure may be any suitable non-circular perimeter shape that requires a particular orientation of the abutment core 238' being inserted into recess 225'. In the illustrated configuration of FIG. 13A, the keyed structure is a hexagonal recess into which a correspondingly shaped and sized hexagonal locking member (e.g., 150) may be inserted. It will be appreciated that other configurations similarly configured to lock against rotation will be readily apparent to one of skill in the art (e.g., triangular, 4-sided, 5-sided, use of non-circular curved sides, etc.), as described herein.

Flared end 252 of FIG. 13A provides sufficient length for internally threaded portion 227'. Of course, such a threaded portion may also be provided without a flared end, as seen in FIG. 13B.

FIG. 13B shows a similar configuration 250a to that of FIG. 13A, but which does not include a flared end at distal end 252. This may allow the vertical seating of the abutment 238' coupled therein to be more easily adjusted, in the jig. FIG. 13C shows a configuration 250b, also similar to handle 250, but which includes a generic recessed connection 225b. As will be described in conjunction with FIG. 20, the generic recessed connection 225b of FIG. 13C may be employed with an abutment core of any desired manufacturer, allowing the practitioner to key the generic connection 225b to whatever specific geometry the selected abutment core may include.

FIGS. 14A-14B and 15A-15B illustrate an exemplary temporary abutment core 238' about which the anatomical healing cuff body may be formed. Such an abutment core 238' may be coupled into distal end 252 of handle 250, within casting jig 200, to allow introduction of curable or otherwise settable dental material 236 into well, forming a cuff body having the desired anatomical shape provided by the negative shape defined by the sidewall of well 204. In an embodiment, core 238' may include structure in the exterior surface to aid in retaining the cuff body which is cast around core 238'. For example, the illustrated embodiment includes dimpled recesses 243, as well as perimeter grooves 245. Protruding structures could alternatively be provided. In an embodiment, a structure providing an undercut (e.g., a dovetail) may be provided, providing excellent mechanical retention between the cast cuff body and core 238' about which it is cast. The temporary abutment core 238' may be any temporary abutment commercially available from various manufacturers (e.g., Glidewell Laboratories, located in Newport Beach, Calif.). Any such temporary abutments, available from any of the various manufacturers may be employed as a core about which the anatomical healing cuff body is to be formed.

Elongate handle 250 may be of any desired length. In an embodiment, as will be apparent from FIGS. 16-17B, handle 250 may advantageously be longer than the height or "thickness" of the associated casting jig it is employed with. For example, where casting jig may be about 1 to 2 inches thick, handle 250 may be longer than the jig, e.g., more than 2 inches, e.g., about 2.5 to about 3.5 inches in length. Of course, any suitable length may be employed (e.g., which is longer than the thickness of the associated jig).

As seen in FIGS. 14A-15B, the distal end of abutment 238' adjacent the end including locking member 150 may include a flared flange portion 239. Other employed abutments may be more similar to the hollow core body 132 seen in FIGS. 2A-2H, which may not necessarily include such a flared distal flange. As is apparent from FIG. 9B-9D, such a flared flange 239 may, depending on the extent to which it extends radially outwardly from the longitudinal central axis of abutment 238', form part of an exterior surface of the finished anatomical healing cap that is formed employing the presently described casting jigs. In any case, an anatomical cuff body is formed about (e.g., surrounding) abutment 238', so as to provide the desired anatomical healing cuff body shape, which is particularly important in the emergence portion of the void (e.g., that portion of the void that is near the top of the void, where there is the greatest danger of the gingiva collapsing into the void if the void is not substantially filled). Thus, although the flared flange 239 may provide some small degree of the filling of the void (e.g., at its bottom, adjacent the dental implant), the emergence portion of the void (e.g., at the top of the void), and likely most of the void, is filled as a result of the anatomical cuff body 144a formed about abutment 238', which augments the temporary abutment core so that all of the void 108 is filled.

FIGS. 16-19 illustrate an exemplary method by which the presently described casting jig systems including elongate handle 250 may be employed in manufacture of the desired anatomical healing cap (e.g., 130a). FIG. 16 illustrates how abutment core 238' may be coupled into and retained within recess 225' of handle 250. For example, locking member 150 of abutment core 238' may be inserted into recess 225', and screw 140 advanced, so as to secure core 238' to distal end 252 of handle 250. While FIG. 16 illustrates such coupling outside of casting jig 200, it will be appreciated that this may be accomplished within the casting jig by inserting handle 250 through the opening 221 in the bottom 220 of the casting jig 200, from below, while also inserting core 238' into well 204, from above. Once core 238' meets handle 250 (e.g., locking member 150 slides into corresponding recess 225'), screw 140 may be tightened, as shown in FIG. 17A. In some embodiments, it may be easier to insert core 238' from above and handle 250 from below casting jig 200, e.g., where flared portion 239 of core 238' would otherwise make it difficult or impossible to introduce core 238' into well 204 from opening 221 and socket 210. As such, handle 250 may be inserted into socket 210 from below, while core 238' may be inserted into well 204 from above. Of course, both core 238' and handle 250 may also be inserted from the top of jig 200 (e.g., through well 204). This may be accomplished with core 238' coupled into recess 225'.

Figure 17B:
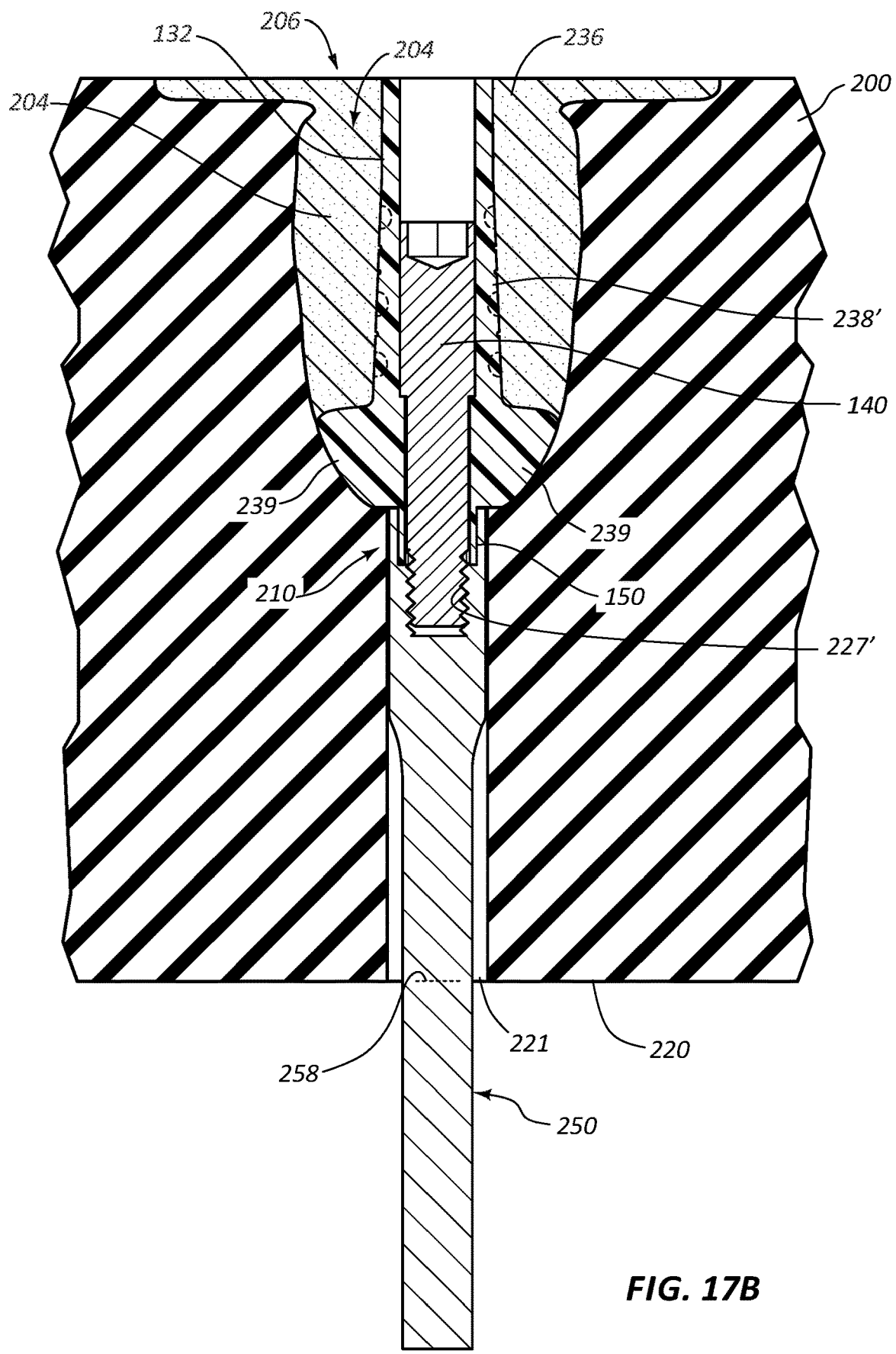
FIG. 17B illustrates injection of a curable or settable material into the well, surrounding the abutment core, which material hardens to form the desired anatomical healing cuff body surrounding the abutment core.

It will be apparent from FIGS. 17A and 17B that handle 250 takes the place of any implant or implant analog, as handle 250 includes the recessed connection 225' in its distal end 252, effectively becoming the implant analog. Thus, in such embodiments, no other dental implant analog (e.g., analog 212) may be needed. FIG. 17B illustrates how once core 238' has been properly seated into recess 225' (e.g., using screw 140) the curable or otherwise settable dental casting material 236 may be introduced into well 204, between the sidewall of well 204 and wall 132 of core 238'. Before so doing, the practitioner may verify that an alignment marking (e.g., flat portion 241) of core 238' is aligned with generally vertical alignment marking 256, and the bottom 220 of casting jig 200 is aligned with generally horizontal alignment marking 258. While flat portion 241 is shown as an example of a marking on core 238' that corresponds to line 256, it will be apparent that any suitable structure or mark may be employed, so long as the practitioner may recognize that the two structures or marks are aligned axially with one another. As such, the term "alignment marking" is to be broadly construed to include any such marks or structures.

In an embodiment, the markings 256 and 258 may include a scribed line, groove or raised ridge. They may include a colored portion therein or thereon, so as to provide contrast relative to the adjacent portions of handle 250 (e.g., red or black on a white or lightly colored handle, or white or red on a black or darkly colored handle, etc.). Such colored markings may be printed, painted, or otherwise applied. The marking could similarly comprise a flat elongate or planar portion 241 in an otherwise curved surface, as shown with flat 241 with respect to core 238'. Core 238' could similarly comprise a colored or shaped marking (e.g., a protrusion, groove, recess, etc.), other than the illustrated flat portion 241 (e.g., a printed or painted dot, line, or other mark of a color contrasting with the background). Any of the described markings employed on the handle may alternately be employed on core 238', and vice versa.

Figure 18A:
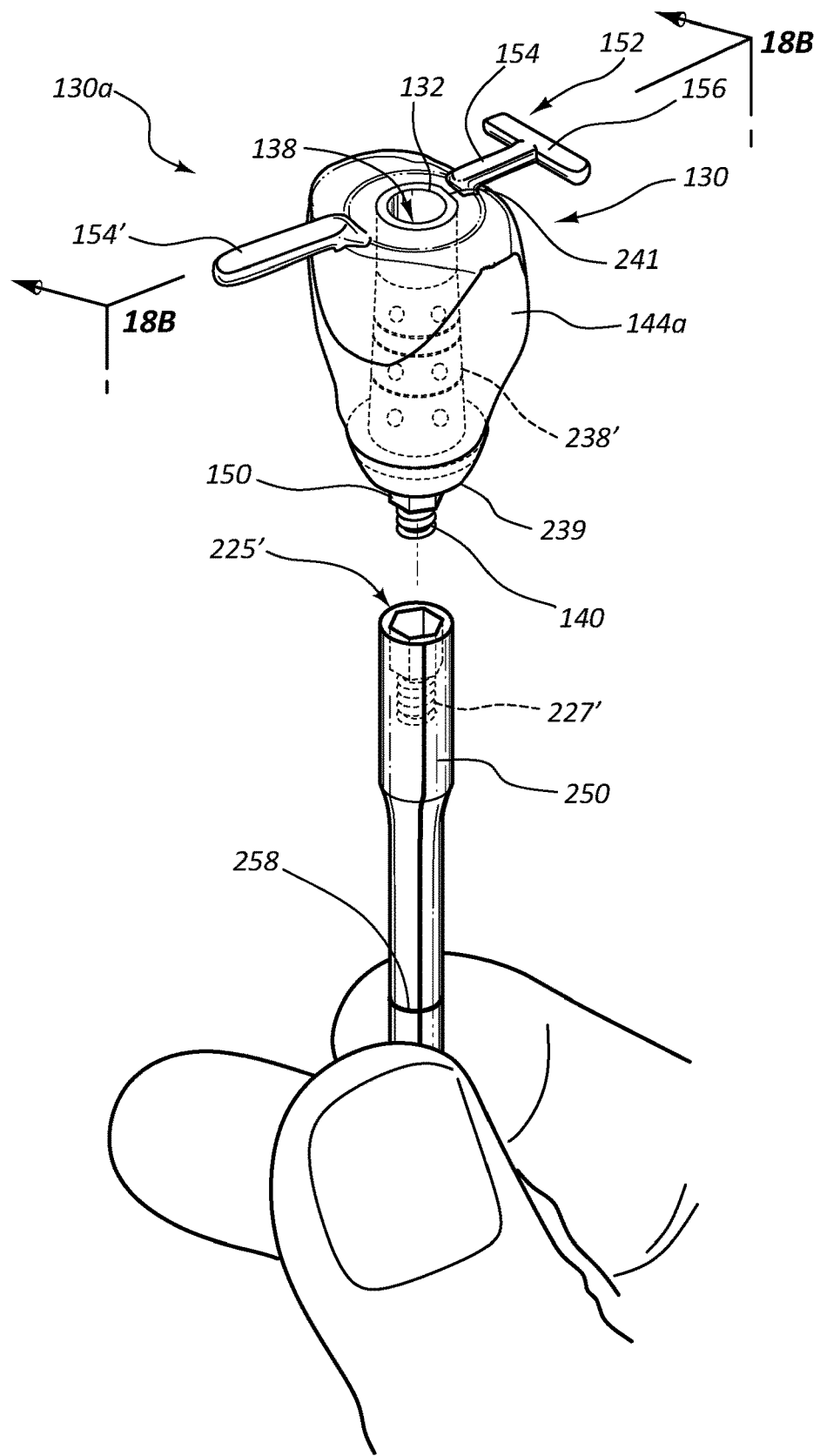
FIGS. 18A-18B illustrate perspective and cross-sectional views, respectively of the formed anatomical healing cap separated from the elongate handle, as the screw is backed out, allowing the anatomical healing cap to be removed through the top of the well of the casting jig, and the elongate handle to be removed through the bottom of the casting jig.

Because of the alignment between marking 256 and 241, the practitioner is assured that core 238' is rotated properly within recess 225'. Because of the alignment between marking 258 and bottom surface 220, the practitioner is assured that core 238' is advanced into well 204 to the proper degree. Markings 256 and 241 may correspond to the buccal side of the finished anatomical healing cap 130 (e.g., the T-shaped handle 152 may also be disposed on the buccal side, as seen in FIG. 18A).

In some circumstances, the practitioner may wish to counter-rotate the handle 250 relative to core 238', e.g., to compensate for a dental implant that is misaligned, to accommodate crowding of adjacent teeth, etc. This may be easily achieved by deliberately mis-aligning marking 256 relative to marking 241, in order to make such a compensation for mis-alignment within the patient's anatomy or the implant.

Figure 18B:
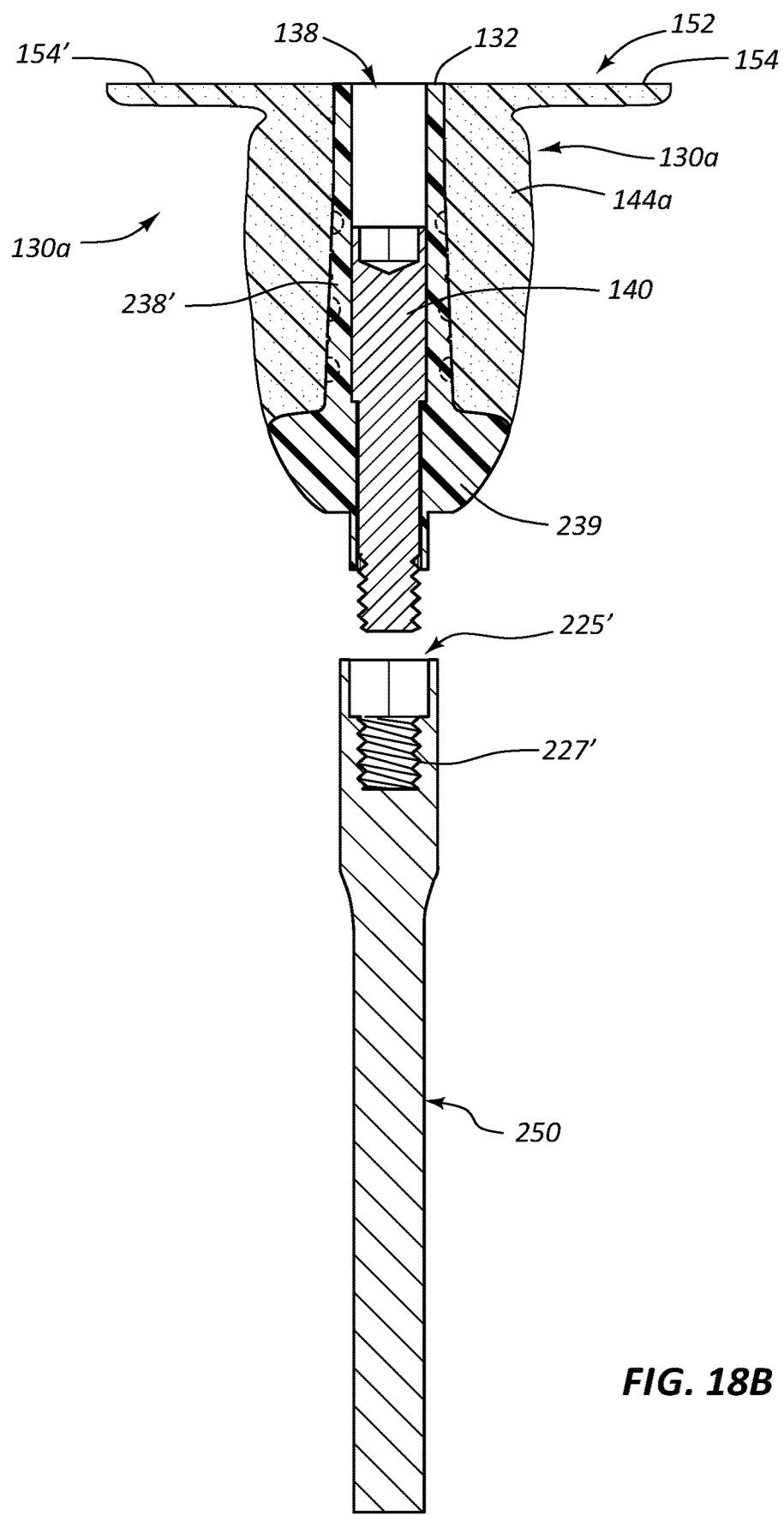
Figure 19:
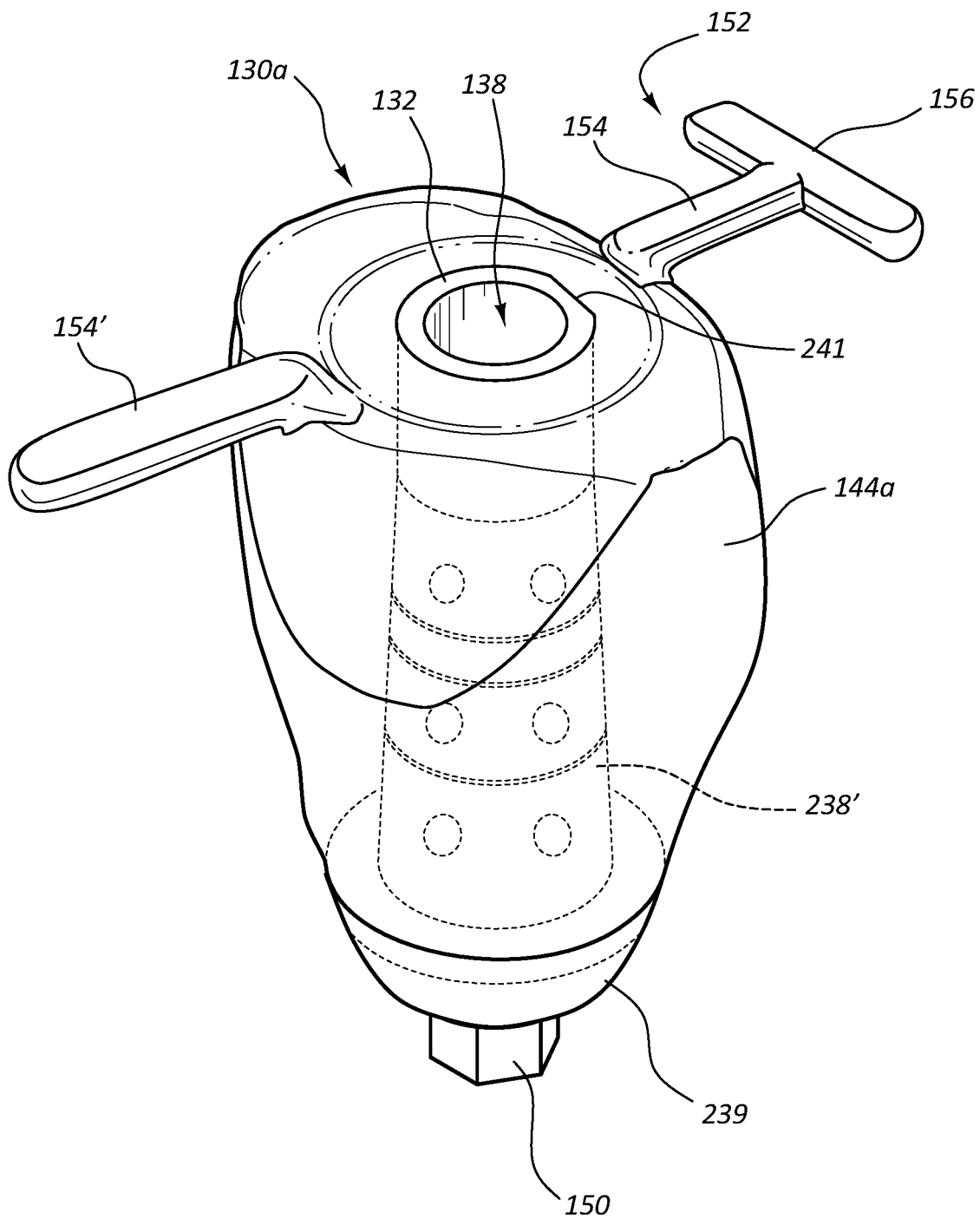
FIG. 19 illustrates the finished anatomical healing cap ready for placement into the void where a tooth once emerged or would have emerged.

The practitioner may maintain handle 250 and core 238' within casting jig 200 until material 236 has hardened to the desired degree (e.g., about 3 minutes or less). Once material 236 has hardened, screw 140 may be accessed through channel 138. Loosening screw 140 allows the formed anatomical healing cap 130a to be removed from the casting jig 200. For example, anatomical healing cap 130a may be removed through the top, through well 104, while handle 250 may be removed through the bottom opening 221. FIG. 18B illustrates a cross-sectional view of the handle 250 and formed anatomical healing cap 130a. FIG. 19 illustrates the anatomical healing cap 130a.

Figure 20:
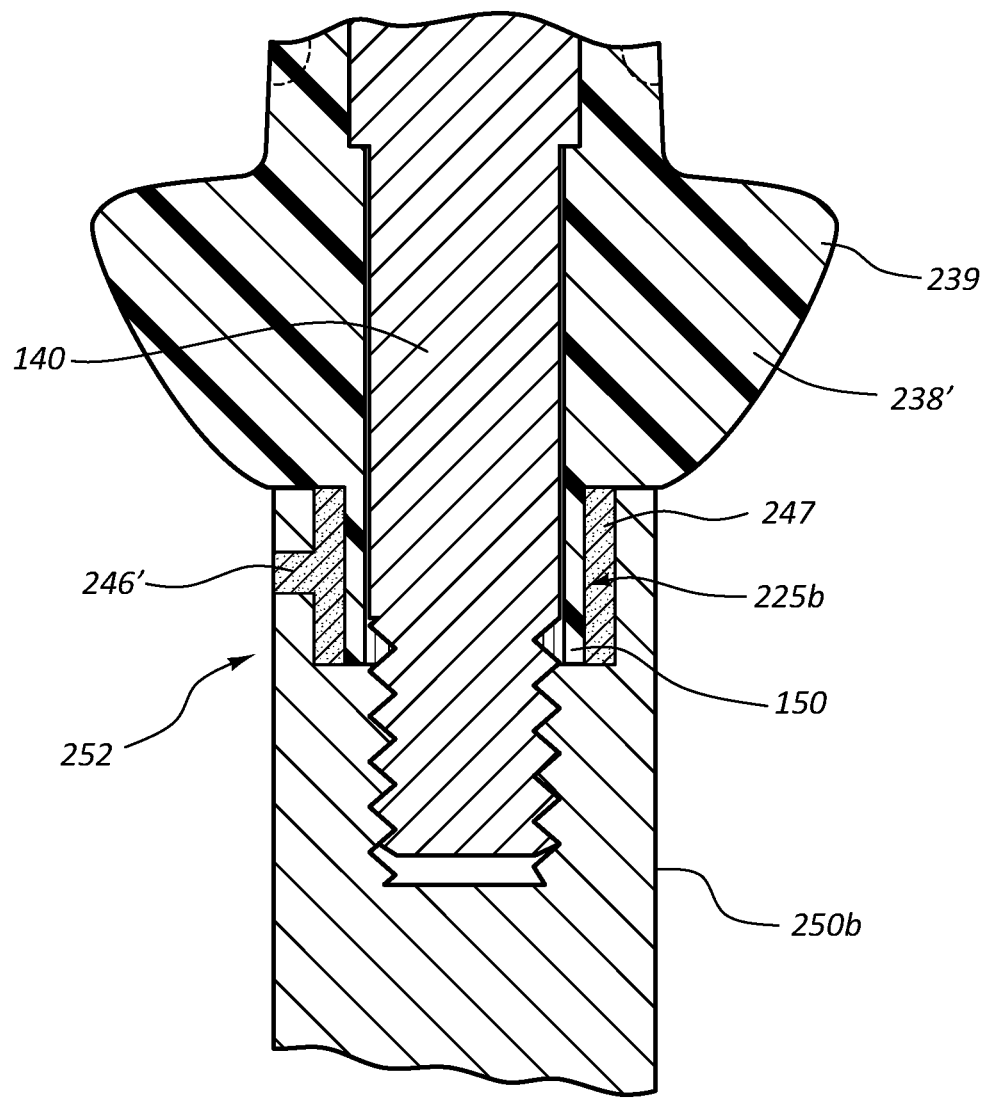
FIG. 20 illustrates how a curable or otherwise settable material may be injected into a generic recessed connection of the handle, between the circular wall of the handle and a keyed locking member of the abutment core inserted into the handle, converting the generic recessed connection so as to be keyed to the particular abutment core inserted therein.

FIG. 20 shows how a generic recessed connection 225b (e.g., such as that of FIG. 13C) may be employed with an abutment core of any desired manufacturer, allowing the practitioner to key the generic connection 225b to whatever specific geometry the selected abutment core 238' may include. This may be achieved in a similar manner as described above relative to FIG. 9D. For example, a core 238' including a keyed locking member (e.g., hexagonal member 150) may be inserted into circular recess 225b, and a curable or otherwise settable composition 247 (e.g., the same as used in forming cuff body 144a) may be injected into the space between circular sidewall of recess 225b and locking member 150. This effectively converts the distal end of handle 250b so as to be specifically keyed to the temporary abutment inserted therein, used as a core about which the cuff body is later formed. The sidewall defining recess 225b may include a recess or through-hole 246' or similar transverse (e.g., radially or sideways extending) recess that fills with such a settable material, helping to retain the injected material 247 within analog recess 225b once the injected settable material sets or cures.

Figure 22A:
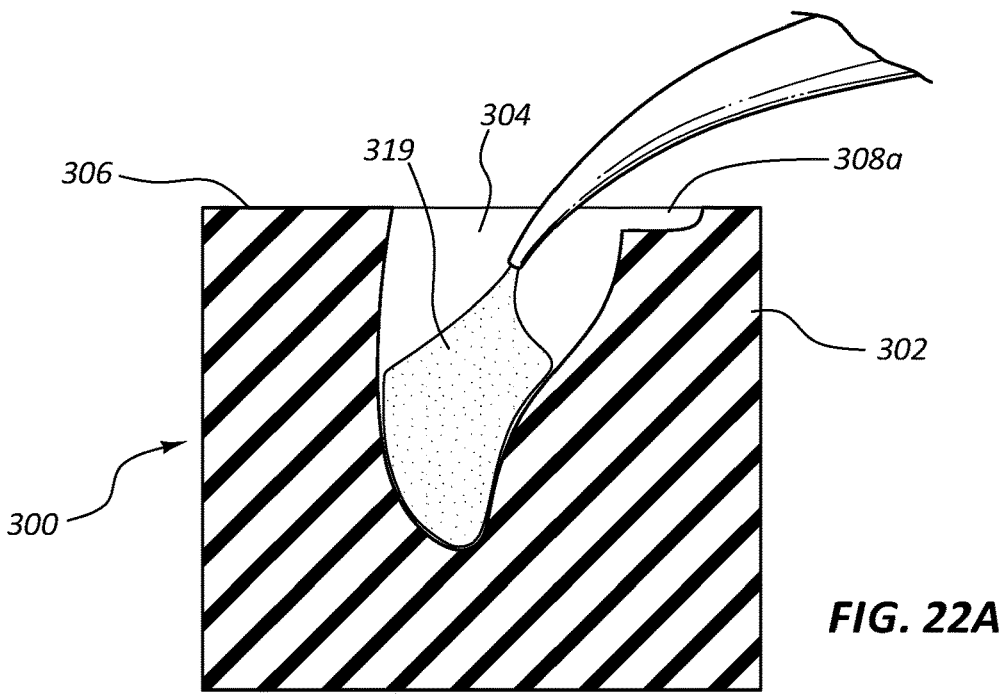
FIG. 22A illustrates the crown forming casting jig of FIGS. 21A-21C with uncured bis-acrylic material placed in the well thereof.
Figure 22B:
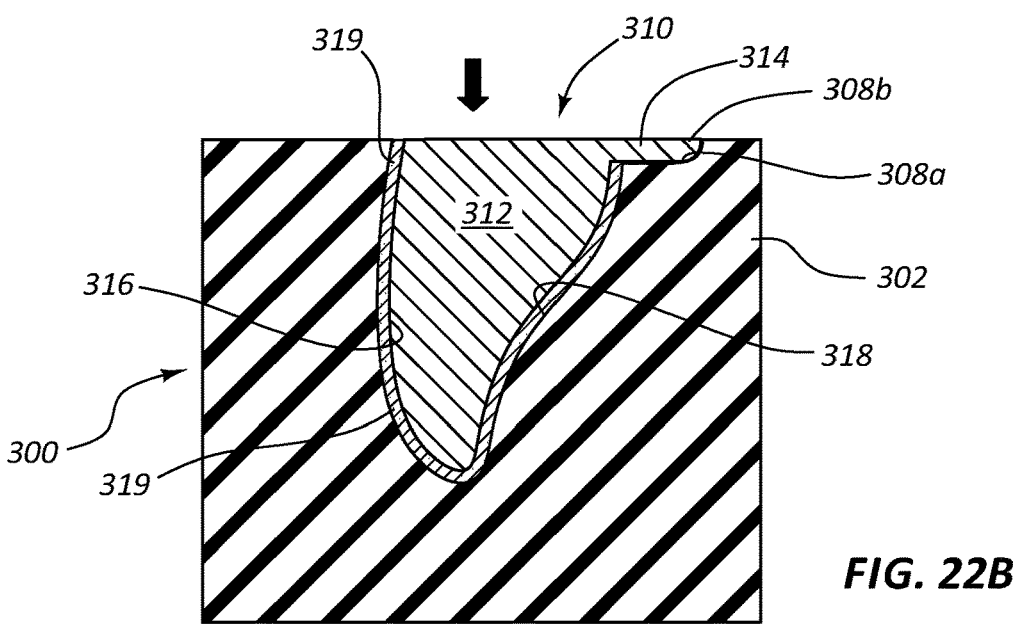
FIG. 22B illustrates a polycarboxylate slug being pressed into the well of the crown forming casting jig of FIG. 22A, seating the alignment mechanism of the casting jig and slug, while displacing the bis-acrylic material from the central portion of the well, so as to form a bis-acrylic hollow crown.
Figure 22C:
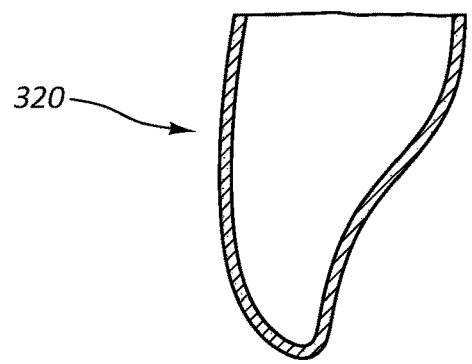
FIG. 22C illustrates a cross-section through the finished hollow crown after it has hardened and been removed from the casting jig.
Figure 23:
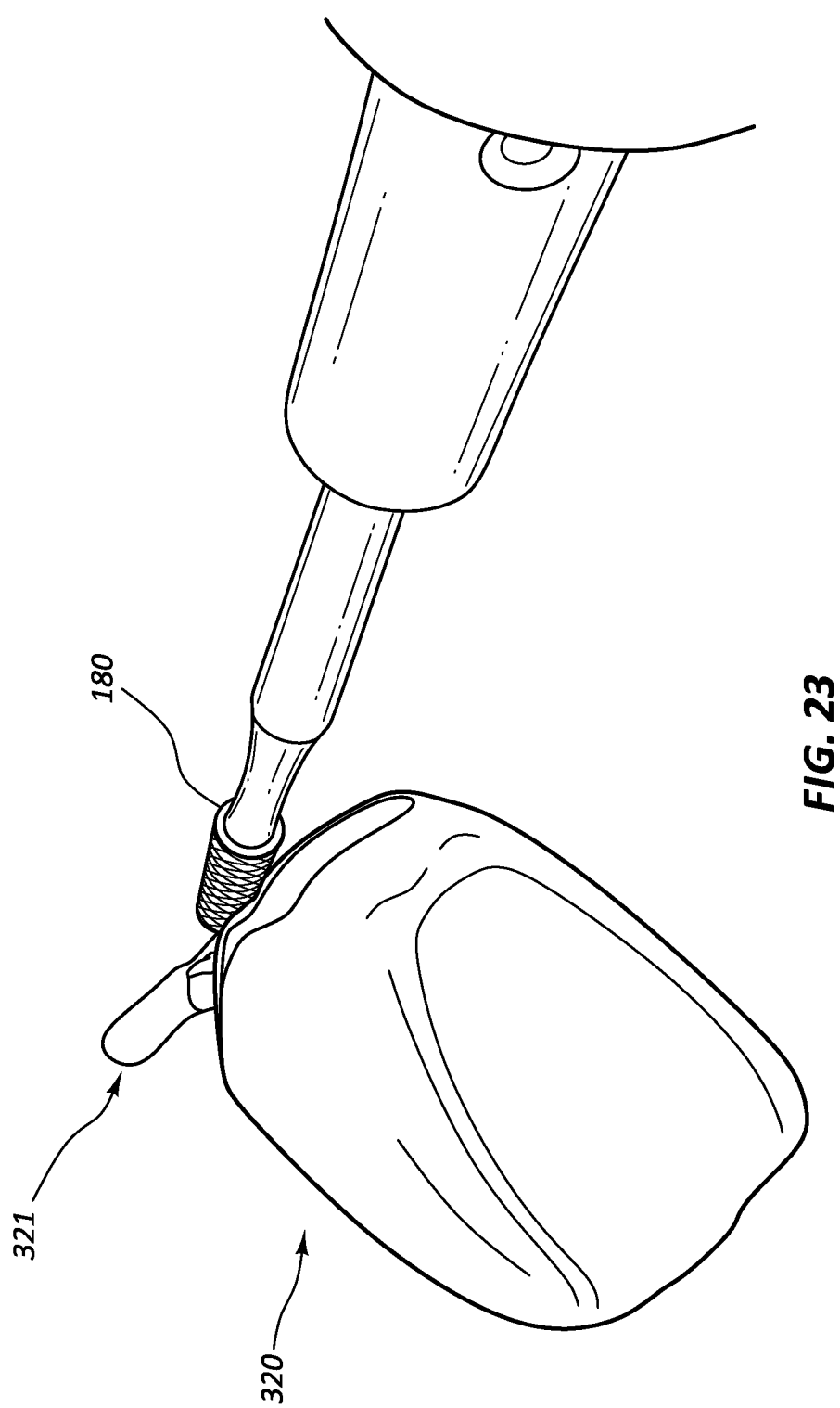
FIG. 23 illustrates an exemplary bis-acrylic hollow crown after it has hardened and been removed from the casting jig.

FIGS. 21A-23 illustrate a crown forming jig that may be used to form chair-side manufactured temporary crowns from, e.g., a bis-acrylic material or other suitable temporary crown forming material for use when installing the above described anatomical healing caps. FIGS. 22C and 23 show the finished crown 320. Crown forming casting jig 300 includes a body 302 including one or more wells 304 disposed within body 302. Each well 304 may be open at a proximal end 306, and include a negative shape corresponding to the exterior surface and contour of a crown portion of a given tooth position. In other words, just as the casting jig 200 described above includes a negative shape that when filled with a settable dental material provides a healing cuff having the anatomical shape needed to provide substantially custom filling of the void, this casting jig 300 includes a negative shape that when filled with a settable dental material (e.g., bis-acrylic), it provides a crown that has the shape and contours of the exterior surfaces of the crown portion of a natural tooth.

The casting jig further includes a first portion 308a of an alignment mechanism. Portion 308a may be disposed on or in the proximal top surface 306 of body 302 of crown forming casting jig 300. For example, in the illustrated embodiment, first portion 308a of the alignment mechanism may comprise one or more recesses arranged about well 304, which recesses may accept and mate with a corresponding second portion 308b of the alignment mechanism (e.g., configured as a mating protrusion).

The second portion 308b may comprise a portion of a slug 310 (e.g., a polycarboxylate slug) that is pressed into the uncured bis-acrylic during use, displacing a portion of the bis-acrylic material so that the bis-acrylic material in well 304 assumes the shape of a hollow crown. The slug 310 includes a central downwardly protruding displacement body 312, which is axially aligned over well 304, and pressed into well 304, displacing the bis-acrylic material outwardly, towards the sidewall defining well 304, so that as the bis-acrylic hardens, it includes a hollow central portion or core where the displacement body 312 is.

Slug 310 includes second portions 308b of the alignment mechanism, which second portions may comprise protrusions at the ends of extension arms 314 extending laterally outward (i.e., sideways) from the central displacement body 312 of slug 310. As slug 310 is pressed downwardly towards casting jig body 302, displacement body 312 is introduced into well 304, displacing the bis-acrylic material from the center, towards the outside wall of well 304. Slug 310 may include a generally vertical, upwardly oriented handle 311 to facilitate its insertion and removal. The practitioner is able to visually align protrusions 308b with corresponding recesses 308a of body 302, which aids in guiding displacement body 312 into well 304 under proper alignment. Downward advancement of slug 310 relative to body 302 may proceed until protrusions 308b contact the bottom surface of corresponding recesses 308a (i.e., they act as a stop). At this position, slug 310 is fully inserted, as seen in FIG. 22B.

This position may be configured so as to ensure that the exterior surface 316 of displacement body 312 is a given distance from the adjacent interior surface 318 of well 304, defining a casting cavity therebetween of desired thickness. In an embodiment, the casting cavity may have a substantially uniform thickness, e.g., providing about 0.5 mm all around body 312 and sidewall 318. Such a thickness provides the finished hollow crown 320 formed from the bis-acrylic with a substantially uniform thickness corresponding to that provided by the cavity, e.g., about 0.5 mm. For example, the casting cavity and crown thickness may be from about 0.1 mm to about 2 mm, from about 0.25 mm to about 1 mm, or from about 0.3 mm to about 0.75 mm.

Figure 21A:
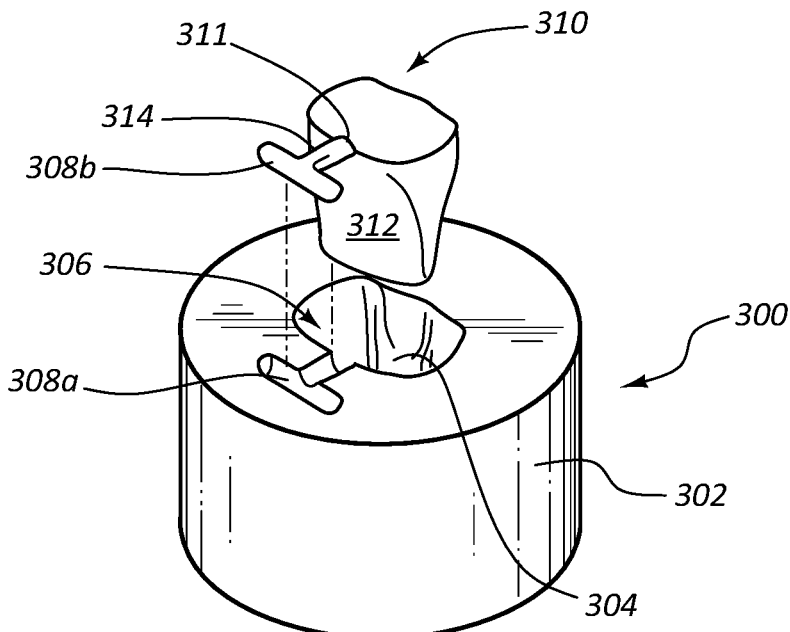
FIGS. 21A-21C illustrate an exemplary crown forming casting jig for use in forming a bis-acrylic crown for placement over the anatomical healing cap.
Figure 21B:
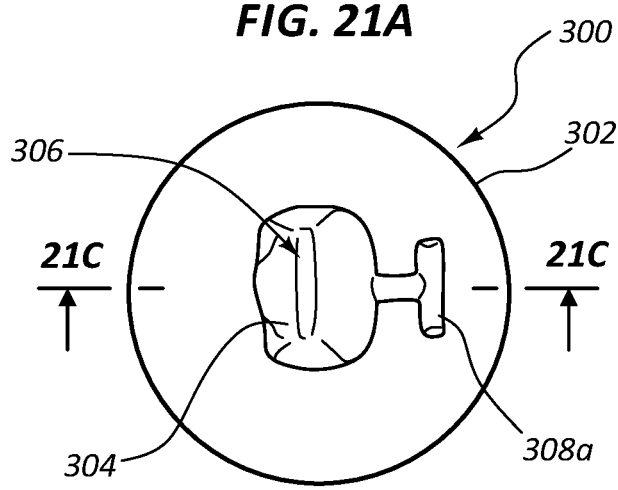
Figure 21C:
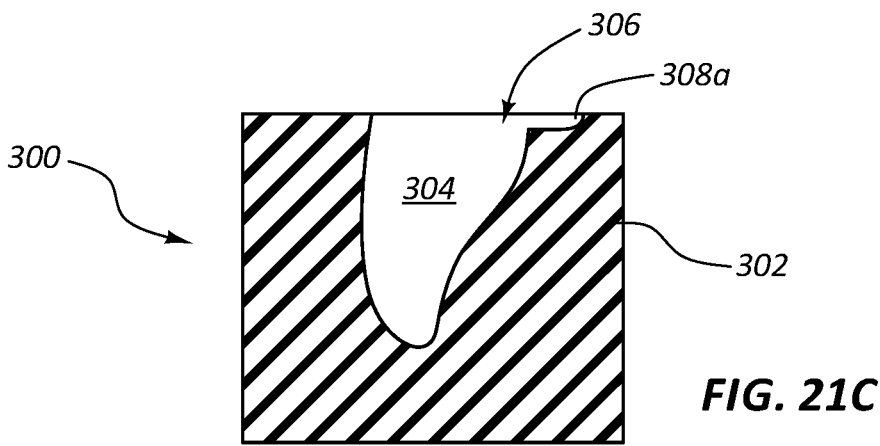

As seen in FIGS. 21A-21B, the well 304 of crown forming jig 300 may include a portion of the void of the well that forms a handle 321 (e.g., a T-shaped handle) that extends from the buccal side of the resulting finished crown 320, as seen in FIG. 23. Such a T-shaped handle may be similar to handle 152 (e.g., including a shaft and cross-bar similar to shaft 154 and cross bar 156 as seen in FIG. 2H). As shown, such a handle 321 may extend laterally (i.e., sideways) from the buccal side of crown 320, making it more easily graspable by the practitioner as the practitioner positions and holds the crown in the desired position (e.g., as it is bonded to the anatomical healing cap).

Displacement body 312 of slug 310 may provide an exterior surface 316 that is also in the shape of the crown, i.e., the negative shape provided by the sidewall 318 of well 304. Thus, when fully inserted, exterior 316 of body 312 and sidewall 318 may be substantially concentric with one another, with exterior 316 following the contour of sidewall 318, so as to provide the finished crown 320 with a substantially uniform thickness. For example, the shape of body 312 may be that of a polycarboxylate crown former. In another embodiment, the thickness may not be uniform. For example, body 312 could simply be a cylinder, pyramid or other shape that is inserted into well 304, although substantially uniform thickness and the corresponding shape of body 312 may be preferred.

The method and crown forming casting jig may be particularly advantageous where the curable or otherwise settable casting material does not adhere to the sidewall 318 of well 304, or to displacement body 312 during manufacture. This allows the finished crown to be easily retrieved from jig 300 and slug 310. In an example, the curable or otherwise settable casting material comprises an initially uncured bis-acrylic dental material, and the displacement body comprises polycarboxylate. Such materials are relatively inexpensive, and will not adhere to one another as the bis-acrylic cures, but are advantageously easily separable. The crown casting jig 300 may be formed of an elastomeric material (e.g., silicone, a polyether, etc.). Any of the materials described above relative to casting jig 200 may be employed (e.g., whether rigid, flexible, or elastomeric). It will be appreciated that other materials that are similarly non-adhesive to one another may also be used for displacement body 312 and injectable material 319, other than polycarboxylate and bis-acrylic, respectively.

Once the finished crown 320 has hardened (e.g., about 1 minute), it may be luted or otherwise bonded to an appropriate anatomical healing cap (e.g., as much of the proximal exposed portion top end of the anatomical healing cap may be removed as desired). For example, the prepared anatomical healing cap positioned within the void and anchored to the dental implant may have the crown placed thereover, a luting cement or other suitable bonding material may be disposed therebetween, the patient may be instructed to gently bite down on the crown seated on the anatomical healing cap, and the bonding material (e.g., a light curable adhesive) may be exposed to a dental curing light, securing the temporary crown in place. As shown in FIG. 23, the practitioner may wish to cut off any burrs, flashing, or perform any quick preparation or shaping of the crown after hardening with a dental burr 180 or other tool, before placement over the anatomical healing cap.

Such a procedure allows a practitioner to easily and quickly manufacture a temporary crown from an inexpensive bis-acrylic material, and quickly secure the crown over the installed anatomical healing cap. If desired, a VITA-SHADE colored resin or other material may be injected into the hollow crown 320 before placement over the anatomical healing cap (e.g., 130a) to provide a more aesthetically accurate crown, with some degree of tooth coloring (e.g., as teeth are not stark white—but include shades of yellow, red, brown, gray, etc.).

Although principally described and illustrated in a configuration where the insertion of the displacement body 312 into well 304 results in a hollow crown 320, it will be appreciated that a slug with any configuration may alternatively be inserted into well 304 (or none at all), which may result in a solid, rather than a hollow temporary crown. Such a crown may be demolded from well 304, and luted or similarly bonded to the anatomical healing cap in-situ (e.g., by placing the temporary crown over the healing cap and having the patient bite down thereon, and exposing a light cure adhesive between the crown and cap to a dental curing light. Such solid crowns may be inexpensively and easily formed using bis-acrylic or a similar temporary crown material introduced in a flowable condition into the well 304, after which it is allowed to cure or otherwise set. Such a solid crown may be aided in removal from the well by inserting an appropriately dimensioned hollow straw, or solid rod (e.g., similar to a toothpick) into the material before or as it cures to aid in its removal from the well. Such may be cut or otherwise removed before placement in the patient's mouth.

The provisional crown 320 may be removed (e.g., by loosening the screw coupling the anatomical healing cap into the dental implant) at a later stage (e.g., weeks later) when a permanent crown (or other restoration) has been prepared and is ready for installation. Of course, it could also be removed by breaking or cutting it off. In any case, at this point, because the anatomical healing cap has been in the void of the alveolar ridge for this period of time (e.g., several weeks), the gingival tissue surrounding the void has not collapsed into the void, but has been supported by the anatomical healing cap for the entire healing time. It will be apparent that temporary restorations other than crowns (e.g., bridges, inlays) may be formed using an appropriately configured crown forming casting jig where the well of the casting jig includes a negative shape corresponding to the desired bridge, inlay, etc.

As used herein, the terms "proximal" and "distal" may generally refer to the orientation or position of the given structure relative to the end of the device being manipulated. Thus, the end 254 of handle 250 may be "proximal", while locking member 150 of core 238' may be "distal", even though the distal end of core 238' may be coupled into the distal end of handle 250. This is because when the anatomical healing cap that may include core 238' is installed into a patient's mouth, the end including locking member 250 is "distal" as it is being installed.

IV. Methods for Taking a Scan or Impression

As mentioned herein, a practitioner may wish to take an impression, or make a scan (e.g., a digital or other scan such as a CT scan, x-ray, or the like) of the structures and surfaces surrounding the anatomical healing cap once it has been placed into the subgingival void 108. Under existing methods, the practitioner typically removes the cap or cuff 116 (seen in FIG. 1F), and couples an impression post or scanning body into the implant. With the impression post or scanning body in place, the impression or digital scan is taken. The impression post or scanning body may then be removed, and the cap or cuff 116 replaced. It will be apparent that such methods are undesirable, as they require removal of the cap or cuff, followed by its eventual replacement.

The present disclosure provides an alternative method which allows the impression post or scanning body (depending on whether an impression or a scan is being taken) to be seated directly into the anatomical healing caps described herein, resulting in a stack of 3 structures (the implant 114, the anatomical healing cap 430, with the impression post or scanning body 462 on top). For example, the anatomical healing cap itself may make provision for receipt of the impression post or scanning body therein. Mechanisms for keying the interior of the hollow anatomical healing cap with the scanning body (or impression post) may be provided.

Figure 24A:
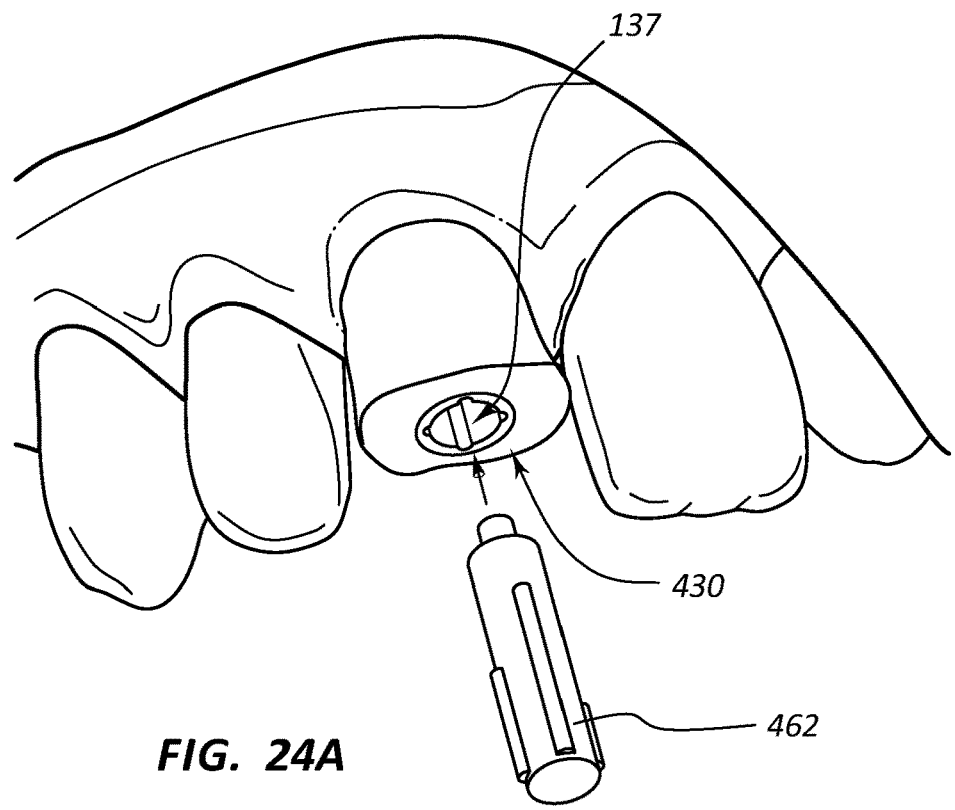
FIG. 24A illustrates a scanning body or impression post being inserted into an open end of an anatomical healing cap, such that the body or post is atop the healing cap, and the healing cap is atop an implant, all in-situ.
Figure 24B:
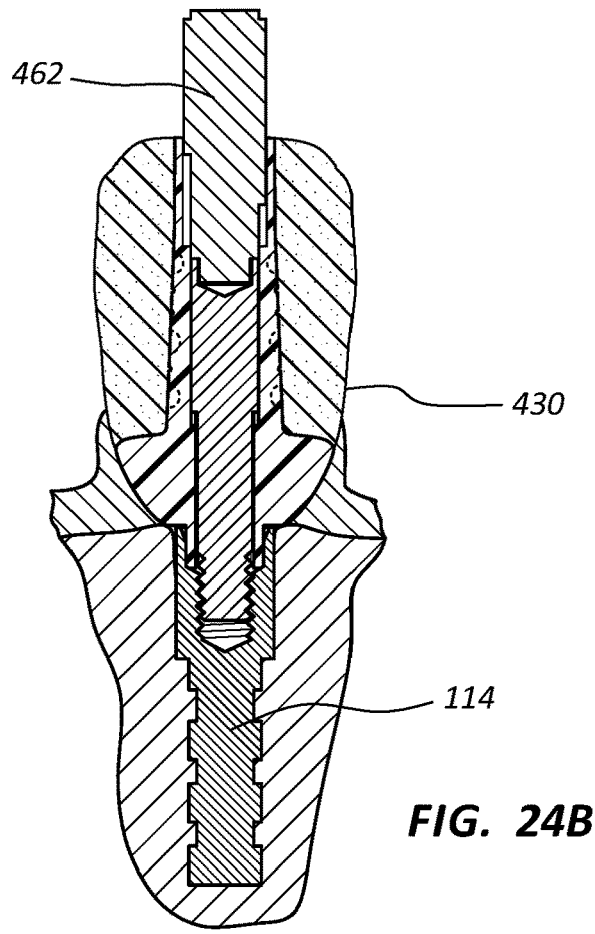
FIG. 24B is a cross-sectional view of the stacked implant, anatomical healing cap, and scanning body as seen in FIG. 24A.

FIGS. 24A-24B show how scanning body or impression post 462 may be inserted into open end 137 associated with hollow channel 138 of healing cap 430. As described above, it will be appreciated that healing cap 430 may be formed around a temporary abutment 238' as described (e.g., see FIGS. 14A-19). The terms scanning body and impression post may be used interchangeably herein (e.g., where one may be selected if a scan is to be made, the other to be selected if an impression is to be taken). The two structures may generally be similar to one another in shape, size, etc. Typically, an impression post may be formed of metal, while a scanning body may typically be plastic. Such structures are typically too weak to serve as a permanent post supporting a crown or the like.

Figure 25A:
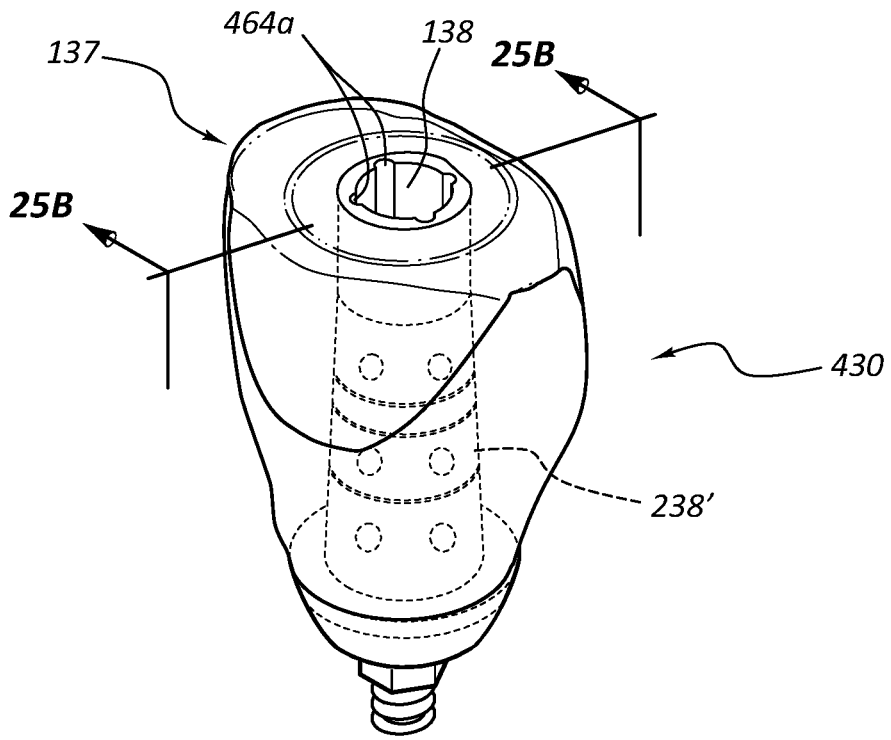
FIG. 25A-25B are perspective and cross-sectional views, respectively, of an anatomical healing cap, such as that seen in FIG. 24A.
Figure 25B:
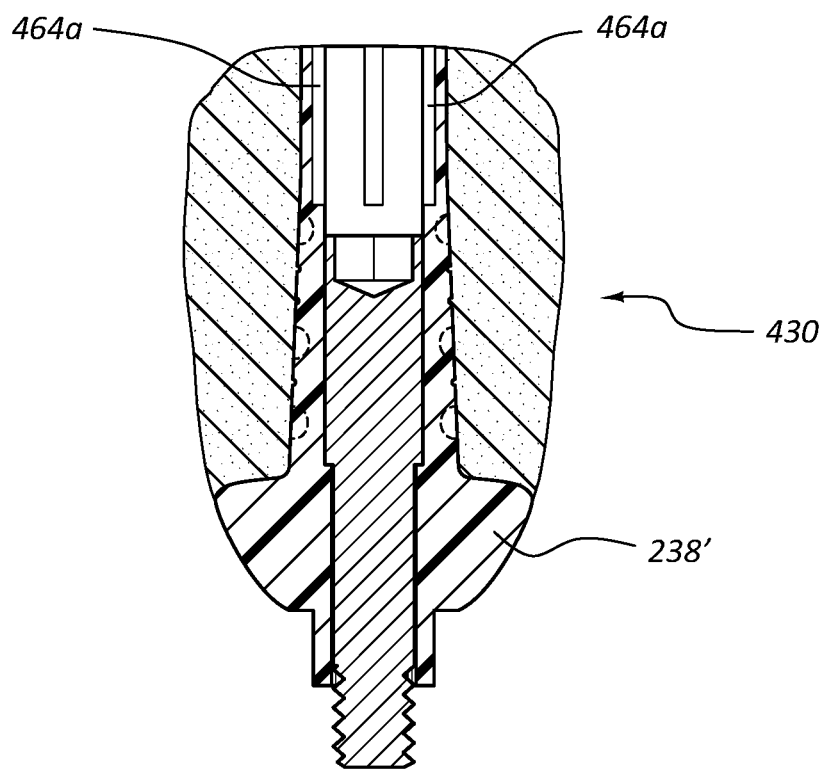
Figure 26A:
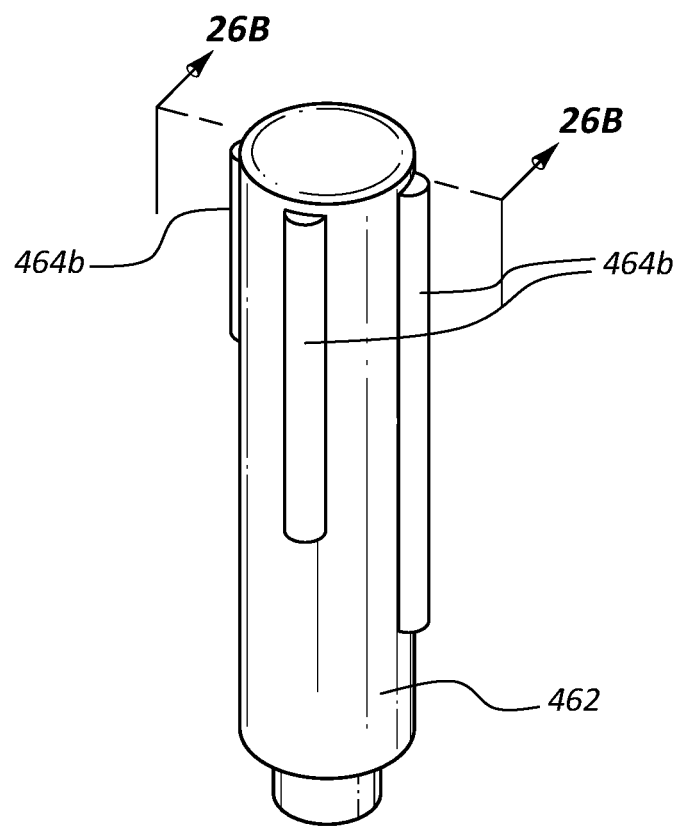
FIGS. 26A-26B are perspective and cross-sectional views, respectively, of an impression post or scanning body as seen in FIG. 24A.
Figure 26B:
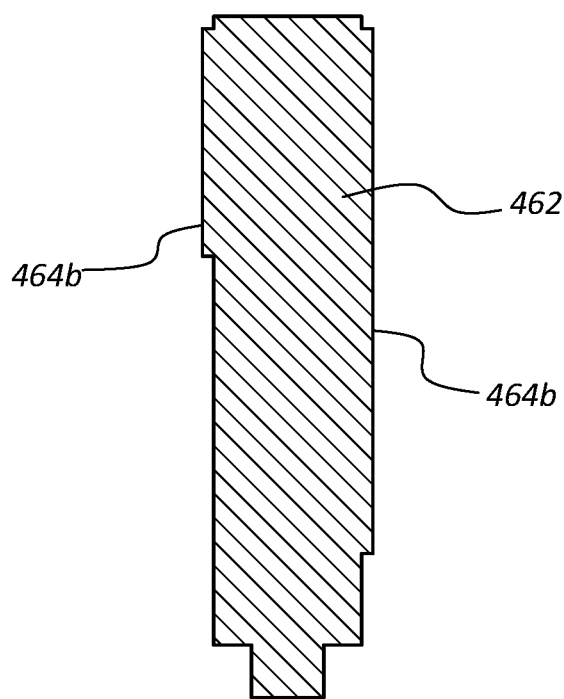

Scanning body or impression post 462 and anatomical healing cap 430 may be keyed to one another, to ensure desired rotative orientation of body or post 462 within anatomical healing cap 430. FIGS. 25A-25B show perspective and cross-sectional views of an anatomical healing cap 430. It will be appreciated that any of the anatomical healing caps described herein may be provided with keyed or other features described in conjunction with anatomical healing cap 430. For example, one or more grooves 464*a* may be provided within channel 138, where the grooves 464*a* extend from the open end 137, vertically downward some given length. A plurality of such grooves may be provided, of different lengths relative to one another. Scanning body or impression post 462 may include one or more mating protrusions 464*b* which are configured to mate within grooves 464*a*. FIGS. 26A-26B show perspective and cross-sectional views of impression post or scanning body 462.

Different length grooves 464*a* may ensure proper orientation of scanning body or impression post 462 in channel 138 of anatomical healing cap 430, as if the scanning body 462 is mis-rotated, it will either not slid down into channel 138, or it will not slide down so that each protrusion 464*b* seats within the bottom of each respective groove 464*a*. For example, if the grooves 464*a* and protrusions 464*b* are aligned with one another, but mis-matched (not of the same length), then the scanning body or impression post 462 will slide down into channel 138 only until the bottom of the shortest groove is reached. At such position, it will be apparent that the scanning body or impression post 462 sits too high in channel 138, and the practitioner will realize that further rotation within channel 138 is needed, such that body or post 462 may be withdrawn, rotated, and reinserted. The grooves (and protrusions) may be of differing widths if it is desired to ensure that insertion may only occur at the correct rotated orientation. Such grooves (and protrusions) may be equally spaced around the perimeter of body or post 462 and the interior surface of channel 138, or otherwise arranged, as desired (e.g., 3 protrusions/grooves 120° apart, or 4 protrusions/grooves 90° apart). Color coding, numbering, or other matching indicia may be used to aid the practitioner in achieving correct rotational alignment of the protrusion(s) and groove(s)

With the body or post 462 fully seated in channel 138, the practitioner may then proceed to take an impression or scan, as is the preference of the practitioner. In order to provide a further check to the practitioner that seating of the body or post 462 in channel 138 is complete, a marking (e.g., dot, groove, protrusion, horizontal line, or the like) may be provided, e.g., on the exterior of the body 462, e.g., which may align vertically with the top 137 or channel 138. Seeing a horizontal line or other marking aligned with top 137 may serve to inform the practitioner that full seating has occurred, much like horizontal line 258 informs the practitioner of correct seating in the casting jig as described in conjunction with FIGS. 13A-17B, above.

It is not necessary that the body or post 462 be coupled by screw or similar mechanism into the anatomical healing cap 430, although such could be provided for, if desired. In a preferred embodiment, no such screw is provided, such that the anatomical healing cap may be screw coupled into the implant (e.g., implant 114), but where no screw coupling is provided between anatomical healing cap 430 and body or post 462. In some embodiments, body or post 462 may be provided with a mechanism that allows the received portion of the body or post 462 to exert an outward pressure onto channel 138, aiding to hold it in place while being used. Such mechanism may be selective, e.g., allowing the practitioner to lock the body or post 462 in place, and then to release such mechanism when the impression or scan has been completed, and body or post 462 is to be removed. Such a mechanism could provide a mechanical switch, trigger, or button (e.g., at the top of post 462) which upon actuation may cause a perimeter portion of body or post 462 to extend laterally or radially outward, exerting increased pressure against the interior of channel 138. Release of such mechanism may cause retraction to the initial (e.g., default) position, making it easier for the practitioner to then pull body or post 462 from channel 138.

Where a scan is being taken rather than an impression, the practitioner may find it helpful for the anatomical healing cap, the scanning body, or both to include radiopaque markers incorporated therein, providing a reference about which the image derived from the scan can be created. For example, the protrusions 464*b* may comprise a radiopaque material, and/or grooves 464*a* may be coated with a radiopaque material. Where such protrusions or grooves are of different lengths, the difference in lengths may aid in compiling the image from the scan data, as the different length protrusions and/or grooves are unique to one another, each creating a reference point for the scanner.

Before conducting such a scan, the practitioner may apply a radiopaque powder (e.g., any of the radiopaque materials identified herein, in powdered form) around the gingival cuff and any other surrounding surfaces, so that these surface contours better show up in the scan.

It will be appreciated that such embodiments simplify the overall process required by the practitioner, by allowing taking of an impression, or taking a scan without actually having to remove the healing cap, but by providing the ability to seat the scanning body or impression post into the healing cap itself. This allows the practitioner to take the desired impression or scan while leaving the healing cap in-situ, in place in the subgingival void.

V. Implants with Markers for Taking a Scan

Figure 27A:
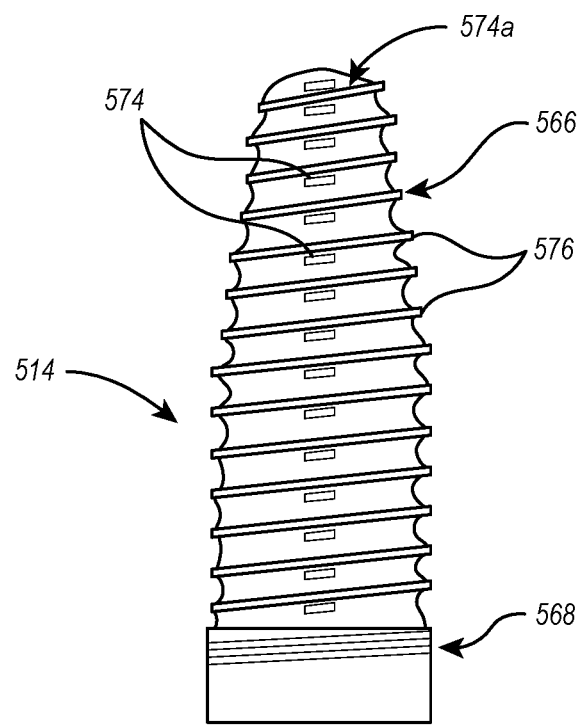
FIGS. 27A-27C illustrate a dental implant that includes radiopaque markers on or within the implant.
Figure 27B:
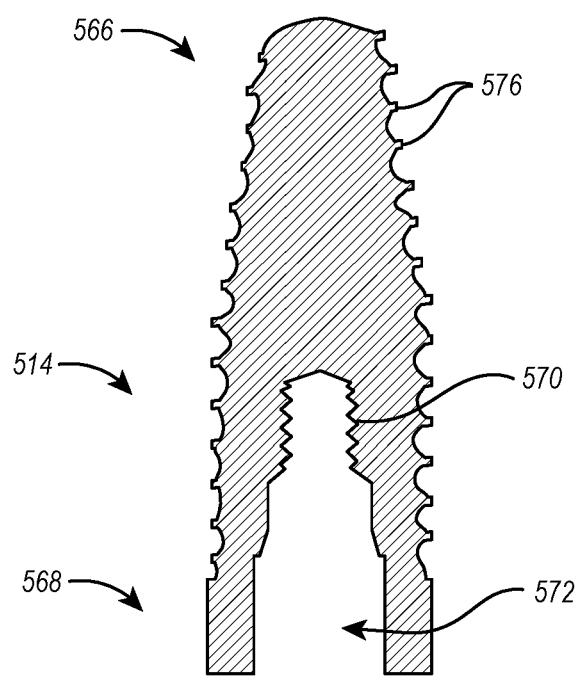

FIGS. 27A and 27B illustrate an exemplary dental implant 514. Implant 14 referenced in the present description may be an implant such as that shown at implant 514 in FIGS. 27A-27C. Implant 514 comprises a body including a threaded distal end 566 configured for reception and implantation into a jaw bone of a patient, as illustrated in FIGS. 1B-1E. The body of implant 514 also includes a proximal attachment end 568. The implant 514 may include internal structure (e.g., internal threads 570) as shown, allowing mating reception of threads 142 (see FIGS. 2A-2H) of the anatomical healing abutment (e.g., 130*a*) or a healing abutment of an entirely different design. As shown, implant 514 may include internal threads 570, in addition to the illustrated external threads 576. Internal threads 570 may be configured for mating with threads 142 of the healing abutment (e.g., 130*a*). Implant 514 may also include a keyed negative shape (a void) 572 corresponding in shape and size to the keyed structure of the healing abutment (e.g., hexagonal locking structure 150 of FIGS. 2A-2H), which structure is matingly receivable in void 572. In another embodiment, the implant and the healing abutment may include a structure analogous to locking structure 150 and void 572, but which is not keyed, and provides no locking function (e.g., a cylinder).

As shown, the implant body of implant 514 may further include a plurality of markers 574 positioned on or within the implant body. For example, in an embodiment, the markers 574 may be positioned on an exterior of implant 514 (e.g., on threads 576, or between such threads, as shown). In another embodiment, the markers may be positioned internally, e.g., in the interior cavity of implant 514 into which locking structure 150 and threads 142 are received.

Figure 27C:
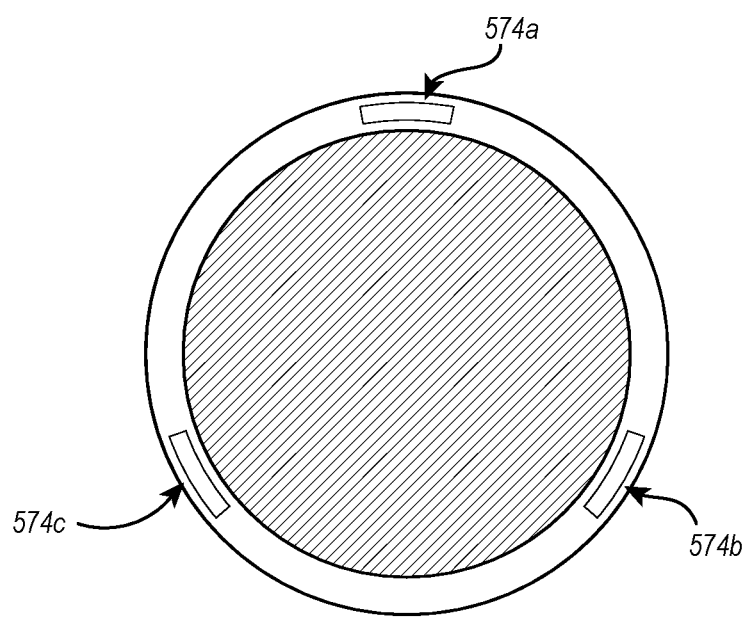

In an embodiment, the markers 574 may be provided as a plurality of series of markers. FIGS. 27A and 27C illustrate such an arrangement. For example, as shown in FIG. 27C such a configuration may include series 574a, 574b, and 574c, where each series includes a plurality of markers as shown in FIG. 27A. Each series 574a, 574b, 574c comprises a plurality of vertically "stacked" markers (FIG. 27A), with each marker 574 positioned some predetermined distance above or below the next adjacent marker. For example, the markers may be positioned 1-3 mm apart from one another (e.g., 2 mm apart from one another). When seen in a 3-D virtual model or other image derived from a scan taken of the patient's oral cavity and surrounding hard and soft tissues, the 2 mm or other particular spacing of such markers will allow a practitioner to easily recognize the depth or length required for the dental implant, as well as the particular location of any portions of the implant, even once installed into the jaw bone of the patient.

The implant may be part of a kit of implants, in which multiple different diameters of implants are provided (e.g., a small diameter, a medium diameter, a large diameter), in which all implants are of the same length. For example, all implants may be provided with a "long" length of 16 mm. By way of example, the implants may be provided with diameters from 2 mm to 6 mm, e.g., in three different sizes, such as 3 mm, 4 mm, and 5 mm. Those skilled in the art will appreciate that such diameter values refer to the diameter of the "platform" of the dental implant. Other particular diameters that could be provided will be apparent. This allows the practitioner to select an appropriate diameter implant, install it into the jaw bone, and cut the implant to the needed length. Such a cut may be performed at the threaded distal end, or the proximal attachment end (i.e., removing a portion thereof), as desired. Any suitable biocompatible material may be used for forming the implant. Even where the implant is formed from titanium or zirconia (or zirconium or other biocompatible material), such a cut is easily achievable using a dental drill. The 16 mm long implant may be cut to any value shorter than its starting 16 mm length (e.g., as short as 6 mm, or 8 mm, such as 6 mm, 8 mm, 10 mm, 12 mm, 14 mm, or any value in between). More generally, the initial "long" length of the dental implant may be from 15 mm to 25 mm, or from 15 mm to 20 mm (e.g., 16 mm).

Markers 574 may be formed from a material different from the remainder of the implant body, so as to have a radiopacity that is greater than that of the surrounding portions of the implant body of implant 514. Such a difference in radiopacity allows a practitioner (and imaging software or hardware) to recognize the location of the markers, and to use that information for distance measurement (e.g., where adjacent markers are 2 mm apart or another spacing), as well as for determining the exact spatial relationship between the markers, the remainder of the implant 514, and the surrounding hard and soft oral tissues in and around the oral cavity.

One current issue with imaging is that typical titanium dental implants affect the resolution obtainable when creating a three-dimensional virtual model of the implant and the surrounding soft and hard tissues, as the titanium material causes scatter with CT, MRI and other imaging techniques that rely on electromagnetic radiation. For this reason, another material, such as zirconia, may be preferred for fabrication of the implant body. In another embodiment, use of a non-electromagnetic imaging technique (e.g., ultrasound) may be used, as such imaging techniques may not be susceptible to the same scatter issues described above.

Where a series of markers are provided (e.g., series 574a, 574b, 574c), such series may be positioned on different faces of the implant 514. Where the surface is circular or otherwise rounded as shown, such different faces may be defined as an angular separation between the series of markers (e.g., 90° apart, or 120° apart, or any value there-between). Of course, other angular separations may also be possible (e.g., 40° to 150° apart, 90° to 120° apart, or the like). A 120° separation may result in equal angular spacing of three series of markers around a circular cross section of the implant. FIG. 27C schematically illustrates placement of series 574a, 574b, and 574c of markers 574, where each series includes a series of vertically stacked markers (the vertical stack is seen in FIG. 27A). In FIG. 27C the stacks 574a, 574b, 574c are 120° apart.

The radiopaque markers 574 may be formed from a material having a radiopacity that is greater than that of the biocompatible material from which the threaded distal end and proximal attachment end of the implant are formed. Such radiopaque materials may include, but are not limited to one or more of gold, tantalum, tungsten, molybdenum, platinum, palladium, or other metals recognized to have higher radiopacity than the material from which the implant body is formed (e.g., titanium). Where ultrasound imaging is used, the marker material may have characteristics that similarly cause the markers to exhibit a contrast relative to the surrounding other material, when imaged with ultrasound. As used herein, the term "radiopacity" is intended to encompass such characteristics. In other words, the phenomenon of radiopacity is analogous to, and is intended to be sufficiently broad so as to encompass what may be termed "ultrasound-opacity".

Before conducting the scan, the practitioner may apply a radiopaque powder around the gingival cuff and any other surrounding surfaces, so that these surface contours better show up in the scan, if desired.

VI. Additional Anatomical Healing Caps and Methods of Manufacture

Figure 28A:
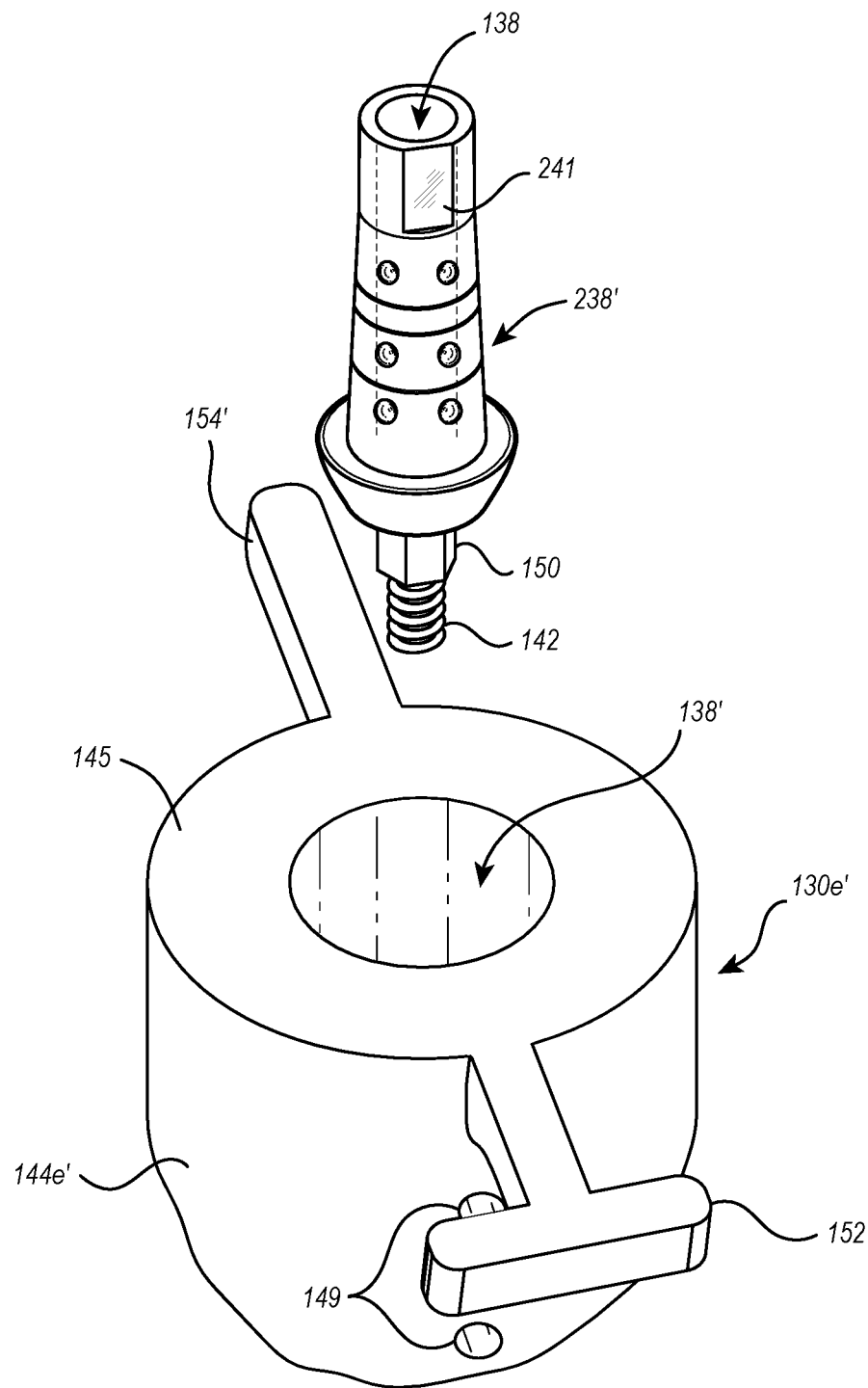
FIGS. 28A-28B illustrate exploded and cross-sectional views, respectively, of another anatomical healing cap formable about an abutment core, where the anatomical healing cap is configured to provide fully custom inside-to-outside back-filling of the subgingival void.
Figure 28B:
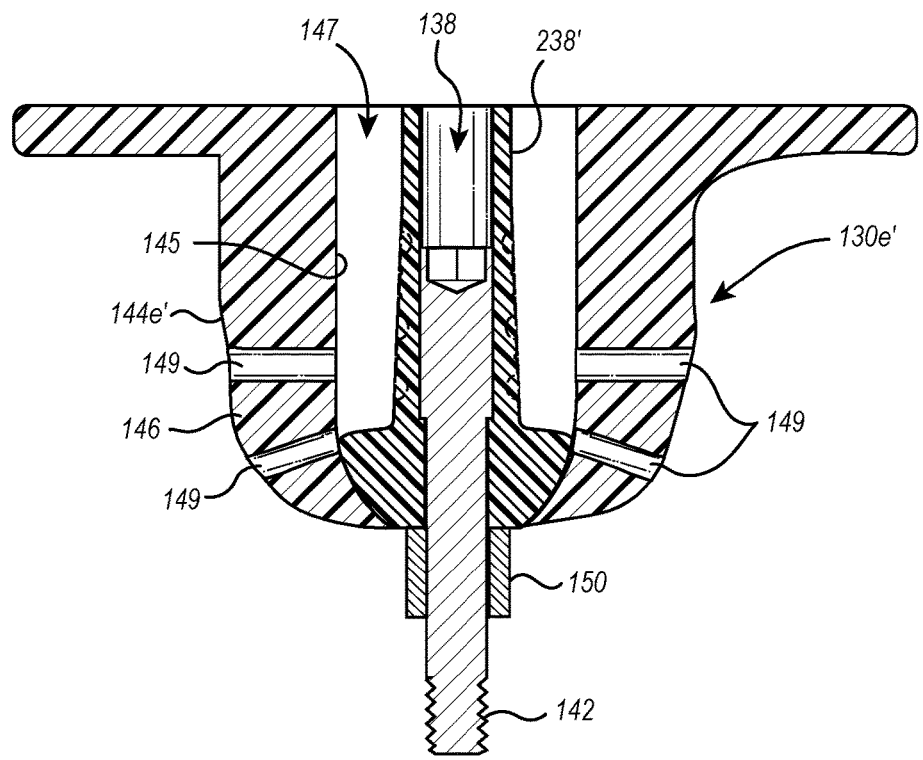

Numerous Figures already described illustrate various exemplary anatomical healing caps that may be provided for use in anatomically filling the subgingival void of a patient. Several such Figures describe formation of the anatomical healing cap around an abutment core (e.g., core 238' seen in FIG. 9B, as well as many other Figures). FIGS. 28A-28B show an anatomical healing cap 130e' that is similar to the anatomical healing cap 130e of FIGS. 6A-7B, of Applicant's U.S. patent application Ser. No. 14/485,351, already incorporated by reference, but which includes an enlarged hollow central channel therethrough, for receipt of an abutment core (e.g., 238'). Although FIGS. 28A-28D illustrate an anatomical healing cap configured for filling a subgingival void of a molar, it will be appreciated that any of the other shaped anatomical healing caps could include feature such as described in conjunction with FIGS. 28A-28D.

Because of the presence of enlarged central channel 138', cuff body 144e' is configured to include a peripheral portion 145 extending around the periphery of the cuff body 144e', with central channel 138' at its center. Central channel 138' is significantly wider than channel 138 described previously, so that a gap or space 147 exists between peripheral portion 145 and abutment core 238', when such core is positioned in channel 138'. In addition, with core 238' in place, both channel 138 and gap or space 147 will be present. The exterior surface, the cross-section, and the shape provided by peripheral portion 145 may provide the same benefits as described above relative to any of the described cuff bodies 144 (e.g., in which subgingival portion 146 provides substantially custom filling of the subgingival void for the given tooth position of the patient).

FIG. 28A illustrates how the abutment core 238' may be initially separate from the peripheral portion 145, but that core 238' can be coupled into a dental implant, in a similar manner as described previously (e.g., using threaded end 142 and locking structure 150). FIG. 28B illustrates that with abutment core 238' received within the channel 138', so as to be surrounded by peripheral portion 145, there is a gap or space 147 between the inner surface of peripheral portion 145 and the exterior surface of core 238', given the oversized nature of channel 138'. As illustrated, the peripheral portion 145 is also provided with one or more exit ports 149 positioned in portion 145 within the subgingival portion 146 of cuff body 144. For example, both upper and lower exit ports may be provided. Such upper and lower exit ports may be provided in an angularly spaced arrangement about peripheral portion 145. For example, such upper and lower ports may be 180° apart, 90° apart, or the like, to facilitate even filling and coverage of any small gaps that may exist between the substantially custom filling provided by the anatomical subgingival portion and the actual subgingival void of the given tooth position of the given patient. Although the ports 149 are illustrated as aligned with the directional alignment bodies 152 and 154', it will be appreciated that they may be offset therefrom, or additional exit ports may be provided.

Such a configuration allows better customization of the exterior surface and cross-section of the subgingival portion of the healing cuff body to the subgingival void. For example, while Applicant's previously described shapes and sizes of the cuff body, particularly the subgingival portion thereof, may provide for substantially custom filling of the subgingival void, there can be minor variances associated with individual patient's subgingival voids, such that the filling and support provided by the anatomical healing caps described in Applicant's previous filings is not fully custom, but is substantially custom, as the cuff bodies are mass manufactured to an idealized shape and size that is substantially matched to the subgingival void of a typical patient at a given tooth position. The embodiment shown in FIGS. 28A-28D actually allows for full customization of the subgingival portion of the anatomical healing cap, so as to provide fully customized fit in the subgingival void.

Figure 28C:
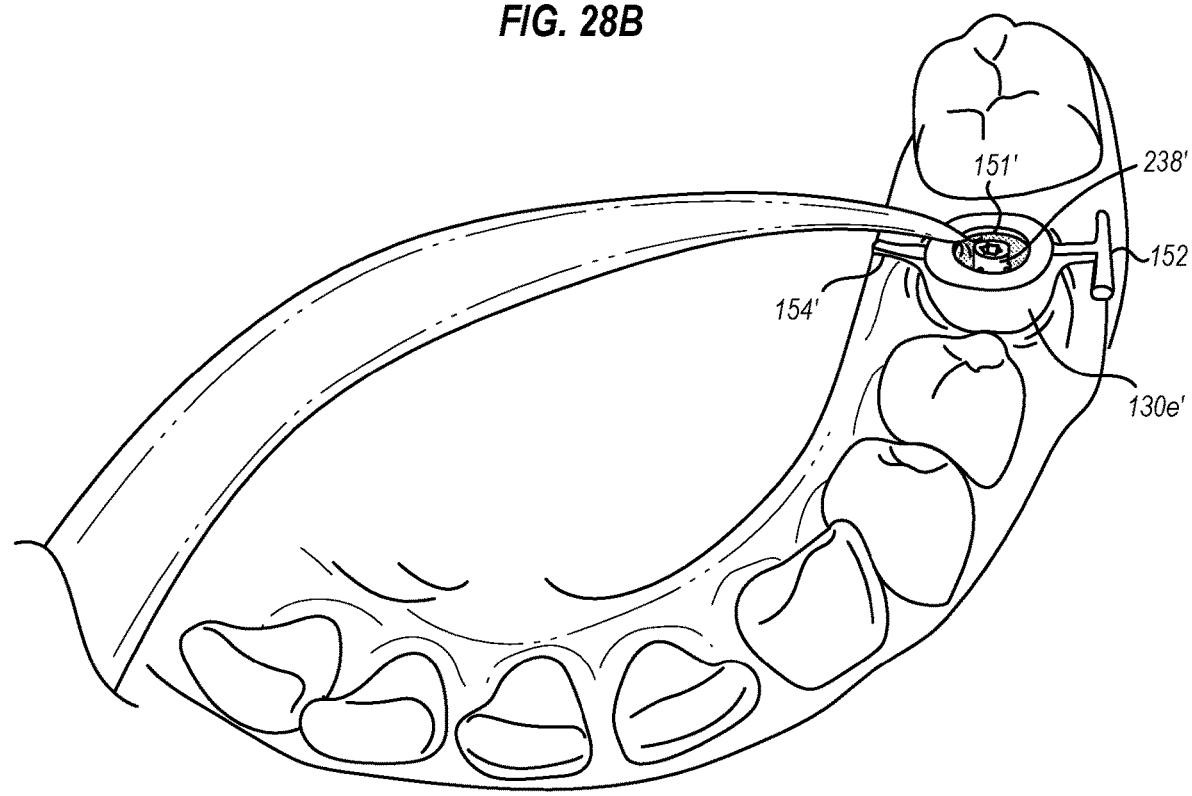
FIGS. 28C-28D illustrate a method in which a practitioner is back-filling the subgingival void from the inside-out, through a space between the abutment core and the periphery of the anatomical healing cap, where the curable resin flows into any gaps in the subgingival void through exit ports in the subgingival portion of the peripheral portion of the anatomical healing cap.
Figure 28D:
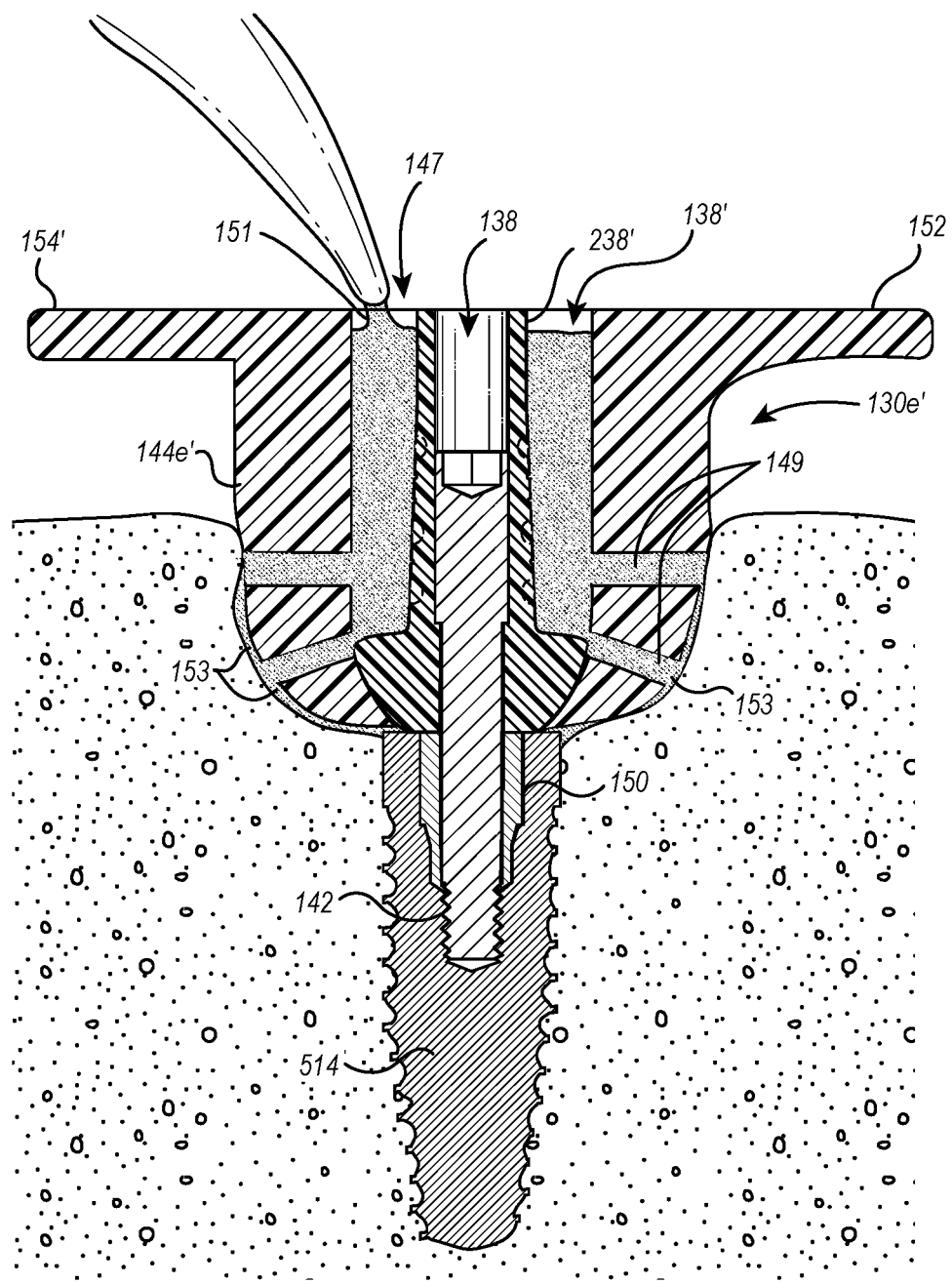

In particular, as shown in FIGS. 28C and 28D, such customization is achievable in-situ, with the abutment core 238' coupled into the dental implant (e.g., implant 14, or implant 514), with peripheral portion 145 of anatomical abutment 130e' positioned around core 238'. In other words, core 238' is inserted into widened channel 138', with locking structure 150 and/or threads 142 coupling core 238' into the implant 514. Core 238' may be inserted through the top of channel 138', rather than the bottom, particularly where insertion through the bottom may not be possible (e.g., where the bottom of core 238' is too wide to pass through the bottom of channel 138'.

In any case, with core 238' in position, the practitioner may verify that core 238' (particularly flat 241 thereof) and/or directional alignment body 152 are properly aligned (e.g., towards the buccal face), and then may backfill the space 147 with a curable or other hardenable dental material (e.g., a bis-acrylic resin) 151. Because of the presence of exit ports 149, any minor gaps 153 that may exist between the exterior surface of the subgingival portion of cuff body 144 are filled with such curable resin 151, so as to result in a fully custom filled and custom fitted subgingival void.

In an embodiment, the core 238' may comprise a transparent biocompatible material (e.g., such as that used in ANATOTEMP abutments). Examples of such materials may include various materials that allow transmission of curing light wavelengths, and may include materials such as various thermoplastic materials, such as acrylic, PEEK, or even various glasses or ceramics. For example, use of such a transparent core 238' would allow UV or blue curing light wavelengths to be transmitted through the core 238', curing a light-curable dental resin material that may be injected into space 147. In an embodiment, a resin material that does not necessarily rely on light curing may be used (e.g., bis-acrylic), also ensuring full curing of the employed resin material.

As used in this specification and the appended claims, the singular forms "a," "an" and "the" include plural referents unless the context clearly dictates otherwise.

The present invention can be embodied in other specific forms without departing from its spirit or essential characteristics. Thus, the described implementations are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A method of using a dental implant having customizable length characteristics and radiopaque markings to form a digital model of the dental implant within surrounding hard and soft tissue, the method comprising:
   providing a kit including a plurality of dental implants that are all of identical length and a healing cap, wherein a first dental implant is of a first diameter, a second dental implant is of a second diameter greater than the first diameter, and a third implant is of a third diameter greater than the second diameter, wherein each dental implant is of the same initial length, and each dental implant includes:
   an implant body including a threaded distal end configured for implant into a jaw bone of a patient and a proximal attachment end configured for attachment to the healing cap;
   wherein:
   the threaded distal end and the proximal attachment end are formed from a biocompatible material comprising at least one of titanium or zirconium, the implant body further comprising a plurality of radiopaque markers positioned on an exterior surface and in an interior cavity of the implant body; and
   the healing cap comprises a plurality of radiopaque markers positioned within or on the healing cap;
   selecting a dental implant from the kit of dental implants and cutting the dental implant from the initial length as provided to a shorter length, using a dental drill to make the cut;
   positioning the selected dental implant into a subgingival void in the jaw of a patient;
   attaching the healing cap to proximal attachment end of the dental implant;
   capturing an image of the selected dental implant and healing cap by scanning the patient's oral cavity with a scanning apparatus, wherein the radiopaque markers are positioned such that the radiopaque markers allow construction of a 3-dimensional virtual model of the implant, healing cap, and surrounding hard and soft tissues by a computing device, where precise positioning of the implant and the healing cap in the 3-dimensional model is determined based on positioning of the radiopaque markers.

2. The method as recited in claim 1, wherein the plurality of radiopaque markers are formed from a different material that has a radiopacity that is greater than that of the biocompatible material from which the threaded distal end and proximal attachment end are formed.

3. The method as recited in claim 1, wherein the first dental implant has a diameter of about 3 mm, the second dental implant has a diameter of about 4 mm, and the third dental implant has a diameter of about 5 mm, and wherein each of the implants has a starting length of at least 16 mm, so that they can be cut to any value shorter than the starting length.

* * * * *

UNITED STATES PATENT AND TRADEMARK OFFICE
CERTIFICATE OF CORRECTION

| | | |
|---|---|---|
| PATENT NO. | : 10,568,720 B2 | Page 1 of 1 |
| APPLICATION NO. | : 15/952064 | |
| DATED | : February 25, 2020 | |
| INVENTOR(S) | : Liston et al. | |

It is certified that error appears in the above-identified patent and that said Letters Patent is hereby corrected as shown below:

On the Title Page

Item (73), Assignee, change "Estetic" to –Esthetic–

In the Specification

Column 9
Line 23, change "formed." to –formed).–

Column 15
Line 35, change "manufacturer" to –manufacture–

Column 20
Line 28, remove [9B]

Column 25
Line 58, remove [,it]

Column 32
Line 57, change "feature" to –features–

Signed and Sealed this
Twenty-first Day of April, 2020

Andrei Iancu
*Director of the United States Patent and Trademark Office*